US009040245B2

(12) United States Patent
Elsemore et al.

(10) Patent No.: US 9,040,245 B2
(45) Date of Patent: *May 26, 2015

(54) METHODS, DEVICES, KITS AND COMPOSITIONS FOR DETECTING ROUNDWORM, WHIPWORM, AND HOOKWORM

(75) Inventors: David Allen Elsemore, South Portland, ME (US); Jinming Geng, Scarborough, ME (US); Laurie A. Flynn, Raymond, ME (US); Michael Crawford, St. Louis, MO (US)

(73) Assignees: IDEXX Laboratories, Inc., Westbrook, ME (US); Divergence, Inc., St. Louis, MO (US)

( * ) Notice: Subject to any disclaimer, the term of this patent is extended or adjusted under 35 U.S.C. 154(b) by 914 days.

This patent is subject to a terminal disclaimer.

(21) Appl. No.: 13/110,487

(22) Filed: May 18, 2011

(65) Prior Publication Data

US 2013/0149694 A1 Jun. 13, 2013

Related U.S. Application Data

(60) Division of application No. 12/467,826, filed on May 18, 2009, now Pat. No. 7,951,547, and a continuation-in-part of application No. 11/763,592, filed on Jun. 15, 2007, now Pat. No. 7,736,660, and a continuation-in-part of application No. 11/763,583, filed on Jun. 15, 2007.

(60) Provisional application No. 61/122,260, filed on Dec. 12, 2008, provisional application No. 61/128,077, filed on May 19, 2008, provisional application No. 61/128,079, filed on May 19, 2008, provisional application No. 61/128,076, filed on May 19, 2008, provisional application No. 61/128,099, filed on May 19, 2008, provisional application No. 61/122,254, filed on Dec. 12, 2008.

(51) Int. Cl.
*G01N 33/53* (2006.01)
*G01N 33/567* (2006.01)
*G01N 33/68* (2006.01)

(52) U.S. Cl.
CPC ........ *G01N 33/6893* (2013.01); *G01N 33/5308* (2013.01); *G01N 2333/43526* (2013.01)

(58) Field of Classification Search
CPC ........................ G01N 33/6893; G01N 33/5308
See application file for complete search history.

(56) References Cited

U.S. PATENT DOCUMENTS

| 4,322,495 A | 3/1982 | Kato |
| 4,756,908 A | 7/1988 | Lew |
| 4,789,631 A | 12/1988 | Maggio |
| 4,839,275 A | 6/1989 | Weil |
| 4,978,504 A | 12/1990 | Nason |
| 5,078,968 A | 1/1992 | Nason |
| 5,238,649 A | 8/1993 | Nason |
| 5,266,266 A | 11/1993 | Nason |
| 5,726,010 A | 3/1998 | Clark |
| 5,753,787 A | 5/1998 | Hawdon et al. |
| 5,843,706 A | 12/1998 | Cobon et al. |
| 5,882,943 A | 3/1999 | Aldeen |
| 6,057,166 A | 5/2000 | Childs et al. |
| 6,391,569 B1 | 5/2002 | Grieve et al. |
| 6,596,502 B2 | 7/2003 | Lee |
| 7,303,752 B2 | 12/2007 | Hotez et al. |
| 7,736,660 B2 | 6/2010 | Elsemore et al. |
| 7,951,547 B2 * | 5/2011 | Elsemore et al. ............. 435/7.1 |
| 2002/0132270 A1 | 9/2002 | Lee |
| 2003/0129680 A1 | 7/2003 | O'Connor, Jr. |
| 2003/0202036 A1 | 10/2003 | Caplan et al. |
| 2004/0014087 A1 | 1/2004 | Hodgson et al. |
| 2004/0214244 A1 | 10/2004 | Tonelli et al. |
| 2005/0042232 A1 | 2/2005 | Hotez et al. |
| 2006/0198844 A1 | 9/2006 | Langenfeld |
| 2007/0053920 A1 | 3/2007 | Heath et al. |
| 2008/0033148 A1 | 2/2008 | Xu et al. |
| 2008/0108793 A1 | 5/2008 | Berman et al. |

(Continued)

FOREIGN PATENT DOCUMENTS

| WO | 98/12563 | 3/1998 |
| WO | WO 00/17654 | 3/2000 |

(Continued)

OTHER PUBLICATIONS

Bowie et al., "Deciphering the Message in Protein Sequences: Tolerance to Amino Acid Substitutions", Science, 1990, 247:1306-1310.
Uniprot submission P07852. Aug. 1, 1988. [Retrieved from the Internet Mar. 30, 2010: <URL:http://www.uniprot.org/uniprot/P07852>].
GenBank Accession No. AAD01628. Jan. 1, 1999. [Retrieved from the Internet Feb. 25, 2010: <URL:http://ncbi.nlm.nih.gov/protein/410955)].
GenBank Accession No. BM965689. Mar. 1, 2002 ;Retrieved from the Internet Feb. 25, 2010: <URL:http://ncbi.nlm.nih.gov.nucest/19558140>).

(Continued)

*Primary Examiner* — Albert Navarro
(74) *Attorney, Agent, or Firm* — McDonnell Boehnen Hulbert & Berghoff LLP

(57) ABSTRACT

Methods, devices, kits and compositions for detecting the presence or absence of one or more helminthic coproantigens in a sample are disclosed herein. The methods, devices, kits and compositions of the present invention may be used to confirm the presence or absence of roundworm, whipworm and/or hookworm in a fecal sample from a mammal and may also be able to distinguish between one or more helminth infections. Confirmation of the presence or absence of roundworm, whipworm and/or hookworm in the mammal may be made, for example, for the purpose of selecting an optimal course of treating the mammal and/or for the purpose of determining whether the mammal has been rid of the infection after treatment has been initiated.

23 Claims, 26 Drawing Sheets

(56) References Cited

U.S. PATENT DOCUMENTS

| | | | |
|---|---|---|---|
| 2008/0311557 | A1 | 12/2008 | Elsemore et al. |
| 2008/0311600 | A1 | 12/2008 | Elsemore et al. |
| 2009/0286227 | A1 | 11/2009 | Elsemore et al. |
| 2009/0286228 | A1 | 11/2009 | Elsemore et al. |
| 2009/0286229 | A1 | 11/2009 | Elsemore et al. |
| 2009/0286230 | A1 | 11/2009 | Elsemore et al. |
| 2009/0286231 | A1 | 11/2009 | Elsemore et al. |
| 2010/0151500 | A1 | 6/2010 | Elsemore et al. |

FOREIGN PATENT DOCUMENTS

| | | |
|---|---|---|
| WO | 02/075313 A1 | 9/2002 |
| WO | WO 03/032917 | 4/2003 |
| WO | 2004/097412 A2 | 11/2004 |
| WO | WO 2006/135799 | 12/2006 |
| WO | WO 2008/156650 | 12/2008 |
| WO | WO 2009/143080 | 11/2009 |
| WO | WO 2009/143083 | 11/2009 |

OTHER PUBLICATIONS

GenBank Accession No. BQ088867. Apr. 1, 2002 [Retrieved from the Internet Feb. 25, 2010: <URL:http://ncbi.nlm.nih.gov.nucest/20062868>].
GenBank Accession No. AAC17174. May 1, 1998. [Retrieved from the Internet Feb. 25, 2010: <URL:http://ncbi.nlm.nih.gov/protein/3152922>].
GenBank Accession No. AAC47345. Oct. 1, 2007. [Retrieved from the Internet Feb. 25, 2010: <URL:http://ncbi.nlm.nih.gov/protein/1663728>].
GenBank Accession No. AAG31482. Nov. 1, 2000. [Retrieved from the Internet Feb. 25, 2010. <URL:http://ncbi.nlm.nih.gov/protein/11138792>].
GenBank Accession No. NP_510821. Nov. 2008. [Retrieved from the Internet Feb. 25, 2010. <URL:http://ncbi.nlm.nih.gov/protein/17551598>].
Uniprot submission Q06811. Nov. 1997. [Retrieved from the Internet Feb. 25, 2010: <URL://www.uniprot.org/uniprot/Q06811>].
Uniprot submission Q24702. Nov. 1996. [Retrieved from the Internet Feb. 25, 2010: <URL:http://www/uniprot.org/uniprot/Q24702>].
Uniprot submission P91811. May 1997. [Retrieved from the Internet Feb. 25, 2010: <URL:http://uniprot.org/uniprot/P91811>].
Uniprot submission O44397. Jun. 1998. [Retrieved from the Internet Nov. 11, 2009: <URL:http://uniprot.org/uniprot/044397>].
Wakelin, "Acquired immunity to *Trichuris muris* in the albino laboratory, mouse", Parasitology, 1967, 57:515-524.
Lillywhite et al., "Humoral immune responses in human infection with the whipworm *Trichuris trichiura*", Parasite Immunol. 1991, 13:491-507.
Drake et al., "The major secreted product of the whipworm, *Trichuris*, is a pore-forming protein", Proc. Biol. Sci., 1994, 257:255-261.
Jenkins et al., "Functional antigens of *Trichuris muris* released during in vitro maintenance: their immunogenicity and partial purification", Parasitology, 1983, 86:73-82.
Drake et al., "Molecular and functional characterization of a recombinant protein of *Trichuris trichiura*", Proc. Biol. Sci., 1998. 265:1559-1565.
Nukumi et al., "Whey acidic protein (WAP) regulates the proliferation of mammary epithelial cells by preventing serine protease from degrading laminin", J Cell Physiol., May 31, 2007, 213:793-800.
Barker et al., "Isolation of a gene family that encodes the porin-like proteins from the human parasitic nematode *Trichuris trichiura*", Gene, 1999, 229:131-136.
Parkinson et al., "400 000 nematode ESTs on the Net", Trends Parasitol., Jul. 2003, 19(7):283-286.
Lillywhite et al., "Identificaton and characterization of excreted/secreted products of *Trichuris trichiura*", Parasite Immunol., 1995. 17:47-54.
Daub et al., "A survey of genes expressed in adults of the human hookworm, *Necator americans*", Parasitology, 2000, 120:171-184.
De Oliveira Vasconcelos, et al., "Identification of stage-specific proteins of *Angiostrongylus vasorum* (Baillet, 1866) Kamensky", Parasitol Res., 2007, 102(3):389-395.
Kania et al., "*Anoplocephala perfoliata* coproantigen detection: a prelimina study", Vet Parasitol, 2005, 127(2):115-119.
Song et al., "Cross-reactivity between sera from dogs experimentally infected with *Dirofilaria immitis* and crude extract of *Toxocara canis*", Korean J Parasital, Dec. 2002, 40(4)'195-198.
Allan et al., "Coproantigen detection for immunodiagnosis of echinococcosis and taeniasis in dogs and humans", Parasitology, 1992, 104:347-355.
GenBank Accession No. CB098869. Jan. 28, 2003. [Retrieved from the Internet Mar. 30, 2010: <URL:http://ncbi.nlm.nih.gov/nucest/27924676>].
GenBank Accession No. CB099165. Jan. 28, 2003. [Retrieved from the Internet Mar. 30, 2010: <URL:http://ncbi.nlm.nih.gov/nucest/27924972>].
GenBank Accession No. 08099244. Jan. 28, 2003. [Retrieved from the Internet Mar. 30, 2010: <URL:http://ncbi.nlm.nih.gov/nucest/27925051>].
GenBank Accession No. CB099367. Jan. 28, 2003. [Retrieved from the Internet Mar. 30, 2010: <URL:http://ncbi.nlm.nih.gov/nucest/27925174>].
GenBank Accession No. CB188155. Feb. 5, 2003 [Retrieved from the Internet Mar. 30, 2010: <URL: http://ncbi.nlm.nih.gov/nucest/28251547>].
GenBank Accession No. CB188174. Feb. 5, 2003. [Retrieved from the Internet Mar. 30, 2010: <URL:http://ncbi.nlm.nih.gov/nucest/28251566>) .
GenBank Accession No. CB188239. Feb. 5, 2003. [Retrieved from the Internet Mar. 30, 2010: <URL:http://ncbi.nlm.nih.gov/nucest/28251631>].
GenBank Accession No. CB188637. Feb. 5, 2003. [Retrieved from the Internet Mar. 30, 2010: <URL:http://ncbi.nlm.nih.gov/nucest/28252029>].
GenBank Accession No. CB189034. Feb. 5, 2003. [Retrieved from the Internet Mar. 30, 2010: <URL:http://ncbi.nlm.nih.gov/nucest/28252426>].
GenBank Accession No. CB189036. Feb. 5, 2003. [Retrieved from the Internet Mar. 30, 2010: <URL:http://ncbi.nlm.nih.gov/nucest/28252428>].
GenBank Accession No. 08189116. Feb. 5, 2003. [Retrieved from the Internet Mar. 30, 2010: <URL:http://ncbi.nlm.nih.gov/nucest/28252508>].
GenBank Accession No. CB189285. Feb. 5, 2003. [Retrieved from the Internet Mar. 30, 2010: <URL:http://ncbi.nlm.nih.gov/nucest/28252677>].
GenBank Accession No. CB189434. Feb. 5, 2003. [Retrieved from the Internet Mar. 30, 2010: <URL:http://ncbi.nlm.nih.gov/nucest/28252826>].
GenBank Accession No. CB277501. Feb. 25, 2003. [Retrieved from the Internet Mar. 30, 2010: <URL:http://ncbi.nlm.nih.gov/nucest/28561086>) .
Gen Bank Accession No. CB277590. Feb. 25, 2003. [Retrieved from the Internet Mar. 30, 2010: <URL:http://ncbi.nlm.nih.gov/nucest/28561175>].
GenBank Accession No. CB277641. Feb. 25, 2003. [Retrieved from the Internet Mar. 30, 2010: <URL:http://ncbi.nlm.nih.gov/nucest/28561226>).
GenBank Accession No. CB277653. Feb. 25, 2003. [Retrieved from the Internet Mar. 30, 2010: <URL:http://ncbi.nlm.nih.gov/nucest/28561238>].
GenBank Accession No. CB277950. Feb. 25, 2003. [Retrieved from the Internet Mar. 30, 2010: <URL:http://ncbi.nlm.nih.gov/nucest/28561535>].
GenBank Accession No. CB188241. Feb. 5, 2003 [Retrieved from the Internet Mar. 30, 2010: <URL:http://ncbi.nlm.nih.gov/nucest/28251633>].
GenBank Accession No. CB277846. Feb. 25, 2003. [Retrieved from the Internet Mar. 30, 2010: <URL:http://ncbi.nlm.nih.gov/nucest/28561431>].

(56) References Cited

OTHER PUBLICATIONS

GenBank Accession No. CB277826. Feb. 25, 2003. [Retrieved from the Internet Mar. 30, 2010: <URL:http://ncbi.nlm.nih.gov/nucest/28561411>).
GenBank Accession No. CB189366. Feb. 5, 2003. [Retrieved from the Internet Mar. 30, 2010: <URL:http://ncbi.nlm.nih.gov/nucest/28252758>].
GenBank Accession NO. CB098807. Jan. 28, 2003. [Retrieved from the Internet Mar. 30, 2010: <URL:http://ncbi.nlm.nih.gov/nucest/27924614>].
GenBank Accession No. CB189370. Feb. 5, 2003. [Retrieved from the Internet Mar. 30, 2010; <URL:http://ncbi.nlm.nih.gov/nucest/28252762>].
GenBank Accession No. BQ89025. Apr. 5, 2002. [Retrieved from the Internet Mar. 30, 2010: <URL:http://ncbi.nlm.nih.gov/nucest/20063226>].
GenBank Accession No. BM966041. Mar. 20, 2002. [Retrieved from the Internet Mar. 30, 2010: <URL:http://ncbi.nlm.nih.gov/nucest/19558790>].
GenBank Accession No. BQ088880. Apr. 5, 2002 [Retrieved from the Internet Mar. 30, 2010: <URL:http://ncbi.nlm.nih.gov/nucest/20063081>].
Uniprot submission P19398, Nov. 1, 1990, [Retrieved from the Internet Mar. 30, 2010: <URL: http://www.uniprot.org/uniprot/P19398>).
Uniprot submission O77416. May 16, 2003. [Retrieved from the Internet Mar. 30, 2010: <URL: http://www.uniprot.org/uniprot/O77416>].
Uniprot submission Q2VMT7. Jan. 10, 2006. [Retrieved from the Internet Mar. 30, 2010: <URL: http://www.uniprot.org/uniprot/Q2VMT7>].
Uniprot submission Q9U6V1. May 1, 2000. [Retrieved from the Internet Mar. 30, 2010: <URL: http://www.uniprot.org/uniprot/Q9U6V1>].
Uniprot submission Q16938, Nov. 1, 1996. [Retrieved from the Internet Mar. 30, 2010 <URL: http://www.uniprot.org/uniprot/Q16938>].
Uniprot submission Q962V8. Dec. 1, 2001. [Retrieved from the Internet Mar. 30, 2010: <URL:http://www.uniprot.org/uniprot/Q962V8>].
Ambler, et al., "Biological Techniques for Studying the Allergenic Components of Nematodes. I. Detection of Allergenic Components in *Ascaris suum* Extracts". Immunol. Methods, vol. 1, No. 4, pp. 317-327, (1972).
Britton, et al., "Extensive diversity in repeat unit sequences of the cDNA encoding the polyprotein antigen/allergen from the bovine lungworm *Dictyocaulus viviparous*", Mol. Biochem. Parasitol. vol. 72, pp. 77-88, (1995).
Christie, et al., "The ABA-1 allergen of the nematode *Ascaris suum*: epitope stability, mass spectrometry, and N-terminal sequence comparison with its homologue in *Toxocara canis*", Clin. Exp. Immunol., vol. 92, pp. 125-132, (1993).
Kennedy, "Stage-specific secreted antigens of the parasitic larval stages of the nematode *Ascaris*" Immunology, vol. 58, No. 3, pp. 515-522, (1986).
McGibbon, et al., "Identification of the major *Ascaris* allergen and its purification to homogeneity by high-performance liquid chromatography", Mol. Biochem. Parasitol., vol. 39, No. 2, pp. 163-172, (1990).
Meenan, et al., "Resonance assignment of ABA-1A, from *Ascaris suum* nematode polyprotein allergen", J. Biomol. NMR, vol. 32, No. 2 p. 176, (2005).
Poole, et al., "Cloning of a cuticular antigen that contains multiple tandem repeats from the filarial parasite *Dirofilaria immitis*", Proc. Natl. Acad. Sci. USA, vol. 89, No. 13, pp. 5986-5990, (1992).
Solovyova, et al., "The polyprotein and FAR lipid binding proteins of nematodes, shape and monomer/dimer states in ligand-free and bound forms", Eur. Biophys. J., vol. 32, No. 5, pp. 465-476, (2003).
Spence, et al., "A cDNA encoding repeating units of the ABA-1 allergen of *Ascaris*", Mol. Biochem. Parasitol. vol. 57, pp. 339-343, (1993).

The *C. Elegans* Sequencing Consortium, et al., "Genome Sequence of the Nematode *C. elegans*: A Platform for Investigating Biology", Science, vol. 282, pp. 2012-2018, (1998).
Tweedie, et al., "*Brugia pahangi* and *Brugia malayi*: a surface-associated glycoprotein (gp15/400) is composed of multiple tandemly repeated units and processed from a 400-kDa precursor", Exp. Parasitol., vol. 76, No. 2, pp. 156-164, (1993).
Westermarck, et al., "Faecal hydrolase activity as determined by radial enzyme diffusion: a new method for detecting pancreatic dysfunction in the dog", Res. Vet. Sci., vol. 28, No. 3, pp. 341-346, (1980) (Abstract).
Williams, et al., "Comparison of methods for assay of the fecal proteolytic activity", Vet. Clin. Pathol, vol. 19, No. 1, pp. 20-24, (1990) (Abstract).
Williams, et al., "Fecal proteolytic activity in clinically normal cats and in a cat with exocrine pancreatic insufficiency", J. Am. Vet. Med. Assoc., vol. 197, No. 2, pp. 1112-1113, 1116, (1990) (Abstract).
Babin, et al., "The isoinhibitors of Chymotrypsin/Elastase from *Ascaris lumbricoides*: The Primary Structure", Archives of Biochemistry and Biophysics, vol. 232, No. 1, pp. 143-161, (1984).
Cappello, et al., "*Ancylostoma caninum* anticoagulant peptide. A hookworm-derived inhibitor of human coagulation factor Xa", Proc. Natl. Acad. Sci., vol. 92, pp. 6152-6156, (1995).
Ford, et al., "Characterization of a Novel Filarial Serine Protease Inhibitor, Ov-SPI-1, from *Onchocerca volvulus*, with Potential Multifunctional Roles during Development of the Parasite", J. of Biol. Chem., vol. 280, No. 49, pp. 40845-40856, (2005).
Fraefel, et al., "The amino acid sequence of a try inhibitor isolated from *Ascaris* (*Ascaris lumbricoides* var. suum)", Biochim. Biophys Acta, vol. 154, pp. 615-617, (1968).
Goodman, et al., "Isolation of the Trypsin Inhibitors in *Ascaris lumbricoides* var. suum Using Affinity Chromatograpy" Analytical Biochemistry, vol. 120, pp. 387-393 (1982).
Grasberger, et al., "High-resolution structure of *Ascaris* trypsin inhibitor in solution: direct evidence for a pH-induced conformational transition in the reactive site", Structure, vol. 2, No. 7, pp. 669-678, (1994).
Gronenborn, et al., "Sequential resonance, assignment and secondary structure determination of the *Ascaris* trypsin inhibitor, a member of a novel class of proteinase inhibitors", Biochemistry, vol. 29, No. 1, pp. 183-189, (1990).
Harrison, et al., "Molecular Characterization of *Ancylostoma* Inhibitors of Coagulation Factor Xa", J. of Biol. Chem., vol. 277, No. 8, pp. 6223-6229, (2002).
Hawley et al., "*Ascaris suum*: Are Trypsin Inhibitors Involverd in Species Specificity of Ascarid Nematodes?", Experimental Parasitology, vol. 75, pp. 112-118 (1992).
Huang, et al., "The molecular structure of the complex of *Ascaris* chymotripsin/elastase inhibitor with porcine elastase", Structure, vol. 2, No. 7, pp. 679-689, (1994).
Lu, et al., "*Anisakis simplex*: Mutational Bursts in the Reactive Site Centers of Serine Protease Inhibitors from an Ascarid Nematode", Experimental Parasitology, vol. 89, pp. 257-261, (1998).
Martzen, et al., "*Ascaris suum*: Localization by Immunochemical and Fluorescent Probes of Host Proteases and Parasite Proteinase inhibitors in Cross-sections", Experimental Parasitology, vol. 80, pp. 139-149, (1985).
Nguyen, et al., "Expression and characterization of elastase inhibitors from the ascarid nematodes *Anisakis simplex* and *Ascaris suum*", Mol. Biochem. Parasitology, vol. 102, pp. 79-89, (1999).
Peanasky, et at "The Isoinhibitors of Chymotrypsin/Elastase from *Ascaris lumbricoides*: Isolation by Affinity Chromatography and Association with the Enzymes", Archives of Biochemistry and Biophysics, vol. 232, No. 1, pp. 127-134, (1984).
Rhoads, et al., "*Trichuris suis*: A Secretory Serine Protease Inhibitor", Experimental Parasitology, vol. 94, pp. 1-7, (2000).
Rhoads, et al., "*Trichuris suis*: A Secretory Chymotrypsin/Elastase Inhibitor with Potential as an Immunomodulator", Experimental Parasitology, vol. 95, pp. 36-44, (2000).
Stanssens, et al., "Anticoagulant repertoire of the hookworm *Ancylostoma canium*". Proc. Nat. Acad. Sci., vol. 93, pp. 2149-2154, (1998).

(56) References Cited

OTHER PUBLICATIONS

Uniprot submission P07851. Aug. 1988. [Retrieved from the internet Dec. 13, 2009: URL:http://www.uniprotorg/uniprot/P078511 in entirety.
Uniprot Submission P91811. May 1997 [Retrieved from the internet Nov. 7, 2009].
Uniport submission O44397. Jun. 1988 [Retrieved from the internet Nov. 11, 2009: [<URL:http://www.uniport.org/uniport/044397>].
Bailey, "The Raising of a Polyclonal Antiserum to a Protein", Methods Mol. Biol., vol. 32, pp. 381-388, (1994).
Dean, "Preparation and Characterization of Monoclonal Antibodies to Proteins and Other Cellular Components", Methods Mol. Biol., vol. 32. pp. 361-379, 1994 (Abstract).
Dean, "Preparation and Testing of Monoclonal Antibodies to Recombinant Proteins", Methods Mol. Biol., vol. 80, pp. 23-37, (1998).
Drenckhahnn, et al., "Production of Polyclonal Antibodies against Proteins and Peptides", Methods Cell Biol., vol. 37, pp. 7-56, (1993).
Dryden, et al., "Comparison of Common Fecal Flotation Techniques for the Recovery of Parasite Eggs and Oocysts", Vet. Ther., vol. 6, No. 1, pp. 15-28, (2005).
Gullick, "Production of Antisera to Synthetic Peptides", Methods Mol. Biol., vol. 32, pp. 389-399, (1994).
Kennedy, "The Nematode Polyprotein Allergens/Antigens", Parasitol. Today, vol. 16, No. 9, pp. 373-80, (2000).
Memoranda, "Parasite Antigens", Bull. World Health Organ, vol. 52, pp. 237-249, (1975).
Morrison "In Vitro Antibodies: Strategies for Production and Application". Annu. Rev. Immunol., vol. 10, pp. 239-265, (1992).
Prociv et al., "Human enteric infection with *Ancyostoma caninum*: hookworms reappraised in the light of a "new" zoonosis", Acta. Tropica., vol. 62, pp. 23-44, (1996).
Wright, et al., "Genetically Engineered Antibodies: Progress and Prospects", Grit. Rev. Immunol., vol. 12 (3-4), pp. 125-168, (1992).
Xia, et al., "The ABA-1 allergen of *Ascaris lumbricoides*: sequence polymorphism stage and tissue-specific expression, lipid binding function and protein biophysical properties", Parasitiology, vol. 120 (Pt.2), pp. 211-224, (2000).
Yahiro, et al., "Identification, characterization and expression of *Toxocara canis* nematode polyprotein allergen TBA-1", Parasite Immnol., vol. 20, No. 8, pp. 351-357. (1998).
NCBI Blast: SEQ ID No. 4 (Performed Aug. 27, 2009 using http://blast.ncbi.nlm.nih.gov/blast.cgi).
Abdel-Rahman et al., Evaluation of a diagnostic monoclonal antibody-based capture enzyme-linked immunosorbent assay for detection of a 26- to 28-kd *Fasciola hepatica* coproantigen in cattle, American Journal of Veterinary Research 59:533-537 (1998).
Bungiro, et al. "Detection of Exeretory/Secretoly Coproantigens in Experimental in Hookworm infection," Am. J. Trop. Med. Hyg. 73(5):915-920 (2005).
Bungiro, Jr., et al., "Purification and Molecular Cloning of and Immunization with *Ancylostoma ceylancium* Excretory-Secretory Protein 2, an Immunocreative Immunoreactive Protein Produed by Adult Hookworms," Infection and Immunity 72(4):2203-2213 (2004).
Carleton et al., "Prevalence of *Dirofilaria immitis* and gastrointestinal helminths in cats euthanized at animal control agencies in northwest Georgia," Veterinary Parasitology 119:319-326 (2004).
Coulaud, J.P., et al., "Albendazole: a new single dose anthelmintic," Study in 1455 patients, Acta Tropica 41:87-90 (1984).
De Oliveira et al., "IgM-ELISA for diagnosis of *Schistosomiasis mansoni* in low endemic areas," Cadernos de saude publica / Ministerio da Saude, Fundacao Oswaldo Cruz, Escola Nacional de Saude Publica 19:255-261 (2003).

Deplazes et al., "Detection of *Taenia hydatigeria* copro-antigens by ELISA in dogs," Veterinary Parisitology 36:91-103 (1990).
Dumenigo et al., "Kinetics of antibody-based antigen detection in serum and faeces of sheep experimentally infected with *Fasciola hepatica*," Veterinary Parasitology 86:23-31 (1999).
Foreyt, W.J., "Veterinary Parasitology Reference Manual," Fifth Edition, 2001, ISBN 0-8138-2419-2, pp. 3-10.
Hill et al., "A *Trichuris* specific diagnostic antigen from culture fluids of *Trichuris suis* adult worms", Veterinary Parasitology, vol. 68, pp. 91-102, (1997).
Martinez-Maya et al., "Taeniosis and detection of antibodies against Cysticeri among inhabitants 4 a rural community in Guerro State, Mexico," Salud Publica de Mexico 45:84-89 (2003).
Ott et al., "Demonstration of both immunologically unique and common antigenic determinants in *Dirofilaria immitis* and *Toxocara canis* using monoclonal antibodies,"Veterinary Immunology and Immunopathology 10:147-153 (1985).
Roberts, L.S., et al., "Foundations of Parasitology," Fifth Edition. 1996. Library of Congress Card Catalog No. 94-72939, ISBN 0-697-26071-2, pp. 1-4.
Southworth, D., Exine development in *Gerbera jamesonii* (Asteraceae: Mutisieae), American Journal of Botany, 70:1038-1047 (1983).
Voller, Allster, "The Enzyme Linked Immunosorbent Assay"; Diagnostic Horizon; vol. 2, No. 1, pp. 1-7, Feb. 1978.
Willard et al., "Diagnosis of *Aelurostrongylus abstrusus* and *Dirofilaria immitis* infections in cats from a humane shelter," Journal of the American Veterinary Medical Association 192:913-916 (1988).
Yamasaki, et al., "Development of Highly Specific Recombinant *Toxocara canis* Second-Stage Larva Excretory-Secretory Antigen for Immunodiagnosis of Human Toxocariasis," Journal of Clinical Microbiology 38 (4):1409-1413 (2000).
Zhan et atl., "Molecular characterisation of *Ancylostoma*-secreted protein family from the adult stage of *Ancylostoma caninum*," International Journal for Parasitology 33:897-907 (2003).
Bethony, et al., "Antibodies against a secreted protein from hookworm larvae reduce the intensity of hookworm infection in humans and vaccinated laboratory animals", *FASEB Journal*, vol. 19, pp. 1743-1745.
Croese, et al., "Occult enteric infection by *Ancylostoma caninum*: A previously unrecognized zoonosis", *Gastroenerology*, 1994, vol. 106, pp. 3-12.
Garcia, et al., "Detection of *Giardia lamblia, Entamoeba histolytic/ Entamoeba dispar,* and *Cryptosporidium parvum* Antigens in Human Fecal Specimens, Using the Triage Parasite Panel Enzyme Immunoassay", J. Clin. Microbiol., 2000, vol. 38(9), pp. 3337-3340.
Gasser, et al., "Improved molecular diagnostic tools for human hookworms", *Expert Rev. Mol. Diagn.* 2009, vol. 9(1), pp. 17-21.
Hotez, at al, "Pediatric Geohelminth Infections: *Trichuriasis, Ascariasis,* and Hookworm Infections", *Seminarsin Pediatric Infectious Diseases*, 2000, vol. 11(5), pp. 236-244.
Johnson, et al., "Detection of gastrointestinal nematodes by a coproantigen capture ELISA", *Res. Vet, Sci.*, 1996, vol. 60, pp. 7-12.
Jones, et al., "Hookworm infection; molecular mechanisms of disease and targets for control", *Drug Discovery Today: Disease Mechanisms*, 2004, vol. (2), pp. 217-222.
Matsumura, et al., "Detection of circulating toxocaral antigens in dogs, by sandwich enzyme-immunoassay", *Immunology*, 1984, vol. 51(3), pp. 600-613.
Traub, et al., "Canine gastrointestinel parasitic zoonoses in India", *Trends in Parasit.*, 2005, vol. 21(1), pp. 42-48.

\* cited by examiner

```
cattcactgc ggttgtaaaa gcagtgcaga aatgaggctg gtcttccatg cggttattta      60
cctcacattg gggttcctca ccgacgccgt aagagaaaaa cgtggcaaat gtcctcctga     120
accaccgatc gcaggaaaca cgatctactg ccgcgatgat tttgattgtg gaggaagaca     180
gaagtgctgt acaattgcag aaggacgtgg atgcgtgccg ccctatggtg aacaacattt     240
cgaagtggtg aaaccgggtc attgcccagc tattccagcg gttacgggca tggcgaactt     300
ctgtaacact gatggcgact gtgatggacc gaaaaaatgt tgtctcacat cgcgcggcta     360
cgattgcaca catccattac acttcccaat ccagccacaa cctccagtag gacagtgccc     420
tccttcaaag ccccgtatcc caggaaaatg ggtagacatc tgcgctaagc atgccaactg     480
cccagaccca gagaagtgtt gcgacacgga gtatggcaac cgatgtatgg atgttggatt     540
agtgccagga caaggagaaa gaccaggcaa ttgcccgaac gaaccacgaa taagaggaac     600
taaatacgat tgccgacgag acgatgactg cgacggtgtg cagaaatgct gcttcactgt     660
tgagggacgt gagtgcgtgg aaccaagtag aaaaccactg gacaagcccg gacattgtcc     720
accaattccc gctgatgtgg gctcagccag gtactgcgac actgatcggg attgtgatgg     780
accaagaaaa tgctgcctct cttcgcgtgg ctatgaatgt aaacatccag tacactatcc     840
cgatcgagtg gagccactag taggagaatg cccaccatca cgacctcgca ttcctgggaa     900
atgggttgac atctgctcta agcatgccaa ctgcccagac ccagagaaat gttgcgacac     960
ggagtatggc aaccgatgta tggacgttgg attagtgcct ggacaaggag aaaaacctgc    1020
caactgccca aaggaaccac gaataagagg aactaagtac gactgtcgac gggacgatga    1080
ctgcgatggg aaacaaaagt gctgctacac aactgaaggc cgcgaatgcg tccatggtat    1140
atggccttaa atggttgctt cttcctataa taaaagcaaa cgaatcaaaa aaaaaaaaaa    1200
aaaaaaaaaa                                                           1210
```

(SEQ ID NO:1)

FIG. 3

```
gtaagagaaa aacgtggcaa atgtcctcctgaaccacga tcgcaggaaa cacgatctac    60
tgccgcgatg attttgattg tggaggaagacagaagtgct gtacaattgc agaaggacgt   120
ggatgcgtgc cgccctatgg tgaacaagatttcgaagtgg tgaaaccggg tcattgccca   180
gctattccag cggttacggg catggcgaacttctgtaaca ctgatggcga ctgtgatgga   240
ccgaaaaaat gttgtctcac atcgcgcggctacgattgta cacatccgtt acacttccca   300
atccagccac aacctccagt aggacagtgccctccttcaa agcccgtgt tccaggaaaa    360
tgggtagaca tctgcgctaa gcatgccaattgcccagacc cagagaagtg ttgcgacacg   420
gagtatggca accgatgtat ggatgttggattagtggcag gacaaggaga aagaccaggc   480
aattgcccga acgaaccacg aataagaggaactaaatacg attgccgacg agacgatgac   540
tgcgacggtg tgcagaaatg ctgcttcactgttgagggac gtgagtgcgt ggaaccaagc   600
agaaaaccac tggacaagcc cggacattgtccaccaattc ccgctgatgt gggctcagcc   660
aggtactgcg acactgatcg ggattgtgatggaccaagaa aatgctgcct ctcttcgcgt   720
ggctatgaat gtaaacatcc agtacactatccgatcgag tggagccact agtaggagaa    780
tgcccaccat cacgacctcg cattcctgggaaatgggttg acatctgctc taagcatgcc   840
aactgcccag acccagagaa atgttgcgacacggagtatg gcaacgatg tatggacgtt    900
ggattagtgc ctggacaagg agaaaaacctgccaactgcc caaaggaacc acgaataagg   960
ggaactaagt acgactgtcg acgggacgatgactgcgatg ggaaacaaaa gtgctgctac  1020
acaactgaag gccgcgaatg cgtccatggtatatggcct             1059
```

(SEQ ID NO:2)

FIG. 4

```
Consensus (SEQ ID NO: 9)   XXXXXXXXXXXXXXXXXXXXVREKRGKCPPEPPIAGNTIYCRDDEDCGGRQKCCTIAEGRGCVPPYGEQXFEVVKPGHCPA
                                    10        20        30        40        50        60        70        80
                           ----+----+----+----+----+----+----+----+----+----+----+----+----+----+----+----+
          (SEQ ID NO: 3)   MRLVETAVIYITLGFLTDAVREKRGKCPPEPPIAGNTIYCRDDEDCGGRQKCCTIAEGRGCVWYGEQHFEVVKPGHCPA   80
          (SEQ ID NO: 4)   --------------------VREKRGKCPPEPPIAGNTIYCRDDEDCGGRQKCCTIAEGRGCVPPYGEQDFEVVKPGHCPA   61

Consensus (SEQ ID NO: 9)   IPAVTGMANECNIDGDCDGMCCLISRGYDCTHPLHETIQPQPPVGQCPPSKPRXPGKWVDICAKHANCPDPEKCCDTE
                                    90       100       110       120       130       140       150       160
                           ----+----+----+----+----+----+----+----+----+----+----+----+----+----+----+----+
          (SEQ ID NO: 3)   IPAVIGMANECNIDGDCDGPKKCCLISRGYDCTHPLHETIQPQPPVGQCPPSKPRIPGKWVDICAKHANCPDPEKCCDTE  160
          (SEQ ID NO: 4)   IPAVIGMANFCNIDGDCDGPKKCCLTSRGYDCTHPLHETIQPQPPVGQCPPSKPRVPGKWVDICAKHANCPDPEKCCDTE  141

Consensus (SEQ ID NO: 9)   YGNRCMDVGLVXG+GERPGNCPNEPRIRGIKYDCRRDDCDGVQKCCETVEGRECVEPSRKPLDKPGHCPPIPADVGSAR
                                   170       180       190       200       210       220       230       240
                           ----+----+----+----+----+----+----+----+----+----+----+----+----+----+----+----+
          (SEQ ID NO: 3)   YGNRCMDVGLVPGQGERPGNCPNEPRIRGTKYDCRRDDCDGVQKCCETVEGRECVEPSRKPLDKPGHCPPIPADVGSAR  240
          (SEQ ID NO: 4)   YGNRCMDVGLVAGQGERPGNCPNEPRIRGIKYDCRRDDCDGVQKCCETVEGRECVEPSRKPLDKPGHCPPIPADVGSAR  221

Consensus (SEQ ID NO: 9)   YCDTDRDCDGPRKCCLSSRGYECKHPVHYPDRVEPLVGECPPSRPRIPGKWVDICSKHANCPDPEKCCDTEYGNRCMDVG
                                   250       260       270       280       290       300       310       320
                           ----+----+----+----+----+----+----+----+----+----+----+----+----+----+----+----+
          (SEQ ID NO: 3)   YCDTDRDCDGPRKCCLSSRGYECKHPVHYPDRVEPLVGECPPSRPRIPGKWVDICSKHANCPDPEKCCDTEYGNRCMDVG  320
          (SEQ ID NO: 4)   YCDTDRDCDGPRKCCLSSRGYECKHPVHYPDRVEPLVGECPPSRPRIPGKWVDICSKHANCPDPEKCCDTEYGNRCMDVG  301

Consensus (SEQ ID NO: 9)   LVPGQGEKPANCPKEPRIRGTKYDCRRDDDCDGKQKCCYTTEGRECVHGIWP
                                   330       340       350       360       370
                           ----+----+----+----+----+----+----+----+----+----+--
          (SEQ ID NO: 3)   LVPGQGEKPANCPKEPRIRGTKYDCRRDDDCDGKQKCCYTTEGRECVHGIWP  372   (SEQ ID NO: 4)
          (SEQ ID NO: 4)   LVPGQGEKPANCPKEPRIRGIKYDCRRDDDCDGKQKCCYTTEGRECVHGIWP  353
```

FIG. 5

```
caagaagatt tatggtgtggcagcttcgag acgaaggagg catcacttca cgctcgaaaa    60
cagtctggac acccacctgaaatggcttag ccacgagcaa aaggaggaac tgctgcaaat   120
gaagaaggac ggcaaatcgaagaaggagct ccaggataag atcatgcact attacgagca   180
cctcgaaggc gatgcgaaacatgaagcaac agagcaactg aagggcggat gccgcgagat   240
tcttaagcat gttgttggcgaggagaaagc agctgagatc aaagcactga agattctgg    300
agcaagcaaa gatgagcttaaagccaaggt cgaagaggca ctccacgcag tcaccgacga   360
agaaaagaag caacatatcgccgaattcgg tcccgcatgc aagaagattt atggtgtggc   420
agcttcgaga cgaaggaggcatcacttcac gctcgaaaac agtctggaca cccacctgaa   480
atggcttagc cacgagcaaaaggaggaact gctgcaaatg aagaaggacg gcaaatcgaa   540
gaaggagctc caggataagatcatgcacta ttacgagcac ctcgaaggga tgctcctcgc   600
gctatgtatc ctgtattgacggccttccaa cctatcacac ctgtcagtgc ggccttacat   660
tcgacgagcg tagaaagacctgtcttccta agcagctggt aaagtactgc ggaatcccag   720
aatctggaga ggcgtcggcggaagttggtg agtcgtacta acacagcacg ctctcgttgg   780
tgcagatgtt gtgtgaaatactttttgtcag ttttccgtgt gttttaaata aataaaaaat   840
tccgtaaaaa aaaaaaaaaaaaaaa       (SEQ ID                            865
                                  NO: 10)
```

FIG. 6

```
atttatggtgtggcagcttcgagacgaaggaggcatcacttcacgctcgaaaaagtctg    60
gacacccacctgaaatggcttagccacgagcaaaaggaggaactgctgaaaatgaagaaa  120
gatgggaaatcgaagaaggagctccaggataaggtgatgcacttctacgagcacctcgaa  180
ggcgatgcgaaacatgaagcaacagagcaactgaagggcggatgccgcgagatccttaag  240
catgttgttggtgaggagaaagcagctgagatcaaagcactgaaagattctggagcaagc  300
aaagatgagcttaaagccaaggtcgaagatgcactccacgcggtcaccgaagaagaaaag  360
aagcaacatatcgccgaatttggtccagcatgcaaggaaattttcggggtgccggttgat  420
gttcgtcacaaacgcgacccttatactaatatgacgcccgatgaagttgctgaaggacta  480
agaagttaacggtgatcgagcttttgcaaaaactggttgatgcttttaaattcttttaa  540
gccttttctttgtgttatttcggaattgtaccacacgaacagttagttccgaataaagaa  600
ctgtaattatgtaaaaaaaaaaaaaaaaaa                                 632
                              (SEQ ID NO: 11)
```

FIG. 7

```
Consensus (SEQ ID NO: 16)  XXXXXXXXXXXXXXXHHFTLEXSLDTHLKWLSHEQKEELLXMKKDGKSKKELQDKXMHXYEHLEGDAKHEATEQLKGGCREILK
                                   10        20        30        40        50        60        70        80
                          ----+---------+---------+---------+---------+---------+---------+---------+
     (SEQ ID NO: 14)      -----,        MHHFTLENSLDTHLKWLSHEQKEELLQMKKDGKSKKELQDKIMHYYEHLEGDAKHEATEQLKGGCREILK 70
     (SEQ ID NO: 13)      IYGVAASRRRRHHFTLEKSLDTHLKWLSHEQKEELLKMKKDGKSKKELQDKVMHFYEHLEGDAKHEATEQLKGGCREILK 80

Consensus (SEQ ID NO: 16)  HVVGEEKAAEIFALKDSGASKDELKAKVEXALHAVTDEEKKQHIAEFGFACKXIXGVXXXXX  XXXXXXXXXXX
                                   90       100       110       120       130       140       150       160
                          ----+---------+---------+---------+---------+---------+---------+---------+
     (SEQ ID NO:14)       HVVGEEKAAEIKALKDSGASKDELKAKVEEALHAVTDEEKKQHIAEFGPACKKIYGPACKKIYGVAAS------------------------ 131
     (SEQ ID NO: 13)      HVVGEEKAAEIKALKDSGASKDELKAKVEDALHAVTDEEKKQHIAEFGPACKEIFGVPIDVRHKRDPYTHMTPDEVAEGL 160

Consensus (SEQ ID NO:16 XX
                          --
     (SEQ ID NO:14)       --                                                                              131
     (SEQ ID NO:13)       RS                                                                              162
```

FIG. 8

```
agtcagtagc cactttaatc catcagaatg ctctctgttc ttgcgcttttcgctcttatt      60
acttttgctg tggccggtcc ggaaagctgc ggtccaaacg aagtgtggactgaatgtacc     120
ggttgcgaat tgaaatgtgg gcaagatgaa aatacgccgt gcacactaaactgtcgaccg     180
ccgtcatgtg agtgctctcc aggaagaggc atgagacgaa ccaacgatggaaggtgcatt     240
ccggctagtc agtgcccgca acacagggcc aagagagagg agcaatgcaagccaaatgag     300
cagtggtcac cgtgccgagg atgtgaagga acatgcgcac aaagatttgtcccttgcact     360
agaaactgcc gaccaccagg ctgtgaatgc gttgctggcg caggtttcgtacgtgacgct     420
gaaggaaact gcatcaagtt cgacgattgc ccgaagtaaa taataaccatacaaattgct     480
gattccaatt aaaataataa atgagtccag ctgttaaaaa aaaaaaaaaaaaa            535
```

(SEQ ID NO:17)

FIG. 9

```
cagtcagcag ctactttat ccatcggaat gctctctgtt cttgcgctttcgctcttat      60
tactttcgct gtggccgatc cgaaaagttg cggtccaaac gaagtgtggactgaatgtac   120
cggttgcgag ttgaaatgcg ggcaggatga ggatacgccg tgcacactaaactgtcggcc   180
gccgtcatgt gagtgctcac caggaagagg catgagacga accgacgatgggaggtgcat   240
tccggctagt cagtgccgc  aacacagagc caagagagag gagcagtgcaagccaaatga   300
gcagtggtca ccgtgccgag gatgtgaagg aacatgcgca caaagatttgtcccttgcac   360
tagaaactgc cgaccaccag gatgtgaatg cgttgctggc gcaggtttcgtacgtgacgc   420
tgcaggaaat tgcatcaagt tcgacgattg cccgaagtaa ataataaccatactaattgc   480
tgattacaat taaaataata aatgagtcca gctgttaaaa aaaaaaaaaaaaaaa        536
```

(SEQ ID NO:18)

FIG. 10

```
Consensus (SEQ ID NO: 23)  XXXXXXXXXXXXXXXXPXSCGPNEVWTECTGCELKCGQDEXTPCTLNCRPPSCECSPGRGMRRTXDGRCIPASQCPQHR
                                   10        20        30        40        50        60        70        80
                          ----+---------+---------+---------+---------+---------+---------+---------+
(SEQ ID NO: 21)           ----------------MGPESCGPNEVWTECTGCELKCGQDENTPCTLNCRPPSCECSPGRGMRRTNDGRCIPASQCPQHR  65
(SEQ ID NO: 20)           MLSVLALFALITFAVADPKSCGPNEVWTECTGCELKCGQDEDTPCTLNCRPPSCECSPGRGMRRTDDGRCIPASQCPQHR  80

Consensus (SEQ ID NO:23)  AKREEQCKPNEQWSPCRGCEGTCAQRFVPCTRNCRPPGCECVAGAGFVRDAXGNCIKFDDCPK
                                   90       100       110       120       130       140
                          ----+---------+---------+---------+---------+---------+
(SEQ ID NO: 21)           AKREEQCKPNEQWSPCRGCEGTCAQRFVPCTRNCRPPGCECVAGAGFVRDAEGNCIKFDDCPK  128
(SEQ ID NO: 20)           AKREEQCKPNEQWSPCRGCEGTCAQRFVPCTRNCRPPGCECVAGAGFVRDAAGNCIKFDDCPK  143
```

FIG 11

```
atcagcaggt tcgcttcaa atgcttccga taactttttgctggcaatt attgtcggtg     60
cagcagtagc tcaccgtaaa tgtggtccaa acgaagagtggaccgaatgc actggttgcg   120
aaattaagtg cggtcaagga gagcaaccat gccctatgatgtgtcgtccg ccatcgtgtg  180
aatgcatggc cggcaaagga ttacgaagaa cagcggacggaagatgcgtg ccggaggcac   240
aatgcccaaa aagaatggta aagcgagacg aaaaatgtgggccaaacgag aaattcctga   300
agtgcagagg ttgtgagggt acctgcaaag aacgtctcgttccctgccct agaatgtgca   360
aaccaccagg ttgcgaatgc cccgcttcag aaggattcgttcgcaatgac aaaggcgaat   420
gtatcaagtt cgacgactgc ccgaataaa ttcaataaatcaattttgt    (SEQ ID NO: 469
                                                          24)
```

FIG. 12

```
atcagcaggt   ttcgcttcaa   atgcttccgt   taactttttt   gctggcattt   attgtgggtg    60
cagcggtagc   tcaccgtaaa   tgtggtccaa   atgaagagtg   gacggaatgc   actggctgcg   120
aaatgaagtg   cggtgaagga   gagacaccat   gccctatgat   gtgtcgtccg   ccatcgtgtg   180
aatgcatggc   cggcaaagga   ttacgaagaa   caccggacgg   aagatgtgtg   ccggaggcac   240
aatgcccgaa   acatatggta   aagcgagatg   aaaaatgtgg   gaaaaacgag   aaattcctga   300
agtgcagagg   atgtgagggt   acgtgcaaag   aacgtctcgt   gccgtgccct   aagatgtgca   360
aaccaccagg   ttgcgaatgc   ccggcttcgg   aaggattcgt   tcgcaatgac   aaacacgaat   420
gtatcaagtt   cgacgactgc   cccaaataaa   ttcaataaat   cagtcttgtt   gataaataca   480
atcgtgatgc   tcacgttttt   ttttcttgcc   ataaaatcta   tacttcccaa   aaaaaaaaaa   540
aaaaaaaa         (SEQ ID                                                    548
                  NO: 25)
```

FIG. 13

```
Consensus (SEQ ID NO: 30) XXXXXXXXXXXXXXXXXXXXHRKCGPNEEWTECTGCEXKCGXGEXPCPMMCRPPSCECMAGKGLRRIXDGRCVPEAQCPKXMV
                                   10        20        30        40        50        60        70        80
                         ----+----+----+----+----+----+----+----+----+----+----+----+----+----+----+----+
        (SEQ ID NO:28)   -------------------- MERKCGPNEEWTECTGCEIKCGQGEQPCPMMCRPPSCECMAGKGLRRTADGRCVPEAQCPKRMV   64
        (SEQ ID NO:27)   MLPLIFLIAFIVGAAVAHRKCGPNEEWTECTGCEMKCGEGETPCPMMCRPPSCECMAGKQLARTPDGRCVPEAQCPKHMV   80

Consensus (SEQ ID NO: 30)
KRDEKCGXNEKFLKCRGCEGICKEGICKERLVPCPXMCKPPGCECPASEGFVRNDKXECIKFDDCPK
          90       100       110       120       130       140
 ----+----+----+----+----+----+----+----+----+----+----+----+----+
(SEQ ID NO: 28)   KRDEKCGPNEKELKCRGCEGTCKERLVPCPRMCKPPGCECPASEGFVRNDKGECIKEDDCPK        126
(SEQ ID NO: 27)   KRDEKCGKNEKFLKCRGCEGTCKERLVPCPKMCKPPGCECPASEGFVRNDKHECIKFDDCPK        142
```

FIG. 14

MGPESCGPNEVWTECTGCELKCGQDENTPCTLNCRPPSCECSPGRGMRRTNDGRCIPASQCP
QHRAKREEQCKPNEQWSPCRGCEGTCAQRFVPCTRNCRPPGCECVAGAGFVRDAEGNCIK
EDDCPK (SEQ ID NO: 21)

FIG. 18

```
6728N    MGP---ESCGPNEVWTECTGCELKCGQDENTPCTLNCRPPSCECSPGRGMRRTNDGRCIPASQCPQH 64  (SEQ ID NO: 37)
6728C    MRAKREEQCKPNEQWSPCRGCEGTCAQR-FVPCTRNCRPPGCECVAGAGEVRDAEGNCIKFDDCPK- 65  (SEQ ID NO: 38)
           *  .  ****  *. *   .*:  ****.****  .**** *****.**** . *: ** .:**:
```

FIG. 19

SEQUENCE LISTING

```
<160> NUMBER OF SEQ ID NOS: 38

<210> SEQ ID NO 1
<211> LENGTH: 1210
<212> TYPE: DNA
<213> ORGANISM: Trichuris vulpis

<400> SEQUENCE: 1
cattcactgc ggttgtaaaa gcagtgcaga aatgaggctg gtcttccatg cggttattta      60
cctcacattg gggttcctca ccgacgccgt aagagaaaaa cgtggcaaat gtcctcctga     120
accaccgatc gcaggaaaca cgatctactg ccgcgatgat tttgattgtg gaggaagaca     180
gaagtgctgt acaattgcag aaggacgtgg atgcgtgccg ccctatggtg aacaacattt     240
cgaagtggtg aaaccgggtc attgcccagc tattccagcg gttacgggca tggcgaactt     300
ctgtaacact gatggcgact gtgatggacc gaaaaaatgt tgtctcacat cgcgcggcta     360
cgattgcaca catccattac acttcccaat ccagccacaa cctccagtag acagtgccc      420 tccttcaaag ccccgtatcc caggaaaatg ggtagacatc tgcgctaagc atgccaactg     480
cccagaccca gagaagtgtt gcgacacgga gtatggcaac cgatgtatgg atgttggatt     540
agtgccagga caaggagaaa gaccaggcaa ttgcccgaac gaaccacgaa taagaggaac     600
taaatacgat tgccgacgag acgatgactg cgacggtgtg cagaaatgct gcttcactgt     660
tgagggacgt gagtgcgtgg aaccaagtag aaaaccactg gacaagcccg gacattgtcc     720
accaattccc gctgatgtgg gctcagccag gtactgcgac actgatcggg attgtgatgg     780
accaagaaaa tgctgcctct cttcgcgtgg ctatgaatgt aaacatccag tacactatcc     840
cgatcgagtg gagccactag taggagaatg cccaccatca cgacctcgca ttcctgggaa     900
atgggttgac atctgctcta agcatgccaa ctgcccagac ccagagaaat gttgcgacac     960
ggagtatggc aaccgatgta tggacgttgg attagtgcct ggacaaggag aaaaacctgc    1020
```

```
caactgccca aaggaaccac gaataagagg aactaagtac gactgtcgac gggacgatga      1080
ctgcgatggg aaacaaaagt gctgctacac aactgaaggc cgcgaatgcg tccatggtat      1140
atggccttaa atggttgctt cttcctataa taaaagcaaa cgaatcaaaa aaaaaaaaaa      1200
aaaaaaaaaa                                                            1210
```

<210> SEQ ID NO 2
<211> LENGTH: 1059
<212> TYPE: DNA
<213> ORGANISM: Trichuris vulpis

<400> SEQUENCE: 2

```
gtaagagaaa aacgtggcaa atgtcctcct gaaccaccga tcgcaggaaa cacgatctac       60
tgccgcgatg attttgattg tggaggaaga cagaagtgct gtacaattgc agaaggacgt      120
ggatgcgtgc cgccctatgg tgaacaagat ttcgaagtgg tgaaaccggg tcattgccca      180
gctattccag cggttacggg catggcgaac ttctgtaaca ctgatggcga ctgtgatgga      240
ccgaaaaaat gttgtctcac atcgcgcggc tacgattgta cacatccgtt acacttccca      300
atccagccac aacctccagt aggacagtgc cctccttcaa agccccgtgt tccaggaaaa      360
tgggtagaca tctgcgctaa gcatgccaat tgcccagacc cagagaagtg ttgcgacacg      420
gagtatggca accgatgtat ggatgttgga ttagtggcag acaaggagaa aagaccaggc      480
aattgcccga cgaaccacga ataagagga actaaatacg attgccgacg agacgatgac      540
tgcgacggtg tgcagaaatg ctgcttcact gttgagggac gtgagtgcgt ggaaccaagc      600
agaaaaccac tggacaagcc cggacattgt ccaccaattc ccgctgatgt gggctcagcc      660
aggtactgcg acactgatcg ggattgtgat ggaccaagaa aatgctgcct ctcttcgcgt      720
ggctatgaat gtaaacatcc agtacactat cccgatcgag tggagccact agtaggagaa      780
tgcccaccat cacgacctcg cattcctggg aaatggttg acatctgctc taagcatgcc       840
aactgcccag acccagagaa atgttgcgac acggagtatg caaccgatg tatggacgtt       900 ggattagtgc ctggacaagg agaaaaacct gccaactgcc caaaggaacc acgaataagg      960
ggaactaagt acgactgtcg acgggacgat gactgcgatg ggaaacaaaa gtgctgctac      1020
acaactgaag gccgcgaatg cgtccatggt atatggcct                            1059
```

<210> SEQ ID NO 3
<211> LENGTH: 372
<212> TYPE: PRT
<213> ORGANISM: Trichuris vulpis

<400> SEQUENCE: 3

```
Met Arg Leu Val Phe His Ala Val Ile Tyr Leu Thr Leu Gly Phe Leu
1               5                   10                  15

Thr Asp Ala Val Arg Glu Lys Arg Gly Lys Cys Pro Pro Glu Pro Pro
            20                  25                  30

Ile Ala Gly Asn Thr Ile Tyr Cys Arg Asp Asp Phe Asp Cys Gly Gly
        35                  40                  45

Arg Gln Lys Cys Cys Thr Ile Ala Glu Gly Arg Gly Cys Val Pro Pro
    50                  55                  60

Tyr Gly Glu Gln His Phe Glu Val Val Lys Pro Gly His Cys Pro Ala
65                  70                  75                  80

Ile Pro Ala Val Thr Gly Met Ala Asn Phe Cys Asn Thr Asp Gly Asp
                85                  90                  95

Cys Asp Gly Pro Lys Lys Cys Cys Leu Thr Ser Arg Gly Tyr Asp Cys
```

```
            100                 105                 110
Thr His Pro Leu His Phe Pro Ile Gln Pro Gln Pro Val Gly Gln
            115                 120                 125
Cys Pro Ser Lys Pro Arg Ile Pro Gly Lys Trp Val Asp Ile Cys
    130                 135                 140
Ala Lys His Ala Asn Cys Pro Asp Pro Glu Lys Cys Cys Asp Thr Glu
145                 150                 155                 160
Tyr Gly Asn Arg Cys Met Asp Val Gly Leu Val Pro Gly Gln Gly Glu
                165                 170                 175
Arg Pro Gly Asn Cys Pro Asn Glu Pro Arg Ile Arg Gly Thr Lys Tyr
            180                 185                 190
Asp Cys Arg Arg Asp Asp Cys Asp Gly Val Gln Lys Cys Cys Phe
        195                 200                 205
Thr Val Glu Gly Arg Glu Cys Val Glu Pro Ser Arg Lys Pro Leu Asp
    210                 215                 220
Lys Pro Gly His Cys Pro Pro Ile Pro Ala Asp Val Gly Ser Ala Arg
225                 230                 235                 240
Tyr Cys Asp Thr Asp Arg Asp Cys Asp Gly Pro Arg Lys Cys Cys Leu
                245                 250                 255
Ser Ser Arg Gly Tyr Glu Cys Lys His Pro Val His Tyr Pro Asp Arg
            260                 265                 270
Val Glu Pro Leu Val Gly Glu Cys Pro Pro Ser Arg Pro Arg Ile Pro
        275                 280                 285
Gly Lys Trp Val Asp Ile Cys Ser Lys His Ala Asn Cys Pro Asp Pro
    290                 295                 300
Glu Lys Cys Cys Asp Thr Glu Tyr Gly Asn Arg Cys Met Asp Val Gly
305                 310                 315                 320
Leu Val Pro Gly Gln Gly Glu Lys Pro Ala Asn Cys Pro Lys Glu Pro
                325                 330                 335
Arg Ile Arg Gly Thr Lys Tyr Asp Cys Arg Arg Asp Asp Cys Asp
            340                 345                 350
Gly Lys Gln Lys Cys Cys Tyr Thr Thr Glu Gly Arg Glu Cys Val His
            355                 360                 365
Gly Ile Trp Pro
        370

<210> SEQ ID NO 4
<211> LENGTH: 353
<212> TYPE: PRT
<213> ORGANISM: Trichuris vulpis

<400> SEQUENCE: 4

Val Arg Glu Lys Arg Gly Lys Cys Pro Pro Glu Pro Ile Ala Gly
1               5                   10                  15
Asn

Leu His Phe Pro Ile Gln Pro Gln Pro Pro Val Gly Gln Cys Pro Pro
            100                 105                 110

Ser Lys Pro Arg Val Pro Gly Lys Trp Val Asp Ile Cys Ala Lys His
            115                 120                 125

Ala Asn Cys Pro Asp Pro Glu Lys Cys Cys Asp Thr Glu Tyr Gly Asn
    130                 135                 140

Arg Cys Met Asp Val Gly Leu Val Ala Gly Gln Gly Glu Arg Pro Gly
145                 150                 155                 160

Asn Cys Pro Asn Glu Pro Arg Ile Arg Gly Thr Lys Tyr Asp Cys Arg
                165                 170                 175

Arg Asp Asp Asp Cys Asp Gly Val Gln Lys Cys Cys Phe Thr Val Glu
            180                 185                 190

Gly Arg Glu Cys Val Glu Pro Ser Arg Lys Pro Leu Asp Lys Pro Gly
        195                 200                 205

His Cys Pro Pro Ile Pro Ala Asp Val Gly Ser Ala Arg Tyr Cys Asp
    210                 215                 220

Thr Asp Arg Asp Cys Asp Gly Pro Arg Lys Cys Cys Leu Ser Ser Arg
225                 230                 235                 240

Gly Tyr Glu Cys Lys His Pro Val His Tyr Pro Asp Arg Val Glu Pro
                245                 250                 255

Leu Val Gly Glu Cys Pro Pro Ser Arg Pro Arg Ile Pro Gly Lys Trp
            260                 265                 270

Val Asp Ile Cys Ser Lys His Ala Asn Cys Pro Asp Pro Glu Lys Cys
        275                 280                 285

Cys Asp Thr Glu Tyr Gly Asn Arg Cys Met Asp Val Gly Leu Val Pro
    290                 295                 300

Gly Gln Gly Glu Lys Pro Ala Asn Cys Pro Lys Glu Pro Arg Ile Arg
305                 310                 315                 320

Gly Thr Lys Tyr Asp Cys Arg Arg Asp Asp Asp Cys Asp Gly Lys Gln
                325                 330                 335

Lys Cys Cys Tyr Thr Thr Glu Gly Arg Glu Cys Val His Gly Ile Trp
            340                 345                 350

Pro

<210> SEQ ID NO 5
<211> LENGTH: 354
<212> TYPE: PRT
<213> ORGANISM: Artificial
<220> FEATURE:
<223> OTHER INFORMATION: Synthetic

<400> SEQUENCE: 5

Met Val Arg Glu Lys Arg Gly Lys Cys Pro Pro Glu Pro Pro Ile Ala
1               5                   10                  15

Gly Asn Thr Ile Tyr Cys Arg Asp Asp Phe Asp Cys Gly Gly Arg Gln
            20                  25                  30

Lys Cys Cys Thr Ile Ala Glu Gly Arg Gly Cys Val Pro Pro Tyr Gly
        35                  40                  45

Glu Gln His Phe Glu Val Val Lys Pro Gly His Cys Pro Ala Ile Pro
    50                  55                  60

Ala Val Thr Gly Met Ala Asn Phe Cys Asn Thr Asp Gly Asp Cys Asp
65                  70                  75                  80

Gly Pro Lys Lys Cys Cys Leu Thr Ser Arg Gly Tyr Asp Cys Thr His
                85                  90                  95

Pro Leu His Phe Pro Ile Gln Pro Gln Pro Pro Val Gly Gln Cys Pro

```
                    100                 105                 110
Pro Ser Lys Pro Arg Ile Pro Gly Lys Trp Val Asp Ile Cys Ala Lys
        115                 120                 125

His Ala Asn Cys Pro Asp Pro Glu Lys Cys Cys Asp Thr Glu Tyr Gly
    130                 135                 140

Asn Arg Cys Met Asp Val Gly Leu Val Pro Gly Gln Gly Glu Arg Pro
145                 150                 155                 160

Gly Asn Cys Pro Asn Glu Pro Arg Ile Arg Gly Thr Lys Tyr Asp Cys
                165                 170                 175

Arg Arg Asp Asp Asp Cys Asp Gly Val Gln Lys Cys Cys Phe Thr Val
            180                 185                 190

Glu Gly Arg Glu Cys Val Glu Pro Ser Arg Lys Pro Leu Asp Lys Pro
        195                 200                 205

Gly His Cys Pro Pro Ile Pro Ala Asp Val Gly Ser Ala Arg Tyr Cys
    210                 215                 220

Asp Thr Asp Arg Asp Cys Asp Gly Pro Arg Lys Cys Cys Leu Ser Ser
225                 230                 235                 240

Arg Gly Tyr Glu Cys Lys His Pro Val His Tyr Pro Asp Arg Val Glu
                245                 250                 255

Pro Leu Val Gly Glu Cys Pro Pro Ser Arg Pro Arg Ile Pro Gly Lys
            260                 265                 270

Trp Val Asp Ile Cys Ser Lys His Ala Asn Cys Pro Asp Pro Glu Lys
        275                 280                 285

Cys Cys Asp Thr Glu Tyr Gly Asn Arg Cys Met Asp Val Gly Leu Val
    290                 295                 300

Pro Gly Gln Gly Glu Lys Pro Ala Asn Cys Pro Lys Glu Pro Arg Ile
305                 310                 315                 320

Arg Gly Thr Lys Tyr Asp Cys Arg Arg Asp Asp Asp Cys Asp Gly Lys
                325                 330                 335

Gln Lys Cys Cys Tyr Thr Thr Glu Gly Arg Glu Cys Val His Gly Ile
            340                 345                 350

Trp Pro

<210> SEQ ID NO 6
<211> LENGTH: 353
<212> TYPE: PRT
<213> ORGANISM: Artificial
<220> FEATURE:
<223> OTHER INFORMATION: Synthetic

<400> SEQUENCE: 6

Val Arg Glu Lys Arg Gly Lys Cys Pro Pro Glu Pro Pro Ile Ala Gly
1               5                   10                  15

Asn Thr Ile Tyr Cys Arg Asp Asp Phe Asp Cys Gly Gly Arg Gln Lys
                20                  25                  30

Cys Cys Thr Ile Ala Glu Gly Arg Gly Cys Val Pro Pro Tyr Gly Glu
            35                  40                  45

Gln His Phe Glu Val Val Lys Pro Gly His Cys Pro Ala Ile Pro Ala
        50                  55                  60

Val Thr Gly Met Ala Asn Phe Cys Asn Thr Asp Gly Asp Cys Asp Gly
65                  70                  75                  80

Pro Lys Lys Cys Cys Leu Thr Ser Arg Gly Tyr Asp Cys Thr His Pro
                85                  90                  95

Leu His Phe Pro Ile Gln Pro Gln Pro Pro Val Gly Gln Cys Pro Pro
            100                 105                 110
```

Ser Lys Pro Arg Ile Pro Gly Lys Trp Val Asp Ile Cys Ala Lys His
    115                 120                 125

Ala Asn Cys Pro Asp Pro Glu Lys Cys Cys Asp Thr Glu Tyr Gly Asn
130                 135                 140

Arg Cys Met Asp Val Gly Leu Val Pro Gly Gln Gly Glu Arg Pro Gly
145                 150                 155                 160

Asn Cys Pro Asn Glu Pro Arg Ile Arg Gly Thr Lys Tyr Asp Cys Arg
                165                 170                 175

Arg Asp Asp Asp Cys Asp Gly Val Gln Lys Cys Cys Phe Thr Val Glu
            180                 185                 190

Gly Arg Glu Cys Val Glu Pro Ser Arg Lys Pro Leu Asp Lys Pro Gly
        195                 200                 205

His Cys Pro Pro Ile Pro Ala Asp Val Gly Ser Ala Arg Tyr Cys Asp
    210                 215                 220

Thr Asp Arg Asp Cys Asp Gly Pro Arg Lys Cys Cys Leu Ser Ser Arg
225                 230                 235                 240

Gly Tyr Glu Cys Lys His Pro Val His Tyr Pro Asp Arg Val Glu Pro
                245                 250                 255

Leu Val Gly Glu Cys Pro Pro Ser Arg Pro Arg Ile Pro Gly Lys Trp
            260                 265                 270

Val Asp Ile Cys Ser Lys His Ala Asn Cys Pro Asp Pro Glu Lys Cys
        275                 280                 285

Cys Asp Thr Glu Tyr Gly Asn Arg Cys Met Asp Val Gly Leu Val Pro
    290                 295                 300

Gly Gln Gly Glu Lys Pro Ala Asn Cys Pro Lys Glu Pro Arg Ile Arg
305                 310                 315                 320

Gly Thr Lys Tyr Asp Cys Arg Arg Asp Asp Cys Asp Gly Lys Gln
                325                 330                 335

Lys Cys Cys Tyr Thr Thr Glu Gly Arg Glu Cys Val His Gly Ile Trp
            340                 345                 350

Pro

<210> SEQ ID NO 7
<211> LENGTH: 354
<212> TYPE: PRT
<213> ORGANISM: Artificial
<220> FEATURE:
<223> OTHER INFORMATION: Synthetic

<400> SEQUENCE: 7

Met Val Arg Glu Lys Arg Gly Lys Cys Pro Pro Glu Pro Pro Ile Ala
1               5                   10                  15

Gly Asn Thr Ile Tyr Cys Arg Asp Asp Phe Asp Cys Gly Gly Arg Gln
                20                  25                  30

Lys Cys Cys Thr Ile Ala Glu Gly Arg Gly Cys Val Pro Pro Tyr Gly
            35                  40                  45

Glu Gln Asp Phe Glu Val Val Lys Pro Gly His Cys Pro Ala Ile Pro
        50                  55                  60

Ala Val Thr Gly Met Ala Asn Phe Cys Asn Thr Asp Gly Asp Cys Asp
65                  70                  75                  80

Gly Pro Lys Lys Cys Cys Leu Thr Ser Arg Gly Tyr Asp Cys Thr His
                85                  90                  95

Pro Leu His Phe Pro Ile Gln Pro Gln Pro Pro Val Gly Gln Cys Pro
                100                 105                 110

```
Pro Ser Lys Pro Arg Val Pro Gly Lys Trp Val Asp Ile Cys Ala Lys
            115                 120                 125
His Ala Asn Cys Pro Asp Pro Glu Lys Cys Cys Asp Thr Glu Tyr Gly
        130                 135                 140
Asn Arg Cys Met Asp Val Gly Leu Val Ala Gly Gln Gly Glu Arg Pro
145                 150                 155                 160
Gly Asn Cys Pro Asn Glu Pro Arg Ile Arg Gly Thr Lys Tyr Asp Cys
                165                 170                 175
Arg Arg Asp Asp Asp Cys Asp Gly Val Gln Lys Cys Cys Phe Thr Val
                180                 185                 190
Glu Gly Arg Glu Cys Val Glu Pro Ser Arg Lys Pro Leu Asp Lys Pro
            195                 200                 205
Gly His Cys Pro Pro Ile Pro Ala Asp Val Gly Ser Ala Arg Tyr Cys
        210                 215                 220
Asp Thr Asp Arg Asp Cys Asp Gly Pro Arg Lys Cys Cys Leu Ser Ser
225                 230                 235                 240
Arg Gly Tyr Glu Cys Lys His Pro Val His Tyr Pro Asp Arg Val Glu
                245                 250                 255
Pro Leu Val Gly Glu Cys Pro Pro Ser Arg Pro Arg Ile Pro Gly Lys
            260                 265                 270
Trp Val Asp Ile Cys Ser Lys His Ala Asn Cys Pro Asp Pro Glu Lys
        275                 280                 285
Cys Cys Asp Thr Glu Tyr Gly Asn Arg Cys Met Asp Val Gly Leu Val
        290                 295                 300
Pro Gly Gln Gly Glu Lys Pro Ala Asn Cys Pro Lys Glu Pro Arg Ile
305                 310                 315                 320
Arg Gly Thr Lys Tyr Asp Cys Arg Arg Asp Asp Asp Cys Asp Gly Lys
                325                 330                 335
Gln Lys Cys Cys Tyr Thr Thr Glu Gly Arg Glu Cys Val His Gly Ile
                340                 345                 350
Trp Pro

<210> SEQ ID NO 8
<211> LENGTH: 353
<212> TYPE: PRT
<213> ORGANISM: Artificial
<220> FEATURE:
<223> OTHER INFORMATION: Synthetic

<400> SEQUENCE: 8

Val Arg Glu Lys Arg Gly Lys Cys Pro Pro Glu Pro Ile Ala Gly
1               5                   10                  15
Asn Thr Ile Tyr Cys Arg Asp Asp Phe Asp Cys Gly Gly Arg Gln Lys
            20                  25                  30
Cys Cys Thr Ile Ala Glu Gly Arg Gly Cys Val Pro Pro Tyr Gly Glu
        35                  40                  45
Gln Asp Phe Glu Val Val Lys Pro Gly His Cys Pro Ala Ile Pro Ala
    50                  55                  60
Val Thr Gly Met Ala Asn Phe Cys Asn Thr Asp Gly Asp Cys Asp Gly
65                  70                  75                  80
Pro Lys Lys Cys Cys Leu Thr Ser Arg Gly Tyr Asp Cys Thr His Pro
                85                  90                  95
Leu His Phe Pro Ile Gln Pro Gln Pro Val Gly Gln Cys Pro Pro
            100                 105                 110
Ser Lys Pro Arg Val Pro Gly Lys Trp Val Asp Ile Cys Ala Lys His
```

```
                115                 120                 125
Ala Asn Cys Pro Asp Pro Glu Lys Cys Cys Asp Thr Glu Tyr Gly Asn
    130                 135                 140

Arg Cys Met Asp Val Gly Leu Val Ala Gly Gln Gly Glu Arg Pro Gly
145                 150                 155                 160

Asn Cys Pro Asn Glu Pro Arg Ile Arg Gly Thr Lys Tyr Asp Cys Arg
                165                 170                 175

Arg Asp Asp Asp Cys Asp Gly Val Gln Lys Cys Cys Phe Thr Val Glu
            180                 185                 190

Gly Arg Glu Cys Val Glu Pro Ser Arg Lys Pro Leu Asp Lys Pro Gly
        195                 200                 205

His Cys Pro Pro Ile Pro Ala Asp Val Gly Ser Ala Arg Tyr Cys Asp
    210                 215                 220

Thr Asp Arg Asp Cys Asp Gly Pro Arg Lys Cys Cys Leu Ser Ser Arg
225                 230                 235                 240

Gly Tyr Glu Cys Lys His Pro Val His Tyr Pro Asp Arg Val Glu Pro
                245                 250                 255

Leu Val Gly Glu Cys Pro Pro Ser Arg Pro Arg Ile Pro Gly Lys Trp
            260                 265                 270

Val Asp Ile Cys Ser Lys His Ala Asn Cys Pro Asp Pro Glu Lys Cys
        275                 280                 285

Cys Asp Thr Glu Tyr Gly Asn Arg Cys Met Asp Val Gly Leu Val Pro
    290                 295                 300

Gly Gln Gly Glu Lys Pro Ala Asn Cys Pro Lys Glu Pro Arg Ile Arg
305                 310                 315                 320

Gly Thr Lys Tyr Asp Cys Arg Arg Asp Asp Cys Asp Gly Lys Gln
                325                 330                 335

Lys Cys Cys Tyr Thr Thr Glu Gly Arg Glu Cys Val His Gly Ile Trp
            340                 345                 350

Pro

<210> SEQ ID NO 9
<211> LENGTH: 369
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(19)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid

<400> SEQUENCE: 9

Xaa Xaa Xaa Xaa Xaa Xaa Xaa Xaa Xaa Xaa Xaa Xaa Xaa Xaa Xaa Xaa
1               5                   10                  15

Xaa Xaa Xaa Val Arg Glu Lys Arg Gly Lys Cys Pro Pro Glu Pro Pro
            20                  25                  30

Ile Ala Gly Asn Thr Ile Tyr Cys Arg Asp Asp Glu Asp Cys Gly Gly
```

```
            35                  40                  45
Arg Gln Lys Cys Cys Thr Ile Ala Glu Gly Arg Gly Cys Val Pro Pro
    50                  55                  60
Tyr Gly Glu Gln Xaa Phe Glu Val Val Lys Pro Gly His Cys Pro Ala
65                  70                  75                  80
Ile Pro Ala Val Thr Gly Met Ala Asn Glu Cys Asn Ile Asp Gly Asp
                85                  90                  95
Cys Asp Gly Met Cys Cys Leu Ile Ser Arg Gly Tyr Asp Cys Thr His
                100                 105                 110
Pro Leu His Glu Thr Ile Gln Pro Gln Pro Val Gly Gln Cys Pro
            115                 120                 125
Pro Ser Lys Pro Arg Xaa Pro Gly Lys Trp Val Asp Ile Cys Ala Lys
    130                 135                 140
His Ala Asn Cys Pro Asp Pro Glu Lys Cys Cys Asp Thr Glu Tyr Gly
145                 150                 155                 160
Asn Arg Cys Met Asp Val Gly Leu Val Xaa Gly Gly Glu Arg Pro Gly
                165                 170                 175
Asn Cys Pro Asn Glu Pro Arg Ile Arg Gly Ile Lys Tyr Asp Cys Arg
                180                 185                 190
Arg Asp Asp Asp Cys Asp Gly Val Gln Lys Cys Cys Glu Thr Val Glu
            195                 200                 205
Gly Arg Glu Cys Val Pro Ser Arg Lys Pro Leu Asp Lys Pro Gly
    210                 215                 220
His Cys Pro Pro Ile Pro Ala Asp Val Gly Ser Ala Arg Tyr Cys Asp
225                 230                 235                 240
Thr Asp Arg Asp Cys Asp Gly Pro Arg Lys Cys Cys Leu Ser Ser Arg
                245                 250                 255
Gly Tyr Glu Cys Lys His Pro Val His Tyr Pro Asp Arg Val Glu Pro
                260                 265                 270
Leu Val Gly Glu Cys Pro Pro Ser Arg Pro Arg Ile Pro Gly Lys Trp
    275                 280                 285
Val Asp Ile Cys Ser Lys His Ala Asn Cys Pro Asp Pro Glu Lys Cys
290                 295                 300
Cys Asp Thr Glu Tyr Gly Asn Arg Cys Met Asp Val Gly Leu Val Pro
305                 310                 315                 320
Gly Gln Gly Glu Lys Pro Ala Asn Cys Pro Lys Glu Pro Arg Ile Arg
                325                 330                 335
Gly Thr Lys Tyr Asp Cys Arg Arg Asp Asp Asp Cys Asp Gly Lys Gln
                340                 345                 350
Lys Cys Cys Tyr Thr Thr Glu Gly Arg Glu Cys Val His Gly Ile Trp
    355                 360                 365
Pro

<210> SEQ ID NO 10
<211> LENGTH: 865
<212> TYPE: DNA
<213> ORGANISM: Toxocara canis

<400> SEQUENCE: 10
caagaagatt tatggtgtgg cagcttcgag acgaaggagg catcacttca cgctcgaaaa    60
cagtctggac acccacctga aatggcttag ccacgagcaa aggaggaac tgctgcaaat    120 gaagaaggac ggcaaatcga agaaggagct ccaggataag atcatgcact attacgagca    180
cctcgaaggc gatgcgaaac atgaagcaac agagcaactg aagggcggat gccgcgagat    240
```

```
tcttaagcat gttgttggcg aggagaaagc agctgagatc aaagcactga aagattctgg      300
agcaagcaaa gatgagctta aagccaaggt cgaagaggca ctccacgcag tcaccgacga      360
agaaaagaag caacatatcg ccgaattcgg tcccgcatgc aagaagattt atggtgtggc      420
agcttcgaga cgaaggaggc atcacttcac gctcgaaaac agtctggaca cccacctgaa      480
atggcttagc cacgagcaaa aggaggaact gctgcaaatg aagaaggacg gcaaatcgaa      540
gaaggagctc caggataaga tcatgcacta ttacgagcac ctcgaaggga tgctcctcgc      600
gctatgtatc ctgtattgac ggccttccaa cctatcacac tgtcagtgc ggccttacat       660 tcgacgagcg tagaaagacc tgtcttccta agcagctggt aaagtactgc ggaatcccag      720
aatctggaga ggcgtcggcg gaagttggtg agtcgtacta acacagcacg ctctcgttgg      780
tgcagatgtt gtgtgaaata cttttgtcag ttttccgtgt gttttaaata aataaaaaat      840
tccgtaaaaa aaaaaaaaaa aaaaa                                            865

<210> SEQ ID NO 11
<211> LENGTH: 632
<212> TYPE: DNA
<213> ORGANISM: Toxocara cati

<400> SEQUENCE: 11
atttatggtg tggcagcttc gagacgaagg aggcatcact tcacgctcga aaaagtctg        60 gacacccacc tgaaatggct tagccacgag caaaaggagg aactgctgaa atgaagaaa       120 gatgggaaat cgaagaagga gctccaggat aaggtgatgc acttctacga gcacctcgaa      180
ggcgatgcga acatgaagc aacagagcaa ctgaagggcg atgccgcga gatccttaag       240 catgttgttg gtgaggagaa agcagctgag atcaaagcac tgaaagattc tggagcaagc      300
aaagatgagc ttaaagccaa ggtcgaagat gcactccacg cggtcaccga agaagaaaag      360
aagcaacata tcgccgaatt tggtccagca tgcaaggaaa ttttcggggt gccggttgat      420
gttcgtcaca acgcgaccc ttatactaat atgacgcccg atgaagttgc tgaaggacta       480
agaagttaac ggtgatcgag cttttgcaa aaactggttg atgcttttaa attcttttaa       540
gcctttttct tgtgttattt cggaattgta ccacacgaac agttagttcc gaataaagaa      600
ctgtaattat gtaaaaaaaa aaaaaaaaaa aa                                    632

<210> SEQ ID NO 12
<211> LENGTH: 205
<212> TYPE: PRT
<213> ORGANISM: Toxocara canis

<400> SEQUENCE: 12

Lys Lys Ile Tyr Gly Val Ala Ala Ser Arg Arg Arg His His Phe
1               5                   10                  15

Thr Leu Glu Asn Ser Leu Asp Thr His Leu Lys Trp Leu Ser His Glu
            20                  25                  30

Gln Lys Glu Glu Leu Leu Gln Met Lys Lys Asp Gly Lys Ser Lys Lys
        35                  40                  45

Glu Leu Gln Asp Lys Ile Met His Tyr Tyr Glu His Leu Glu Gly Asp
    50                  55                  60

Ala Lys His Glu Ala Thr Glu Gln Leu Lys Gly Gly Cys Arg Glu Ile
65                  70                  75                  80

Leu Lys His Val Val Gly Glu Glu Lys Ala Ala Glu Ile Lys Ala Leu
                85                  90                  95
```

```
Lys Asp Ser Gly Ala Ser Lys Asp Glu Leu Lys Ala Lys Val Glu Glu
                100                 105                 110

Ala Leu His Ala Val Thr Asp Glu Glu Lys Lys Gln His Ile Ala Glu
            115                 120                 125

Phe Gly Pro Ala Cys Lys Lys Ile Tyr Gly Val Ala Ala Ser Arg Arg
        130                 135                 140

Arg Arg His His Phe Thr Leu Glu Asn Ser Leu Asp Thr His Leu Lys
145                 150                 155                 160

Trp Leu Ser His Glu Gln Lys Glu Glu Leu Leu Gln Met Lys Lys Asp
                165                 170                 175

Gly Lys Ser Lys Lys Glu Leu Gln Asp Lys Ile Met His Tyr Tyr Glu
            180                 185                 190

His Leu Glu Gly Met Leu Leu Ala Leu Cys Ile Leu Tyr
        195                 200                 205

<210> SEQ ID NO 13
<211> LENGTH: 162
<212> TYPE: PRT
<213> ORGANISM: Toxocara cati

<400> SEQUENCE: 13

Ile Tyr Gly Val Ala Ala Ser Arg Arg Arg Arg His His Phe Thr Leu
1               5                   10                  15

Glu Lys Ser Leu Asp Thr His Leu Lys Trp Leu Ser His Glu Gln Lys
            20                  25                  30

Glu Glu Leu Leu Lys Met Lys Lys Asp Gly Lys Ser Lys Lys Glu Leu
        35                  40                  45

Gln Asp Lys Val Met His Phe Tyr Glu His Leu Glu Gly Asp Ala Lys
    50                  55                  60

His Glu Ala Thr Glu Gln Leu Lys Gly Gly Cys Arg Glu Ile Leu Lys
65                  70                  75                  80

His Val Val Gly Glu Glu Lys Ala Ala Glu Ile Lys Ala Leu Lys Asp
                85                  90                  95

Ser Gly Ala Ser Lys Asp Glu Leu Lys Ala Lys Val Glu Asp Ala Leu
            100                 105                 110

His Ala Val Thr Asp Glu Glu Lys Lys Gln His Ile Ala Glu Phe Gly
        115                 120                 125

Pro Ala Cys Lys Glu Ile Phe Gly Val Pro Ile Asp Val Arg His Lys
    130                 135                 140

Arg Asp Pro Tyr Thr Asn Met Thr Pro Asp Glu Val Ala Glu Gly Leu
145                 150                 155                 160

Arg Ser

<210> SEQ ID NO 14
<211> LENGTH: 130
<212> TYPE: PRT
<213> ORGANISM: Artificial
<220> FEATURE:
<223> OTHER INFORMATION: Synthetic

<400> SEQUENCE: 14

Met His His Phe Thr Leu Glu Asn Ser Leu Asp Thr His Leu Lys Trp
1               5                   10                  15

Leu Ser His Glu Gln Lys Glu Glu Leu Leu Gln Met Lys Lys Asp Gly
            20                  25                  30

Lys Ser Lys Lys Glu Leu Gln Asp Lys Ile Met His Tyr Tyr Glu His
        35                  40                  45
```

```
Leu Glu Gly Asp Ala Lys His Glu Ala Thr Glu Gln Leu Lys Gly Gly
         50                  55                  60

Cys Arg Glu Ile Leu Lys His Val Val Gly Glu Lys Ala Ala Glu
 65                  70                  75                  80

Ile Lys Ala Leu Lys Asp Ser Gly Ala Ser Lys Asp Glu Leu Lys Ala
                 85                  90                  95

Lys Val Glu Glu Ala Leu His Ala Val Thr Asp Glu Glu Lys Lys Gln
                100                 105                 110

His Ile Ala Glu Phe Gly Pro Ala Cys Lys Lys Ile Tyr Gly Val Ala
            115                 120                 125

Ala Ser
    130

<210> SEQ ID NO 15
<211> LENGTH: 129
<212> TYPE: PRT
<213> ORGANISM: Artificial
<220> FEATURE:
<223> OTHER INFORMATION: Synthetic

<400> SEQUENCE: 15

His His Phe Thr Leu Glu Asn Ser Leu Asp Thr His Leu Lys Trp Leu
  1               5                  10                  15

Ser His Glu Gln Lys Glu Leu Leu Gln Met Lys Lys Asp Gly Lys
                 20                  25                  30

Ser Lys Lys Glu Leu Gln Asp Lys Ile Met His Tyr Tyr Glu His Leu
             35                  40                  45

Glu Gly Asp Ala Lys His Glu Ala Thr Glu Gln Leu Lys Gly Gly Cys
 50                  55                  60

Arg Glu Ile Leu Lys His Val Val Gly Glu Lys Ala Ala Glu Ile
 65                  70                  75                  80

Lys Ala Leu Lys Asp Ser Gly Ala Ser Lys Asp Glu Leu Lys Ala Lys
                 85                  90                  95

Val Glu Glu Ala Leu His Ala Val Thr Asp Glu Glu Lys Lys Gln His
                100                 105                 110

Ile Ala Glu Phe Gly Pro Ala Cys Lys Lys Ile Tyr Gly Val Ala Ala
            115                 120                 125

Ser

<210> SEQ ID NO 16
<211> LENGTH: 155
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
```

```
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (138)..(155)
<223> OTHER INFORMATION: Xaa can be any naturally occurring amino acid

<400> SEQUENCE: 16

Xaa Xaa Xaa Xaa Xaa Xaa Xaa Xaa Xaa Xaa Xaa His His Phe Thr Leu
1               5                   10                  15

Glu Xaa Ser Leu Asp Thr His Leu Lys Trp Leu Ser His Glu Gln Lys
            20                  25                  30

Glu Glu Leu Leu Xaa Met Lys Lys Asp Gly Lys Ser Lys Lys Glu Leu
        35                  40                  45

Gln Asp Lys Xaa Met His Xaa Tyr Glu His Leu Glu Gly Asp Ala Lys
    50                  55                  60

His Glu Ala Thr Glu Gln Leu Lys Gly Gly Cys Arg Glu Ile Leu Lys
65                  70                  75                  80

His Val Val Gly Glu Glu Lys Ala Ala Glu Ile Phe Ala Leu Lys Asp
                85                  90                  95

Ser Gly Ala Ser Lys Asp Glu Leu Lys Ala Lys Val Glu Xaa Ala Leu
            100                 105                 110

His Ala Val Thr Asp Glu Glu Lys Lys Gln His Ile Ala Glu Phe Gly
        115                 120                 125

Phe Ala Cys Lys Xaa Ile Xaa Gly Val Xaa Xaa Xaa Xaa Xaa Xaa Xaa
    130                 135                 140

Xaa Xaa Xaa Xaa Xaa Xaa Xaa Xaa Xaa Xaa Xaa
145                 150                 155

<210> SEQ ID NO 17
<211> LENGTH: 535
<212> TYPE: DNA
<213> ORGANISM: Toxocara canis

<400> SEQUENCE: 17
agtcagtagc cactttaatc catcagaatg ctctctgttc ttgcgctttt cgctcttatt      60
acttttgctg tggccggtcc ggaaagctgc ggtccaaacg aagtgtggac tgaatgtacc     120
ggttgcgaat tgaaatgtgg gcaagatgaa aatacgccgt gcacactaaa ctgtcgaccg     180
ccgtgatgtg agtgctctcc aggaagaggc atgagacgaa ccaacgatgg aaggtgcatt     240
ccggctagtc agtgcccgca acacagggcc aagagagagg agcaatgcaa gccaaatgag     300
cagtggtcac cgtgccgagg atgtgaagga acatgcgcac aaagatttgt cccttgcact     360
agaaactgcc gaccaccagg ctgtgaatgc gttgctggcg caggtttcgt acgtgacgct     420
gaaggaaact gcatcaagtt cgacgattgc ccgaagtaaa taataaccat acaaattgct     480
gattccaatt aaaataataa atgagtccag ctgttaaaaa aaaaaaaaa aaaaa           535
```

<210> SEQ ID NO 18
<211> LENGTH: 536
<212> TYPE: DNA
<213> ORGANISM: Toxocara cati

<400> SEQUENCE: 18

```
cagtcagcag ctactttat ccatcggaat gctctctgtt cttgcgcttt tcgctcttat      60
tactttcgct gtggccgatc cgaaaagttg cggtccaaac gaagtgtgga ctgaatgtac     120
cggttgcgag ttgaaatgcg ggcaggatga ggatacgccg tgcacactaa actgtcggcc    180
gccgtcatgt gagtgctcac caggaagagg catgagacga accgacgatg ggaggtgcat    240
tccggctagt cagtgcccgc aacacagagc caagagagag gagcagtgca agccaaatga    300
gcagtggtca ccgtgccgag gatgtgaagg aacatgcgca caagatttg tcccttgcac     360
tagaaactgc cgaccaccag gatgtgaatg cgttgctggc gcaggtttcg tacgtgacgc    420
tgcaggaaat tgcatcaagt tcgacgattg cccgaagtaa ataataacca tactaattgc    480
tgattacaat taaataata aatgagtcca gctgttaaaa aaaaaaaaaa aaaaaa        536
```

<210> SEQ ID NO 19
<211> LENGTH: 143
<212> TYPE: PRT
<213> ORGANISM: Toxocara canis

<400> SEQUENCE: 19

Met Leu Ser Val Leu Ala Leu Phe Ala Leu Ile Thr Phe Ala Val Ala
1               5                   10                  15

Gly Pro Glu Ser Cys Gly Pro Asn Glu Val Trp Thr Glu Cys Thr Gly
            20                  25                  30

Cys Glu Leu Lys Cys Gly Gln Asp Glu Asn Thr Pro Cys Thr Leu Asn
        35                  40                  45

Cys Arg Pro Pro Ser Cys Glu Cys Ser Pro Gly Arg Gly Met Arg Arg
    50                  55                  60

Thr Asn Asp Gly Arg Cys Ile Pro Ala Ser Gln Cys Pro Gln His Arg
65                  70                  75                  80

Ala Lys Arg Glu Glu Gln Cys Lys Pro Asn Glu Gln Trp Ser Pro Cys
                85                  90                  95

Arg Gly Cys Glu Gly Thr Cys Ala Gln Arg Phe Val Pro Cys Thr Arg
            100                 105                 110

Asn Cys Arg Pro Pro Gly Cys Glu Cys Val Ala Gly Ala Gly Phe Val
        115                 120                 125

Arg Asp Ala Glu Gly Asn Cys Ile Lys Phe Asp Asp Cys Pro Lys
    130                 135                 140

<210> SEQ ID NO 20
<211> LENGTH: 143
<212> TYPE: PRT
<213> ORGANISM: Toxocara cati

<400> SEQUENCE: 20

Met Leu Ser Val Leu Ala Leu Phe Ala Leu Ile Thr Phe Ala Val Ala
1               5                   10                  15

Asp Pro Lys Ser Cys Gly Pro Asn Glu Val Trp Thr Glu Cys Thr Gly
            20                  25                  30

Cys Glu Leu Lys Cys Gly Gln Asp Glu Asp Thr Pro Cys Thr Leu Asn
        35                  40                  45

Cys Arg Pro Pro Ser Cys Glu Cys Ser Pro Gly Arg Gly Met Arg Arg
    50                  55                  60

Thr Asp Asp Gly Arg Cys Ile Pro Ala Ser Gln Cys Pro Gln His Arg
65                  70                  75                  80

Ala Lys Arg Glu Glu Gln Cys Lys Pro Asn Glu Gln Trp Ser Pro Cys
                85                  90                  95

Arg Gly Cys Glu Gly Thr Cys Ala Gln Arg Phe Val Pro Cys Thr Arg
            100                 105                 110

Asn Cys Arg Pro Pro Gly Cys Glu Cys Val Ala Gly Ala Gly Phe Val
        115                 120                 125

Arg Asp Ala Ala Gly Asn Cys Ile Lys Phe Asp Asp Cys Pro Lys
130                 135                 140

<210> SEQ ID NO 21
<211> LENGTH: 128
<212> TYPE: PRT
<213> ORGANISM: Artificial
<220> FEATURE:
<223> OTHER INFORMATION: Synthetic

<400> SEQUENCE: 21

Met Gly Pro Glu Ser Cys Gly Pro Asn Glu Val Trp Thr Glu Cys Thr
1               5                   10                  15

Gly Cys Glu Leu Lys Cys Gly Gln Asp Glu Asn Thr Pro Cys Thr Leu
                20                  25                  30

Asn Cys Arg Pro Pro Ser Cys Glu Cys Ser Pro Gly Arg Gly Met Arg
            35                  40                  45

Arg Thr Asn Asp Gly Arg Cys Ile Pro Ala Ser Gln Cys Pro Gln His
        50                  55                  60

Arg Ala Lys Arg Glu Glu Gln Cys Lys Pro Asn Glu Gln Trp Ser Pro
65                  70                  75                  80

Cys Arg Gly Cys Glu Gly Thr Cys Ala Gln Arg Phe Val Pro Cys Thr
                85                  90                  95

Arg Asn Cys Arg Pro Pro Gly Cys Glu Cys Val Ala Gly Ala Gly Phe
            100                 105                 110

Val Arg Asp Ala Glu Gly Asn Cys Ile Lys Phe Asp Asp Cys Pro Lys
        115                 120                 125

<210> SEQ ID NO 22
<211> LENGTH: 127
<212> TYPE: PRT
<213> ORGANISM: Artificial
<220> FEATURE:
<223> OTHER INFORMATION: Synthetic

<400> SEQUENCE: 22

Gly Pro Glu Ser Cys Gly Pro Asn Glu Val Trp Thr Glu Cys Thr Gly
1               5                   10                  15

Cys Glu Leu Lys Cys Gly Gln Asp Glu Asn Thr Pro Cys Thr Leu Asn
                20                  25                  30

Cys Arg Pro Pro Ser Cys Glu Cys Ser Pro Gly Arg Gly Met Arg Arg
            35                  40                  45

Thr Asn Asp Gly Arg Cys Ile Pro Ala Ser Gln Cys Pro Gln His Arg
        50                  55                  60

Ala Lys Arg Glu Glu Gln Cys Lys Pro Asn Glu Gln Trp Ser Pro Cys
65                  70                  75                  80

Arg Gly Cys Glu Gly Thr Cys Ala Gln Arg Phe Val Pro Cys Thr Arg
                85                  90                  95

Asn Cys Arg Pro Pro Gly Cys Glu Cys Val Ala Gly Ala Gly Phe Val

```
                    100                 105                 110
Arg Asp Ala Glu Gly Asn Cys Ile Lys Phe Asp Asp Cys Pro Lys
            115                 120                 125

<210> SEQ ID NO 23
<211> LENGTH: 143
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid

<400> SEQUENCE: 23

Xaa Xaa Xaa Xaa Xaa Xaa Xaa Xaa Xaa Xaa Xaa Xaa Xaa Xaa Xaa
1               5                   10                  15

Xaa Pro Xaa Ser Cys Gly Pro Asn Glu Val Trp Thr Glu Cys Thr Gly
            20                  25                  30

Cys Glu Leu Lys Cys Gly Gln Asp Glu Xaa Thr Pro Cys Thr Leu Asn
            35                  40                  45

Cys Arg Pro Pro Ser Cys Glu Cys Ser Pro Gly Arg Gly Met Arg Arg
        50                  55                  60

Thr Xaa Asp Gly Arg Cys Ile Pro Ala Ser Gln Cys Pro Gln His Arg
65                  70                  75                  80

Ala Lys Arg Glu Glu Gln Cys Lys Pro Asn Glu Gln Trp Ser Pro Cys
                85                  90                  95

Arg Gly Cys Glu Gly Thr Cys Ala Gln Arg Phe Val Pro Cys Thr Arg
            100                 105                 110

Asn Cys Arg Pro Pro Gly Cys Glu Cys Val Ala Gly Ala Gly Phe Val
            115                 120                 125

Arg Asp Ala Xaa Gly Asn Cys Ile Lys Phe Asp Asp Cys Pro Lys
        130                 135                 140

<210> SEQ ID NO 24
<211> LENGTH: 469
<212> TYPE: DNA
<213> ORGANISM: Toxocara canis

<400> SEQUENCE: 24
atcagcaggt tcgcttcaa  atgcttccga  taacttttt   gctggcaatt  attgtcggtg     60
cagcagtagc tcaccgtaaa tgtggtccaa  acgaagagtg  gaccgaatgc  actggttgcg    120
aaattaagtg cggtcaagga gagcaaccat  gccctatgat  gtgtcgtccg  ccatcgtgtg    180
aatgcatggc cggcaaagga ttacgaagaa  cagcggacgg  aagatgcgtg  ccggaggcac    240
aatgcccaaa aagaatggta aagcgagacg  aaaaatgtgg  gccaaacgag  aaattcctga    300
```

```
agtgcagagg ttgtgagggt acctgcaaag aacgtctcgt tccctgccct agaatgtgca    360
aaccaccagg ttgcgaatgc cccgcttcag aaggattcgt tcgcaatgac aaaggcgaat    420
gtatcaagtt cgacgactgc ccgaaataaa ttcaataaat caattttgt                469
```

<210> SEQ ID NO 25
<211> LENGTH: 548
<212> TYPE: DNA
<213> ORGANISM: Toxocara cati

<400> SEQUENCE: 25

```
atcagcaggt ttcgcttcaa atgcttccgt taacttttt gctggcattt attgtgggtg     60
cagcggtagc tcaccgtaaa tgtggtccaa atgaagagtg gacggaatgc actggctgcg    120
aaatgaagtg cggtgaagga gagacaccat gccctatgat gtgtcgtccg ccatcgtgtg    180
aatgcatggc cggcaaagga ttacgaagaa caccggacgg aagatgtgtg ccggaggcac    240
aatgcccgaa acatatggta aagcgagatg aaaaatgtgg aaaaacgag aaattcctga    300 agtgcagagg atgtgagggt acgtgcaaag aacgtctcgt gccgtgccct aagatgtgca    360
aaccaccagg ttgcgaatgc ccggcttcgg aaggattcgt tcgcaatgac aaacacgaat    420
gtatcaagtt cgacgactgc cccaaataaa ttcaataaat cagtcttgtt gataaataca    480
atcgtgatgc tcacgttttt ttttcttgcc ataaaatcta tacttcccaa aaaaaaaaa    540 aaaaaaaa                                                            548
```

<210> SEQ ID NO 26
<211> LENGTH: 142
<212> TYPE: PRT
<213> ORGANISM: Toxocara canis

<400> SEQUENCE: 26

Met Leu Pro Ile Thr Phe Leu Leu Ala Ile Ile Val Gly Ala Ala Val
1               5                   10                  15

Ala His Arg Lys Cys Gly Pro Asn Glu Glu Trp Thr Glu Cys Thr Gly
            20                  25                  30

Cys Glu Ile Lys Cys Gly Gln Gly Glu Gln Pro Cys Pro Met Met Cys
        35                  40                  45

Arg Pro Pro Ser Cys Glu Cys Met Ala Gly Lys Gly Leu Arg Arg Thr
    50                  55                  60

Ala Asp Gly Arg Cys Val Pro Glu Ala Gln Cys Pro Lys Arg Met Val
65                  70                  75                  80

Lys Arg Asp Glu Lys Cys Gly Pro Asn Glu Lys Phe Leu Lys Cys Arg
                85                  90                  95

Gly Cys Glu Gly Thr Cys Lys Glu Arg Leu Val Pro Cys Pro Arg Met
            100                 105                 110

Cys Lys Pro Pro Gly Cys Glu Cys Pro Ala Ser Glu Gly Phe Val Arg
        115                 120                 125

Asn Asp Lys Gly Glu Cys Ile Lys Phe Asp Asp Cys Pro Lys
    130                 135                 140

<210> SEQ ID NO 27
<211> LENGTH: 142
<212> TYPE: PRT
<213> ORGANISM: Toxocara cati

<400> SEQUENCE: 27

Met Leu Pro Leu Thr Phe Leu Leu Ala Phe Ile Val Gly Ala Ala Val

```
            1               5                  10                 15
          Ala His Arg Lys Cys Gly Pro Asn Glu Glu Trp Thr Glu Cys Thr Gly
                        20                 25                 30

Cys Glu Met Lys Cys Gly Glu Gly Glu Thr Pro Cys Pro Met Met Cys
                        35                 40                 45

Arg Pro Pro Ser Cys Glu Cys Met Ala Gly Lys Gly Leu Arg Arg Thr
                     50                 55                 60

Pro Asp Gly Arg Cys Val Pro Glu Ala Gln Cys Pro Lys His Met Val
           65                 70                 75                 80

Lys Arg Asp Glu Lys Cys Gly Lys Asn Glu Lys Phe Leu Lys Cys Arg
                           85                 90                 95

Gly Cys Glu Gly Thr Cys Lys Glu Arg Leu Val Pro Cys Pro Lys Met
                          100                105                110

Cys Lys Pro Pro Gly Cys Glu Cys Pro Ala Ser Glu Gly Phe Val Arg
                          115                120                125

Asn Asp Lys His Glu Cys Ile Lys Phe Asp Asp Cys Pro Lys
                          130                135                140
```

<210> SEQ ID NO 28
<211> LENGTH: 126
<212> TYPE: PRT
<213> ORGANISM: Artificial
<220> FEATURE:
<223> OTHER INFORMATION: Synthetic

<400> SEQUENCE: 28

```
          Met His Arg Lys Cys Gly Pro Asn Glu Glu Trp Thr Glu Cys Thr Gly
           1               5                  10                 15

Cys Glu Ile Lys Cys Gly Gln Gly Glu Gln Pro Cys Pro Met Met Cys
                        20                 25                 30

Arg Pro Pro Ser Cys Glu Cys Met Ala Gly Lys Gly Leu Arg Arg Thr
                        35                 40                 45

Ala Asp Gly Arg Cys Val Pro Glu Ala Gln Cys Pro Lys Arg Met Val
                     50                 55                 60

Lys Arg Asp Glu Lys Cys Gly Pro Asn Glu Lys Phe Leu Lys Cys Arg
           65                 70                 75                 80

Gly Cys Glu Gly Thr Cys Lys Glu Arg Leu Val Pro Cys Pro Arg Met
                           85                 90                 95

Cys Lys Pro Pro Gly Cys Glu Cys Pro Ala Ser Glu Gly Phe Val Arg
                          100                105                110

Asn Asp Lys Gly Glu Cys Ile Lys Phe Asp Asp Cys Pro Lys
                          115                120                125
```

<210> SEQ ID NO 29
<211> LENGTH: 125
<212> TYPE: PRT
<213> ORGANISM: Artificial
<220> FEATURE:
<223> OTHER INFORMATION: Synthetic

<400> SEQUENCE: 29

```
          His Arg Lys Cys Gly Pro Asn Glu Glu Trp Thr Glu Cys Thr Gly Cys
           1               5                  10                 15

Glu Ile Lys Cys Gly Gln Gly Glu Gln Pro Cys Pro Met Met Cys Arg
                        20                 25                 30

Pro Pro Ser Cys Glu Cys Met Ala Gly Lys Gly Leu Arg Arg Thr Ala
                        35                 40                 45
```

Asp Gly Arg Cys Val Pro Glu Ala Gln Cys Pro Lys Arg Met Val Lys
50                  55                  60

Arg Asp Glu Lys Cys Gly Pro Asn Glu Lys Phe Leu Lys Cys Arg Gly
65                  70                  75                  80

Cys Glu Gly Thr Cys Lys Glu Arg Leu Val Pro Cys Pro Arg Met Cys
                85                  90                  95

Lys Pro Pro Gly Cys Glu Cys Pro Ala Ser Glu Gly Phe Val Arg Asn
                100                 105                 110

Asp Lys Gly Glu Cys Ile Lys Phe Asp Asp Cys Pro Lys
                115                 120                 125

<210> SEQ ID NO 30
<211> LENGTH: 142
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(17)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid

<400> SEQUENCE: 30

Xaa Xaa Xaa Xaa Xaa Xaa Xaa Xaa Xaa Xaa Xaa Xaa Xaa Xaa Xaa Xaa
1               5                   10                  15

Xaa His Arg Lys Cys Gly Pro Asn Glu Glu Trp Thr Glu Cys Thr Gly
                20                  25                  30

Cys Glu Xaa Lys Cys Gly Xaa Gly Glu Xaa Pro Cys Pro Met Met Cys
                35                  40                  45

Arg Pro Pro Ser Cys Glu Cys Met Ala Gly Lys Gly Leu Arg Arg Thr
50                  55                  60

Xaa Asp Gly Arg Cys Val Pro Glu Ala Gln Cys Pro Lys Xaa Met Val
65                  70                  75                  80

Lys Arg Asp Glu Lys Cys Gly Xaa Asn Glu Lys Phe Leu Lys Cys Arg
                85                  90                  95

Gly Cys Glu Gly Thr Cys Lys Glu Arg Leu Val Pro Cys Pro Xaa Met
        100                 105                 110

Cys Lys Pro Pro Gly Cys Glu Cys Pro Ala Ser Glu Gly Phe Val Arg
        115                 120                 125

Asn Asp Lys Xaa Glu Cys Ile Lys Phe Asp Asp Cys Pro Lys
        130                 135                 140

<210> SEQ ID NO 31
<211> LENGTH: 1343
<212> TYPE: DNA
<213> ORGANISM: Ancylostoma

<400> SEQUENCE: 31

| | | |
|---|---|---|
| atgggcagca gccatcatca tcatcatcac agcagcggcc tggtgccgcg cggcagccat | 60 |
| atggctagca tgactggtgg acagcaaatg ggtcgcggat ccgaattcga gctcaccact | 120 |
| tgtccaggaa atgatctaac agatgctgaa cgcacactgc taactagggt gcacaattcc | 180 |
| attcgacggg aaatagcgca aggagttgca acaactacc atggtggtaa actgcctgct | 240 |
| ggaaagaaca tatacaggat gagatacagc tgtgagctgg aacaggctgc tattgatgct | 300 |
| agtcaaacct tctgttccgc atcattggag gaaccacaga aatatggaca aacatccaa | 360 |
| gcatacgtca caccatctat aatcgctcgc ccgaaaaacg accttcttga agatgcagtg | 420 |
| aaacaatggt atctgcctgt tatctactac ggcaacgcg acgcggccaa caagttcacc | 480 |
| gatccgcgct tgtacacatt tgcaaacctc gcctacgaca gaacactgc acttggctgt | 540 |
| cactatgcga aatgtcaagg ccctgacaga atcgtcatta gttgcatgta caacaacgtc | 600 |
| gttcctgaca acgctgtgat ctacgagcca ggaactgctt gcgtaaaaga tcaggactgc | 660 |
| actacttatc ctcagtccac atgcaaggac agccttgca ttattcctac gccacatcca | 720 |
| ccaaatccac caaatccacc acctgcaatg tgtccaaacg ctgaaatgac tgatgcagca | 780 |
| cgaaagaagg tcctcgacat gcacaactgg cgcagatcgc agctcgctct gggaaacgtt | 840 |
| caaaacggga aaaatgctta caactgcccc actgcaacag acatgtacaa gatggaatat | 900 |
| gattgcgacc tcgagaacag cgctctagcg tatgcaaagc aatgtagtct cgttggttca | 960 |
| gcagaaggaa ctcgtccagg agaaggcgag aatgtccaca aaggcgctct cgtaaccgat | 1020 |
| ccggaggctg cagttcagac cgcagttcaa gcatggtgga gtcaaatctc acaaaatgga | 1080 |
| ctcaatgcac agatgaaatt cactgctttc ttgaaggaca gcctgacgc tccgacagcg | 1140 |
| tttacacaga tggcgtgggc caaatccgta aagcttggat gtgctgtctc taattgtcag | 1200 |
| gcagatacct tcaccgtctg tagatacaaa gctgccggaa acatcgtggg cgaattcatc | 1260 |
| tataccaagg gaaatgtatg cgacgcctgt aaagccacat gcattaccgc ggaaggtctt | 1320 |
| tgcccaacgc cttgagcggc cgc | 1343 |

<210> SEQ ID NO 32
<211> LENGTH: 767
<212> TYPE: DNA
<213> ORGANISM: Ancylostoma

<400> SEQUENCE: 32

| | | |
|---|---|---|
| atgggcagca gccatcatca tcatcatcac agcagcggcc tggtgccgcg cggcagccat | 60 |
| atggctagca tgactggtgg acagcaaatg ggtcgcggat ccgaattcga gctcaccact | 120 |
| tgtccaggaa atgatctaac agatgctgaa cgcacactgc taactagggt gcacaattcc | 180 |
| attcgacggg aaatagcgca aggagttgca acaactacc atggtggtaa actgcctgct | 240 |

-continued

```
ggaaagaaca tatacaggat gagatacagc tgtgagctgg aacaggctgc tattgatgct      300
agtcaaacct tctgttccgc atcattggag gaaccacaga atatggaca aacatccaa        360 gcatacgtca caccatctat aatcgctcgc ccgaaaaacg accttcttga agatgcagtg      420
aaacaatggt atctgcctgt tatctactac ggccagcgcg acgcggccaa caagtttacg      480
gatccgcgct tgtacacatt tgcaaacctc gcctacgaca agaacactgc acttggctgt      540
cactatgcga aatgtcaagg ccctgacaga atcgtcatta gttgcatgta caacaacgtc      600
gttcctgaca acgcagtgat ctacgagcct ggaactgctt gcgtaaaaga tgcggactgc      660
actacttatc ctcagtccac atgcaaggac agcctttgca ttattcctac gccacatcca      720
ccaaatccac caaatccacc accagcaatg agtccatgag cggccgc                    767
```

<210> SEQ ID NO 33
<211> LENGTH: 444
<212> TYPE: PRT
<213> ORGANISM: Ancylostoma

<400> SEQUENCE: 33

```
Met Gly Ser Ser His His His His His Ser Ser Gly Leu Val Pro
1               5                   10                  15

Arg Gly Ser His Met Ala Ser Met Thr Gly Gly Gln Gln Met Gly Arg
                20                  25                  30

Gly Ser Glu Phe Glu Leu Thr Thr Cys Pro Gly Asn Asp Leu Thr Asp
            35                  40                  45

Ala Glu Arg Thr Leu Leu Thr Arg Val His Asn Ser Ile Arg Arg Glu
        50                  55                  60

Ile Ala Gln Gly Val Ala Asn Asn Tyr His Gly Gly Lys Leu Pro Ala
65                  70                  75                  80

Gly Lys Asn Ile Tyr Arg Met Arg Tyr Ser Cys Glu Leu Glu Gln Ala
                85                  90                  95

Ala Ile Asp Ala Ser Gln Thr Phe Cys Ser Ala Ser Leu Glu Glu Pro
            100                 105                 110

Gln Lys Tyr Gly Gln Asn Ile Gln Ala Tyr Val Thr Pro Ser Ile Ile
        115                 120                 125

Ala Arg Pro Lys Asn Asp Leu Leu Glu Asp Ala Val Lys Gln Trp Tyr
    130                 135                 140

Leu Pro Val Ile Tyr Tyr Gly Gln Arg Asp Ala Ala Asn Lys Phe Thr
145                 150                 155                 160

Asp Pro Arg Leu Tyr Thr Phe Ala Asn Leu Ala Tyr Asp Lys Asn Thr
                165                 170                 175

Ala Leu Gly Cys His Tyr Ala Lys Cys Gln Gly Pro Asp Arg Ile Val
            180                 185                 190

Ile Ser Cys Met Tyr Asn Asn Val Val Pro Asp Asn Ala Val Ile Tyr
        195                 200                 205

Glu Pro Gly Thr Ala Cys Val Lys Asp Gln Asp Cys Thr Thr Tyr Pro
    210                 215                 220

Gln Ser Thr Cys Lys Asp Ser Leu Cys Ile Ile Pro Thr Pro His Pro
225                 230                 235                 240

Pro Asn Pro Pro Asn Pro Pro Ala Met Cys Pro Asn Ala Glu Met
                245                 250                 255

Thr Asp Ala Ala Arg Lys Lys Val Leu Asp Met His Asn Trp Arg Arg
            260                 265                 270

Ser Gln Leu Ala Leu Gly Asn Val Gln Asn Gly Lys Asn Ala Tyr Asn
        275                 280                 285
```

```
Cys Pro Thr Ala Thr Asp Met Tyr Lys Met Glu Tyr Asp Cys Asp Leu
    290                 295                 300

Glu Asn Ser Ala Leu Ala Tyr Ala Lys Gln Cys Ser Leu Val Gly Ser
305                 310                 315                 320

Ala Glu Gly Thr Arg Pro Gly Glu Gly Glu Asn Val His Lys Gly Ala
                325                 330                 335

Leu Val Thr Asp Pro Glu Ala Val Gln Thr Ala Val Gln Ala Trp
            340                 345                 350

Trp Ser Gln Ile Ser Gln Asn Gly Leu Asn Ala Gln Met Lys Phe Thr
        355                 360                 365

Ala Phe Leu Lys Asp Lys Pro Asp Ala Pro Thr Ala Phe Thr Gln Met
    370                 375                 380

Ala Trp Ala Lys Ser Val Lys Leu Gly Cys Ala Val Ser Asn Cys Gln
385                 390                 395                 400

Ala Asp Thr Phe Thr Val Cys Arg Tyr Lys Ala Ala Gly Asn Ile Val
                405                 410                 415

Gly Glu Phe Ile Tyr Thr Lys Gly Asn Val Cys Asp Ala Cys Lys Ala
                420                 425                 430

Thr Cys Ile Thr Ala Glu Gly Leu Cys Pro Thr Pro
            435                 440

<210> SEQ ID NO 34
<211> LENGTH: 252
<212> TYPE: PRT
<213> ORGANISM: Ancylostoma

<400> SEQUENCE: 34

Met Gly Ser Ser His His His His His Ser Ser Gly Leu Val Pro
1               5                   10                  15

Arg Gly Ser His Met Ala Ser Met Thr Gly Gly Gln Gln Met Gly Arg
                20                  25                  30

Gly Ser Glu Phe Glu Leu Thr Thr Cys Pro Gly Asn Asp Leu Thr Asp
            35                  40                  45

Ala Glu Arg Thr Leu Leu Thr Arg Val His Asn Ser Ile Arg Arg Glu
50                  55                  60

Ile Ala Gln Gly Val Ala Asn Asn Tyr His Gly Gly Lys Leu Pro Ala
65                  70                  75                  80

Gly Lys Asn Ile Tyr Arg Met Arg Tyr Ser Cys Glu Leu Glu Gln Ala
                85                  90                  95

Ala Ile Asp Ala Ser Gln Thr Phe Cys Ser Ala Ser Leu Glu Glu Pro
            100                 105                 110

Gln Lys Tyr Gly Gln Asn Ile Gln Ala Tyr Val Thr Pro Ser Ile Ile
        115                 120                 125

Ala Arg Pro Lys Asn Asp Leu Leu Glu Asp Ala Val Lys Gln Trp Tyr
    130                 135                 140

Leu Pro Val Ile Tyr Tyr Gly Gln Arg Asp Ala Ala Asn Lys Phe Thr
145                 150                 155                 160

Asp Pro Arg Leu Tyr Thr Phe Ala Asn Leu Ala Tyr Asp Lys Asn Thr
                165                 170                 175

Ala Leu Gly Cys His Tyr Ala Lys Cys Gln Gly Pro Asp Arg Ile Val
            180                 185                 190

Ile Ser Cys Met Tyr Asn Asn Val Val Pro Asp Asn Ala Val Ile Tyr
        195                 200                 205

Glu Pro Gly Thr Ala Cys Val Lys Asp Ala Asp Cys Thr Thr Tyr Pro
```

```
            210                 215                 220
Gln Ser Thr Cys Lys Asp Ser Leu Cys Ile Ile Pro Thr Pro His Pro
225                 230                 235                 240

Pro Asn Pro Pro Asn Pro Pro Ala Met Ser Pro
                245                 250

<210> SEQ ID NO 35
<211> LENGTH: 8
<212> TYPE: PRT
<213> ORGANISM: Artificial
<220> FEATURE:
<223> OTHER INFORMATION: Synthetic

<400> SEQUENCE: 35

Arg Phe Val Pro Cys Thr Arg Asn
1               5

<210> SEQ ID NO 36
<211> LENGTH: 10
<212> TYPE: PRT
<213> ORGANISM: Artificial
<220> FEATURE:
<223> OTHER INFORMATION: Synthetic

<400> SEQUENCE: 36

Arg Asp Ala Glu Gly Asn Cys Ile Lys Phe
1               5                   10

<210> SEQ ID NO 37
<211> LENGTH: 64
<212> TYPE: PRT
<213> ORGANISM: Artificial
<220> FEATURE:
<223> OTHER INFORMATION: Synthetic

<400> SEQUENCE: 37

Met Gly Pro Glu Ser Cys Gly Pro Asn Glu Val Trp Thr Glu Cys Thr
1               5                   10                  15

Gly Cys Glu Leu Lys Cys Gly Gln Asp Glu Asn Thr Pro Cys Thr Leu
                20                  25                  30

Asn Cys Arg Pro Pro Ser Cys Glu Cys Ser Pro Gly Arg Gly Met Arg
            35                  40                  45

Arg Thr Asn Asp Gly Arg Cys Ile Pro Ala Ser Gln Cys Pro Gln His
        50                  55                  60

<210> SEQ ID NO 38
<211> LENGTH: 65
<212> TYPE: PRT
<213> ORGANISM: Artificial
<220> FEATURE:
<223> OTHER INFORMATION: Synthetic

<400> SEQUENCE: 38

Met Arg Ala Lys Arg Glu Glu Gln Cys Lys Pro Asn Glu Gln Trp Ser
1               5                   10                  15

Pro Cys Arg Gly Cys Glu Gly Thr Cys Ala Gln Arg Phe Val Pro Cys
                20                  25                  30

Thr Arg Asn Cys Arg Pro Pro Gly Cys Glu Cys Val Ala Gly Ala Gly
            35                  40                  45
```

```
Phe Val Arg Asp Ala Glu Gly Asn Cys Ile Lys Phe Asp Asp Cys Pro
 50                  55                  60

Lys
 65
```

METHODS, DEVICES, KITS AND COMPOSITIONS FOR DETECTING ROUNDWORM, WHIPWORM, AND HOOKWORM

CROSS REFERENCE

This application is a divisional of U.S. patent application Ser. No. 12/467,826 filed May 18, 2009 (now U.S. Pat. No. 7,951,547, issued May 31, 2011) which in turn claims priority to U.S. Provisional Patent Application Ser. Nos. 61/122,260, filed Dec. 12, 2008; 61/128,077, filed May 19, 2008; 61/128,079, filed May 19, 2008; 61/128,076, filed May 19, 2008; 61/128,099, filed May 19, 2008; and 61/122,254, filed Dec. 12, 2008; and is a continuation-in-part of U.S. patent application Ser. No. 11/763,592, filed Jun. 15, 2007 (now U.S. Pat. No. 7,736,660, issued Jun. 15, 2010) and is a continuation-in-part of U.S. patent application Ser. No. 11/763,583, filed Jun. 15, 2007, which are incorporated by reference herein in their entirety.

BACKGROUND OF THE INVENTION

1. Field of the Invention

The present invention relates to compositions, devices, kits and methods for the detection of and distinguishing between roundworm, whipworm and hookworm in mammals. More particularly, the present invention relates to antibodies and antibody compositions, devices, kits, and methods for detecting the presence or absence of roundworm antigen, whipworm antigen and hookworm antigen in a sample from a mammal and for distinguishing between roundworm, whipworm and hookworm antigens.

2. Description of the Prior Art

Parasitic worm (helminth) infections are common in animals and, if not diagnosed and treated, can cause serious disease or death. Current methods for diagnosis of parasitic worm infections primarily involve microscopic examination of fecal samples, either directly in fecal smears or following concentration of ova and parasites by flotation in density media. Despite this procedure's high adoption, the method has significant shortcomings. These microscopic methods are time consuming and require specialized equipment. In addition, the accuracy of results of these methods is highly dependent upon the skill and expertise of the operator. For example, the presence of whipworms is determined by looking for eggs, but these are excreted intermittently and in small numbers. Hookworms are difficult for the average practitioner to detect either early in infection or in young animals. The specificity of roundworm diagnosis using microscopic examination is approximately 50%.

Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician. Therefore, any reduction in the number of steps required to perform a fecal test and any reduction in contact between test operator and the test material is desirable. Clinical laboratories have been using the immunoassay methods for the detection of various viruses, bacteria and non-helminth parasites and organisms in feces. However, there remains a need for a simple immunoassay method for the detection of a parasitic worm infection in feces, whole blood or in serum.

SUMMARY OF THE INVENTION

In one aspect, the invention provides a device for specifically binding and isolating helminthic antigens from a sample, for example coproantigens from a fecal sample, the device comprising a solid support, wherein the solid support has immobilized thereon at least two antibodies selected from the group consisting of (a) a first antibody capable of specifically binding a roundworm coproantigen, but not a whipworm or hookworm coproantigen; (b) a second antibody capable of specifically binding a whipworm coproantigen, but not a roundworm or hookworm coproantigen; and (c) a third antibody capable of specifically binding a hookworm coproantigen, but not a whipworm or hookworm coproantigen. The device, may be, but is not limited to being, for example, an ELISA device, such as a lateral flow immunoassay device or microtiterplate device. Samples that may be tested for roundworm, whipworm and hookworm by the device include, but are not limited to being, feces, digestive tract mucous, urine, whole blood, serum, mammary milk and whole tissue, such as tissue from mammary gland, intestine, liver, heart, lung, esophagus, brain, muscle, and eye, for example. The device further may include, but need not include, one or more reagents for the detection of one or more of the group consisting of: one or more non-worm parasites, one or more viruses, one or more fungi, and one or more bacteria.

In yet another aspect, the invention provides a method of detecting the presence or absence of one or more helminthic antigens in a sample, for example coproantigens from a fecal sample, the method comprising: (a) contacting a sample from a mammal with at least two antibodies selected from the group consisting of: (i) a first antibody capable of specifically binding a roundworm coproantigen, but not a whipworm or hookworm coproantigen; (ii) a second antibody capable of specifically binding a whipworm coproantigen, but not a roundworm or hookworm coproantigen; and (iii) a third antibody capable of specifically binding a hookworm coproantigen, but not a whipworm or hookworm coproantigen (b) forming antibody-coproantigen complexes in the presence of the coproantigens, if any, in the sample; and (c) detecting the presence or absence of the antibody-coproantigen complexes, if any. The one or more helminthic coproantigens include coproantigens of roundworm, such as *Toxocara canis* (*T. canis*), *Toxocara cati* (*T. cati*), *Toxocara vitulorum* (*T. vitulorum*), *Toxascaris leonina* (*T. leonina*), *Baylisascaris procyonis* (*B. procyonis*), *Ascaridia galli* (*A. galli*), *Parascaris equorum* (*P. equorum*), *Ascaris suum* (*A. suum*), or *Ascaris lumbricoides* (*A. lumbricoides*), *Anisakis simplex* (*A. simplex*), or *Pseudoterranova decipiens* (*P. decipiens*), whipworm such as *Trichuris vulpis*, *Trichuris campanula*, *Trichuris serrata*, *Trichuris suis*, *Trichuris trichiura*, *Trichuris discolor*, and hookworm, such as *Ancylostoma caninum*, *Ancylostoma braziliense*, *Ancylostoma duodenal*, *Ancylostoma ceylanicum*, *Ancylostoma tubaeforme* and *Ancylostoma pluridentatum*, *Necator americanus*, and *Uncinaria stenocephala*, for example, in a sample obtained from a mammal, such as a canine, feline, porcine, bovine, or human and distinguishing between roundworm, whipworm and hookworm. In one aspect, the method is carried out to test a fecal mammalian sample for roundworm coproantigen, whipworm coproantigen, and hookworm coproantigen. The method, however, is not limited to being carried out to test a fecal sample. In addition to feces, the sample therefore may be, but is not limited to being whole blood, serum, mammary milk and whole tissue, such as tissue from mammary gland, intestine, liver, heart, lung, esophagus, brain, muscle, and eye, for example.

In yet another aspect, the invention provides a method of diagnosing whether a mammal is infected with one or more parasitic worms, the method comprising the steps of: (a)

contacting a sample from a mammal with at least two antibodies selected from the group consisting of: (i) a first antibody capable of specifically binding a roundworm coproantigen, but not a whipworm or hookworm coproantigen; (ii) a second antibody capable of specifically binding a whipworm coproantigen, but not a roundworm or hookworm coproantigen; and (iii) a third antibody capable of specifically binding a hookworm coproantigen, but not a whipworm or hookworm coproantigen (b) forming antibody-coproantigen complexes in the presence of the coproantigens, if any, in the sample; (c) detecting the presence or absence of the antibody-coproantigen complexes, if any; and (d) diagnosing the mammal as having: (i) a roundworm infection if a roundworm antibody-coproantigen complex is present; (ii) a whipworm infection if a whipworm antibody-coproantigen complex is present; and (iii) a hookworm infection if a hookworm antibody-coproantigen complex is present. The method may also be used to test for and distinguish between environmental contamination with roundworm, whipworm and/or hookworm. Environmental samples that may be tested for roundworm, whipworm and/or hookworm by the device include, but are not limited to soil, decomposing material, or fecal matter from residential settings including yards, gardens, sand boxes, playgrounds. Testing locations may also include parks, beaches, forests, farms, or other locations exposed to fecal material from dogs, cats, or other mammalian hosts of roundworms. Feces from indoor and outdoor litter boxes may also be tested.

In yet another aspect, the present invention includes a kit for carrying out one or more steps of the method of the invention. The kit may optionally include, for example, the device and one or more of the compositions of the present invention and instructions for carrying out the method of the present invention. The kit may further optionally include, for example, one or more indicator reagents, one or more antibody labeling compounds, one or more antibodies, one or more antigen capture reagents, one or more inhibitors, and one or more wash reagents to be used as part of the device and/or to be used in carrying out the method.

In yet another aspect, the present invention includes a device for specifically binding helminthic antigens from a sample, for example coproantigens from a fecal sample, the device comprising a solid support, wherein the solid support has immobilized thereon at least two antibodies selected from the group consisting of: (a) a first antibody capable of specifically binding a roundworm coproantigen, but not a whipworm or hookworm coproantigen; (b) a second antibody capable of specifically binding a whipworm coproantigen, but not a roundworm or hookworm coproantigen; and (c) a third antibody capable of specifically binding a hookworm coproantigen, but not a whipworm or hookworm coproantigen; and (d) one or more types of roundworm antigen, whipworm antigen, and/or hookworm antigen, wherein the one or more types of roundworm antigen, whipworm antigen, and hookworm antigen are specifically bound to the antibodies.

BRIEF DESCRIPTION OF THE DRAWINGS

FIG. 3 shows the nucleotide sequence of a 1210-nucleotide cDNA sequence from whole adult *Trichuris vulpis* (SEQ ID NO:1).

FIG. 4 shows the nucleotide sequence of a 1059-nucleotide cDNA sequence from whole adult *Trichuris vulpis*. (SEQ ID NO:2).

FIG. 5 shows a comparison alignment of SEQ ID NO:3 and SEQ ID NO:4. The consensus sequence of SEQ ID NO:3 and SEQ ID NO:4 is shown as SEQ ID NO:9.

FIG. 6 shows the nucleotide sequence of an 865-nucleotide cDNA sequence from whole adult *Toxocara canis*. (SEQ ID NO:10).

FIG. 7 shows the nucleotide sequence of a 632-nucleotide cDNA sequence from whole adult *Toxocara cati*. (SEQ ID NO:11).

FIG. 8 shows a comparison alignment of SEQ ID NO:13 and SEQ ID NO:14. The consensus sequence of SEQ ID NO:13 and SEQ ID NO:14 is shown as SEQ ID NO:16.

FIG. 9 shows the nucleotide sequence of a 535-nucleotide cDNA sequence from whole adult *Toxocara canis*. (SEQ ID NO:17).

FIG. 10 shows the nucleotide sequence of a 536-nucleotide cDNA sequence from whole adult *Toxocara cati*. (SEQ ID NO:18).

FIG. 11 shows a comparison alignment of SEQ ID NO:20 and SEQ ID NO:21. The consensus sequence of SEQ ID NO:20 and SEQ ID NO:21 is shown as SEQ ID NO:23.

FIG. 12 shows the nucleotide sequence of a 469-nucleotide cDNA sequence from whole adult *Toxocara canis*. (SEQ ID NO:24).

FIG. 13 shows the nucleotide sequence of a 548-nucleotide cDNA sequence from whole adult *Toxocara cati*. (SEQ ID NO:25).

FIG. 14 shows a comparison alignment of SEQ ID NO:27 and SEQ ID NO:28. The consensus sequence of SEQ ID NO:27 and SEQ ID NO:28 is shown as SEQ ID NO:30.

FIG. 18. shows the amino acid sequence of the full length DIV6728 (SEQ ID NO: 21) with the two peptides (SEQ ID NO: 35 and SEQ ID NO: 36) identified by Mass Spectrometry analysis identified by highlighting them in the shaded boxes following the method of the present invention in the third Example.

FIG. 19 shows an alignment of the 6728N (SEQ ID NO: 37) and 6728C (SEQ ID NO: 38) amino acid sequences encoded by the constructs following the method of the present invention in the fourth Example.

DETAILED DESCRIPTION OF THE PREFERRED EMBODIMENTS OF THE INVENTION

I. Introduction

Figure 1:
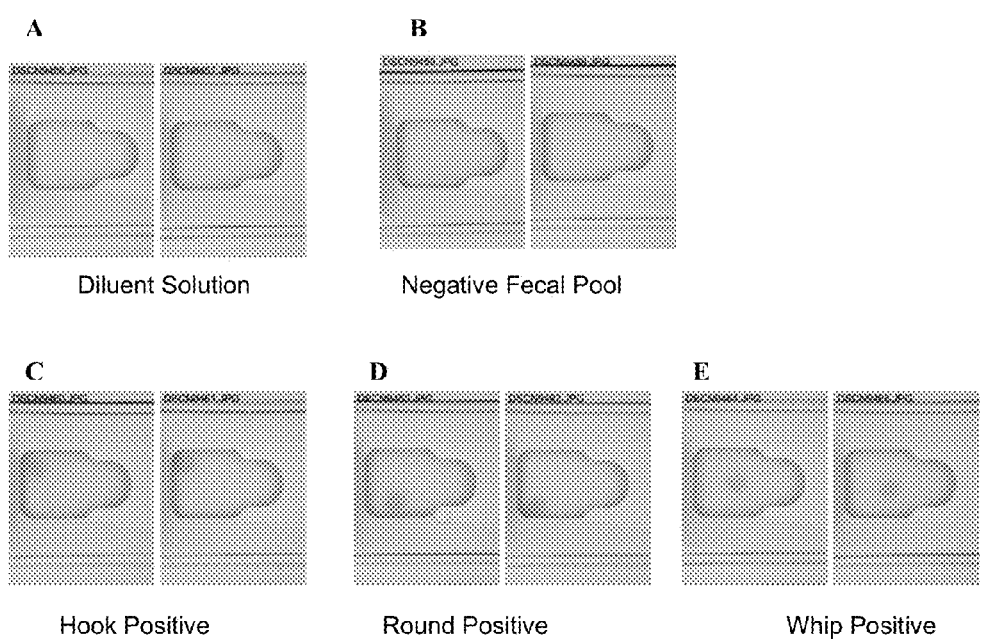
FIG. 1 shows the results of an ELISA assay, which was carried out by using a lateral flow device and which tested fecal samples from canines infected with roundworm, whipworm and/or hookworm by following the method of the present invention in a first Example.

The present invention is generally directed to methods, devices, and kits for detecting and distinguishing between roundworm, whipworm and hookworm in a fecal sample obtained from a mammal. The present invention relates to roundworm coproantigens from *Toxocara*, such as *Toxocara canis* or *Toxocara cati*, whipworm coproantigens from *Trichuris*, such as *Trichuris vulpis*, and hookworm coproantigens *Ancylostoma* such as *Anclostoma caninum*, for example. In particular, the present invention relates methods, devices and kits for detecting and distinguishing between roundworm, such as *Toxocara, Toxascaris, Baylisascaris, Ascaridia, Parascaris, Ascaris, Anisakis*, or *Pseudoterranova*, including *T. canis, T. cati, T. vitulorum, T. leonina, T. vitulorum, B. procyonis, A. galli, P. equorum, A. lumbricoides*, and *A. suum, A. simplex*, and *P. decipiens*, whipworm, such as *Trichuris vulpis, Trichuris serrata, T. campanula*, and *Trichuris trichiura*, and hookworm, such as *Ancylostoma caninum, Ancylostoma braziliense, Ancylostoma duodenal, Ancylostoma ceylanicum, Ancylostoma tubaeforme* and *Ancylostoma pluridentatum, Necator americanus*, and *Uncinaria stenocephala*, for example.

The present invention provides a superior alternative to the existing microscopic inspection techniques. This is true because the present invention provides devices, kits and methods for detecting the presence or absence of roundworm, whipworm and hookworm in a sample from a mammal that: (1) are both easy to use and yield consistently reliable results; (2) allow for the absence or presence of whipworm in a mammal to be confirmed regardless of whether that mammal is infected with hookworm, roundworm, and/or heartworm; (3) can detect roundworm, whipworm and hookworm prior to the time that the ova first appear in the infected host's feces; and (4) can distinguish between roundworm, whipworm and hookworm infections.

The present invention is based in part on the discovery of unexpected properties of compositions specific to roundworm, whipworm and hookworm infections. Specifically, it was determined that antibodies raised against worm specific polypeptides (or raised against an extract of whole worms, or extract of worm reproductive organs, or extract of worm intestines) can be used to capture, detect, and distinguish between roundworm antigens, whipworm antigens, and hookworm antigens in a mammal. The specificity for each type of worm is surprising because roundworms, whipworms, and hookworms all are related nematodes, and an antibody raised against a protein isolated from any one of these worms would be expected to crossreact with one or more of the other worms, host antigens, or other host components.

It was further determined that this antibody can be used to capture and detect roundworm, whipworm and hookworm antigens in a mammal as early as 9 days after the mammal is first infected. This ability to detect roundworm, whipworm or hookworm so soon after infection, and before the appearance of any ova in the feces of the infected mammal, is surprising because ova generally do not appear in the feces of an infective host until about five-to-eight weeks after the host becomes infected.

The present invention therefore includes methods, devices, and kits that use antibodies and/or fragments thereof to specifically capture and detect and distinguish between roundworm, whipworm and hookworm antigens in a mammal. The ability of the present invention to detect and diagnose roundworm even when one or more other worm types are also present allows the mammal's caregiver the opportunity to optimally select a treatment for ridding the roundworm, whipworm and/or hookworm from the mammal. Further, the ability of the present invention to, in some cases, detect roundworm, whipworm and/or hookworm as early as 9 days after the mammal is first infected provides the possibility that the caregiver may begin such treatment before the mammal becomes severely sickened. An intervention prior to appearance of ova in the feces would also greatly reduce or eliminate the possibility that the infestation is spread to other animals or humans.

II. Definitions and Uses of Term

The term "compositions of the invention" refers to all of the nucleic acids, polypeptides, antibodies, and mixtures that include one or more of those nucleic acids, polypeptides, and antibodies and one or more other compounds, that can be used to detect the presence or absence of roundworm, whipworm and/or hookworm in a sample obtained from a mammal by carrying out the method of the present invention that are explicitly described, implicitly encompassed or otherwise disclosed herein.

"A sample from a mammal" in which roundworm, whipworm and/or hookworm can be detected by the present invention includes all bodily components and extracts thereof, such as any fluid, solid, cell or tissue, that are capable of containing roundworm, whipworm and/or hookworm antigen. Exemplary samples therefore include, but are not limited to being, feces, milk, whole blood and portions thereof, including serum, and further include tissue extracts, including tissue from mammary gland, intestine, liver, heart, lung, esophagus, brain, muscle, and eye, for example. The sample may be taken directly from the mammal or the sample may be taken from anything that has contacted the mammal. For example, the sample may be fresh or decaying fecal droppings from the mammal. As another example, the sample may include soil, dirt, sand, plant material, or any other material that may be mixed with bodily components that may be left behind by a mammal, such as feces, for example. As such, the sample may be taken from an environmental source, including soil, decomposing material, or fecal matter from forests, farms, or residential settings, including litter boxes, yards, gardens, sand boxes, playgrounds, parks, and beaches. No matter the origin or the content of the sample, this sample sometimes is referred to herein as the "sample", the "mammalian sample", the "test sample" or the "sample under test".

As used herein, "nucleic acid" is synonymous with, and therefore is used interchangeably with, "gene", "DNA", "cDNA", "EST", "polynucleotide", "oligonucleotide", "polynucleic acid", "RNA" and "mRNA". A nucleic acid may be in double-stranded form or it may be in single-stranded form. Further, a nucleic acid is either naturally isolated, such as from a whole roundworm, whipworm and/or hookworm or a portion thereof, for example, or it is artificially synthesized, either in a recombinant host organism or by any other artificial means known to the skilled artisan, such as by employing a PCR-based technique, by creating a transgenic organism that synthesizes the nucleic acid, by using a DNA synthesizing machine, or by any another molecular-based technique, for example.

"Polypeptide", "peptide" and "protein" are synonymous terms that are used interchangeably herein to refer to a polymer of amino acid residues. A polypeptide, peptide and protein of the present invention may be either naturally isolated, such as from a whole roundworm, whipworm or hookworm or from a portion of roundworm, whipworm or hookworm for example, or artificially synthesized, either in a recombinant host organism or by any other artificial means known to the skilled artisan.

The term "antibody" or "antibody of the present invention" refers to any antibody that is able to specifically bind to one or more antigens for the particular worm without binding to antigens from the other worms. For example antibodies to the one or more roundworm antigens are able to specifically bind to one or more roundworm antigens, but not to any antigens from hookworm or whipworm and antibodies to the one or more whipworm antigens are able to specifically bind to one or more whipworm antigens, but not to any antigens from roundworm and hookworm. The antibodies of the present invention may be raised against one or more immunogenic polypeptides of the present invention. Unless otherwise stated, it is to be understood that the antibody of the present invention may include a mixture of two or more different types of antibody. For example, the antibody may be a mixture of two types of antibodies, wherein one of the two types specifically binds to one particular antigen and the other of the two types specifically binds to some other antigen.

The term "first antibody" as used herein means one or more antibodies capable of specifically binding a roundworm coproantigen, but not a whipworm or hookworm coproantigen.

The term "second antibody" as used herein means one or more antibodies capable of specifically binding a whipworm coproantigen, but not a roundworm or hookworm coproantigen.

The term "third antibody" as used herein means one or more antibodies capable of specifically binding a hookworm coproantigen, but not a whipworm or roundworm coproantigen.

The "immunogenic polypeptide of the present invention" and, more simply, "the polypeptide of the present invention", is an immunogen against which the antibodies of the present invention may be raised. All "polypeptides of the present invention" are immunogenic and therefore may be used to elicit an immune response in a host animal to produce the antibodies of the present invention. Unless otherwise stated, it is to be understood that the polypeptide of the present invention may be one component of a mixed composition of a plurality of components.

An "immunogen" is any agent, such as the immunogenic polypeptide of the present invention, for example, that is capable of eliciting an immune response in an animal that is exposed to that agent.

The term "roundworm", as used herein, refers to helminths such as intestinal roundworms of the order Ascaridida, which includes the genera *Toxocara, Toxascaris, Baylisascaris, Ascaridia, Parascaris, Ascaris, Anisakis*, and *Pseudoterranova*. Thus, the term "roundworm", as used herein, does not refer to the entirety of the phylum Nematoda. Therefore, "roundworm" does not include any member of the genera *Ancylostoma, Uncinaria, Necator, Trichuris, Wuchereria, Brugia* or *Dirofilaria*.

A "roundworm coproantigen" or a "coproantigen of roundworm" is any roundworm product that is present in the feces of a mammal having a roundworm infection and that may be specifically bound by one or more of the antibodies of the invention. For example, a roundworm coproantigen may be, but is not limited to being, one or more of the polypeptides of the invention. The present inventors have determined that a novel C-terminal 7 kD isoform of DIV6728, which is a excretory/secretory protein of *T. canis*, is present in feces of *T. canis*-infected canines as early as 38 days after the canines first became infected with the *T. canis*. Therefore, a "roundworm coproantigen" may be this novel C-terminal 7 kD isoform of DIV6728 (which is referred to herein as "Copro6728") that has been observed in canine feces by the present inventors.

The term "whipworm", as used herein, refers to helminths such as intestinal whipworms of the genera *Trichuris* and *Trichocephalus*. Exemplary whipworms therefore include *Trichuris vulpis, Trichuris campanula, Trichuris serrata, Trichuris suis, Trichuris trichiura, Trichuris discolor* and *Trichocephalus trichiuris*. Further, the term "whipworm", as used herein, does not refer to the entirety of the phylum Nematoda. For example, "whipworm" does not include any member of the genera *Ancylostoma, Uncinaria, Necator, Toxocara, Toxascaris, Ascaris, Wuchereria, Brugia* or *Dirofilaria*.

A "whipworm coproantigen" or a "coproantigen of whipworm" is any whipworm product that is present in the feces of a mammal having a whipworm infection and that may be specifically bound by one or more of the antibodies of the invention. For example, a whipworm coproantigen may be, but is not limited to being, one or more of the polypeptides of the invention.

The term "hookworm," as used herein, refers to helminthes such as intestinal hookworm of the genera *Ancylostoma, Necator* and *Uncinaria*. Exemplary hookworms therefore include *Ancylostoma caninum, Ancylostoma braziliense, Ancylostoma duodenal, Ancylostoma* ceylanicum, *Ancylostoma tubaeforme* and *Ancylostoma pluridentatum, Necator americanus*, and *Uncinaria stenocephala*. Further, the term "hookworm," as used herein, does not refer to the entirety of the phylum Nematoda. For example, "hookworm" does not include any member of the genera *Trichuris, Trichocephalus Toxocara, Toxascaris, Ascaris, Wuchereria, Brugia* or *Dirofilaria*.

A "hookworm coproantigen" or a "coproantigen of hookworm" is any hookworm product that is present in the feces of a mammal having a hookworm infection and that may be specifically bound by one or more of the antibodies of the invention. For example, a hookworm coproantigen may be, but is not limited to being, one or more of the polypeptides of the invention. The present inventors have determined that a novel N-terminal 28 kDa isoform of ASP5, which is a excretory/secretory protein of *Ancylostoma*, is present in feces of *Ancylostoma*-infected canines as early as 9 days after the canines first became infected with the *Ancylostoma*. Therefore, a "hookworm coproantigen" may be this novel N-terminal 28 kDa isoform of ASP5 (which is referred to herein as "CoproASP5") that has been observed in canine feces by the present inventors.

"Specific for", "specifically binds", and "stably binds" means that a particular composition of the invention, such as an antibody, polypeptide, or oligonucleotide of the present invention, for example, recognizes and binds to one or more other agents with greater affinity than to at least one other agent. As one example, an antibody of the present invention is said to be "specific for", to "specifically bind", and to "stably bind" roundworm antigens whenever that antibody is able to recognize and bind to those roundworm antigens with greater affinity than to any other antigens from a non-roundworm parasitic worm. Such binding specificity can be tested using methodology well known in the art, for example, ELISA or a radioimmunoassay (RIA). Based on information observed regarding the binding specificity of a particular composition of the invention, the method of the present invention can be carried out under conditions that allow that composition to bind to (and therefore to allow the detection of such binding to) a particular agent or agents, but not to significantly bind other agents, while those conditions are maintained. As one example, the method of the present invention can be carried out under conditions that allow an antibody of the present invention to bind to (and therefore to allow the detection of such binding to) one or more roundworm antigens present in a particular sample, but not significantly to any hookworm or whipworm antigen that may be present in that sample, thereby allowing for the distinction between roundworm, whipworm and hookworm.

"Detecting roundworm" means detecting one or more roundworm-specific products, including one or more of the polypeptides, antibodies and nucleic acids of the present invention, or one or more roundworm antigens, or Copro6728, for example. The presence of one or more such roundworm products in a sample from a mammal is indicative that the mammal has a roundworm infection, regardless of whether any whole roundworm organism or ovum thereof is also present in that sample. Conversely, the absence of one or more such roundworm products a sample from a mammal is indicative that the mammal does not have a roundworm infection.

"Detecting whipworm" means detecting one or more whipworm-specific products, including one or more of the polypeptides, antibodies and nucleic acids of the present invention, or one or more whipworm antigens, for example. The presence of one or more such whipworm products in a sample from a mammal is indicative that the mammal has a whipworm infection, regardless of whether any whole whipworm organism or ovum thereof is also present in that sample. Conversely, the absence of one or more such whipworm products a sample from a mammal is indicative that the mammal does not have a whipworm infection.

"Detecting hookworm" means detecting one or more hookworm-specific products, including one or more of the polypeptides, antibodies and nucleic acids of the present invention, or one or more hookworm antigens, or CoproASP5, for example. The presence of one or more such hookworm products in a sample from a mammal is indicative that the mammal has a hookworm infection, regardless of whether any whole hookworm organism or ovum thereof is also present in that sample. Conversely, the absence of one or more such hookworm products a sample from a mammal is indicative that the mammal does not have a hookworm infection.

"Amino acid" refers to naturally occurring and synthetic amino acids. Amino acid residues are abbreviated as follows: Alanine is A or Ala; Arginine is R or Arg; Asparagine is N or Asn; Aspartic Acid is D or Asp; Cysteine is C or Cys; Glutamic Acid is E or Glu; Glutamine is Q or Gln; Glycine is G or Gly; Histidine is H or His; Isoleucine is I or Ile; Leucine is L or Leu; Lysine is K or Lys; Methionine is M or Met; Phenylalanine is F or Phe; Proline is P or Pro; Serine is S or Ser; Threonine is T or Thr; Tryptophan is W or Trp; Tyrosine is Y or Tyr; and Valine is V or Val. Except where defined otherwise herein, X or Xaa represents any amino acid. Other relevant amino acids include, but are not limited to being, 4-hydroxyproline and 5-hydroxylysine. In all cases, the amino acid sequence of a polypeptide described or otherwise referred to herein is presented in conventional form in that the left-most, or first, amino acid residue of the sequence is the N-terminal residue and the right-most, or last, amino acid residue of the sequence is the C-terminal residue.

A "conservative variant" of any particular nucleic acid sequence includes any sequence having one or more degenerate codon substitutions to that particular nucleic acid sequence, any sequence having one or more nucleotide substitutions to, insertions to, and deletions from that particular nucleic acid sequence, and the complementary sequence of that particular nucleic acid and the conservative variants of that complementary sequence. Conservative variants of a particular nucleic acid sequence preferably have at least about 85% identity, more preferably have at least about 90% identity, and even more preferably at least about 95-99% identity, to that particular nucleic acid sequence. Conservative variants of a particular nucleic acid sequence may be artificially synthesized or they may be isolated in their natural form from an organism.

A "conservative variant" of any particular polypeptide sequence is any polypeptide having an amino acid sequence that varies from the amino acid sequence of that particular polypeptide but still retains the specific binding properties of that particular polypeptide, such that an antibody of the present invention that is raised against the particular polypeptide is capable of specifically binding the variant polypeptide. Therefore, for example, a conservative variant of a particular polypeptide may have one or more amino acid substitutions, deletions, additions, and insertions to that particular polypeptide. For example, a conserved variant of a particular polypeptide may have 30 or fewer, 25 or fewer, 20 or fewer, 15 or fewer, 10 or fewer, or 5 or fewer, conserved amino acid substitutions to that particular polypeptide. Conservative variants of a particular polypeptide preferably, but not essentially, have at least about 80% identity, more preferably have at least about 90% identity, and even more preferably at least about 91-99% identity, to that particular polypeptide. A percent identity for any subject nucleic acid or amino acid sequence (e.g., any of polypeptides described herein) relative to another "target" nucleic acid or amino acid sequence can be determined as follows. First, a target nucleic acid or amino acid sequence of the invention can be compared and aligned to a subject nucleic acid or amino acid sequence, using the BLAST 2 Sequences (Bl2seq) program from the stand-alone version of BLASTZ containing BLASTN and BLASTP (e.g., version 2.0.14). The stand-alone version of BLASTZ can be obtained at www.ncbi.nlm.nih.gov. Instructions explaining how to use BLASTZ, and specifically the Bl2seq program, can be found in the 'readme' file accompanying BLASTZ.

The programs also are described in detail by Karlin et al. (1990) Proc. Natl. Acad. Sci. 87:2264; Karlin et al. (1990) Proc. Natl. Acad. Sci. 90:5873; and Altschul et al. (1997) Nucl. Acids Res. 25:3389.

"CoproASP5" refers to an N-terminal 28 kD fragment of ASP5 found in mammalian feces.

"Copro6728" refers to a C-terminal 7 kD portion of DIV6728 found in mammalian feces In a specific embodiment, copro6728 does not include the C-terminus of the full length DIV6728.

Bl2seq performs a comparison between the subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11 and extension cost of 1, a word size of 3, an expect value of 10, a per residue cost of 1 and a lambda ratio of 0.85 are used when performing amino acid sequence alignments. The output file contains aligned regions, of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains (e.g., α-helices, β-sheets, and loops).

The percent identity over a particular length is determined by counting the number of matched positions over that particular length, dividing that number by the length and multiplying the resulting value by 100. For example, if (i) a 500 amino acid target sequence is compared to a subject amino acid sequence, (ii) the Bl2seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180/200× 100=90). It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

Conservative variants of a particular polypeptide sequence may be artificially synthesized or they may be isolated in their natural form from an organism, including from a roundworm organism, such as *Toxocara canis, Toxocara cati*, and *Ascaris*, from a whipworm organism, such as *Trichuris* and *Trichocephalus*, and hookworm organism, such as *Ancylostoma, Necator* and *Uncinaria* for example. In one specific, non-limiting example for roundworm, the polypeptide of the invention having an amino acid sequence corresponding to SEQ ID NO: 27 shown below is a conservative variant of the polypeptide of the present invention having an amino acid sequence corresponding to SEQ ID NO:26 in that SEQ ID NO:27 is more than 95% identical to SEQ ID NO:26 over an alignment of 126 amino acids. More generally, each one of SEQ ID NO:26, SEQ ID NO:27, SEQ ID NO:28, SEQ ID NO:29 and SEQ ID NO:30 are conserved variants of each other. It is also to be understood that other conserved variants of the SEQ ID NO:26, SEQ ID NO:27, SEQ ID NO:28, SEQ ID NO:29 and SEQ ID NO:30 are contemplated by the present invention as described herein, but the skilled artisan would recognize that all of these contemplated variants are too numerous to list. The skilled artisan will also recognize that these variants include, but are not limited to, those have one or more substitutions of basic amino acid residues, one or more substitutions of acidic amino acid residues, one or more substitutions of polar amino acid residues, one or more substitutions of hydrophobic amino acid residues, one or more substitutions of aromatic amino acid residues, and one or more substitutions of small amino acid residues. ("Basic" amino acid residues are K, R and H. "Acidic" amino acid residues are D and E. "Polar" amino acid residues are N and Q. "Hydrophobic" amino acids are I, L, and V. "Aromatic" amino acid residues are F, Y, and W. "Small" amino acids are G, S, A, T and M.)

III. Nucleic Acids and Polypeptides of the Invention

The nucleic acids and polypeptides of the invention are described in detail in Provisional Applications: "Methods, Devices, Kits And Compositions For Detecting Whipworm," Application Ser. No. 61/128,077, filed May 19, 2008; "Methods, Devices, Kits And Compositions For Detecting Roundworm," Application Ser. No. 61/128,079, filed May 19, 2008; "Methods, Devices, Kits And Compositions For Detecting Roundworm," Application Ser. No. 61/128,076, files May 19, 2008; "Methods, Devices, Kits And Compositions For Detecting Roundworm," Application Ser. No. 61/128,099, filed May 19, 2008; "Compositions, Devices, Kits and Methods for Detecting Hookworm", Application Ser. No. 61/122,254, filed Dec. 12, 2008; and Utility Applications: "Roundworm Coproantigen Detection", application Ser. No. 11/763,592, filed Jun. 15, 2007 and "Device, Kit and Method for Hookworm Antigen Detection", application Ser. No. 11/763,583, filed Jun. 15, 2007, "Methods, Devices, Kits, Compositions for Detecting Roundworm" filed concurrently herewith, and are all incorporated by reference in their entirety.

In an attempt to identify compositions that may be used to confirm the presence or absence of roundworm in a fecal sample and to distinguish roundworm from other parasitic worm infections, a plurality of oligonucleotide primers were designed, synthesized and used in 5' RACE, 3'RACE and RT-PCR reactions that included total RNA isolated from either whole adult *Toxocara canis* or whole adult *Toxocara cati*. As a result of these efforts, an 469-nucleotide cDNA sequence was deduced from *Toxocara canis* (identified herein as SEQ ID NO:25), and a 548-nucleotide cDNA sequence was deduced from *Toxocara cati* (identified herein as SEQ ID NO:26). (BLAST searches that were carried out using SEQ ID NO:25 and SEQ ID NO:26 indicated these sequences are likely to encode members of serine protease inhibitor families that were first identified in *Ascaris*, but that had not been identified in either *T. canis* or *T. cati* until now.)

In an attempt to identify compositions that may be used to confirm the presence or absence of whipworm in a fecal sample and to distinguish whipworm from other parasitic worm infections, a plurality of oligonucleotide primers were designed, synthesized and used in 5' RACE, 3'RACE and RT-PCR reactions that included total RNA isolated from whole adult *Trichuris vulpis*. As a result of these efforts, a 1210-nucleotide cDNA sequence and a 1059-nucleotide cDNA sequence were deduced (identified herein as SEQ ID NO:1 and SEQ ID NO:2, respectively. (BLAST searches that were carried out using SEQ ID NO:1 and SEQ ID NO:2 indicated these sequences are likely to encode porin, which is a major whipworm excretory/secretory protein that has been described in the mouse parasite *Trichuris* muris and the human parasite *Trichuris trichiuria*, but that has not been identified in *Trichuris vulpis* until now.)

Previously, Zhan and colleagues described the molecular identification and partial characterization of ASP-5, which is an excretory/secretory protein of *Ancylostoma* (See Zhan et al., *International Journal for Parasitology* 33:897-907 (2003)). In their studies, the Zhan group described a single form of the ASP-5 protein having a mass of about 56 kDa, secreted from in vitro cultured parasites.

The ASP-5 protein including an N-terminal His6 tag (SEQ ID NO:33) may be encoded by the nucleic sequence of SEQ ID NO:31:

(SEQ ID NO: 31)
ATGGGCAGCAGCCATCATCATCATCATCACAGCAGCGGCCTGGTGCC

GCGCGGCAGCCATATGGCTAGCATGACTGGTGGACAGCAAATGGGTC

GCGGATCCGAATTCGAGCTCACCACTTGTCCAGGAAATGATCTAACA

GATGCTGAACGCACACTGCTAACTAGGGTGCACAATTCCATTCGACG

GGAAATAGCGCAAGGAGTTGCAAACAACTACCATGGTGGTAAACTGC

CTGCTGGAAAGAACATATACAGGATGAGATACAGCTGTGAGCTGGAA

CAGGCTGCTATTGATGCTAGTCAAACCTTCTGTTCCGCATCATTGGA

GGAACCACAGAAATATGGACAAAACATCCAAGCATACGTCACACCAT

CTATAATCGCTCGCCCGAAAAACGACCTTCTTGAAGATGCAGTGAAA

CAATGGTATCTGCCTGTTATCTACTACGGCCAACGCGACGCGGCCAA

CAAGTTCACCGATCCGCGCTTGTACACATTTGCAAACCTCGCCTACG

ACAAGAACACTGCACTTGGCTGTCACTATGCGAAATGTCAAGGCCCT

GACAGAATCGTCATTAGTTGCATGTACAACAACGTCGTTCCTGACAA

CGCTGTGATCTACGAGCCAGGAACTGCTTGCGTAAAAGATCAGGACT

GCACTACTTATCCTCAGTCCACATGCAAGGACAGCCTTTGCATTATT

CCTACGCCACATCCACCAAATCCACCAAATCCACCACCTGCAATGTG

TCCAAACGCTGAAATGACTGATGCAGCACGAAAGAAGGTCCTCGACA

TGCACAACTGGCGCAGATCGCAGCTCGCTCTGGGAAACGTTCAAAAC

GGGAAAAATGCTTACAACTGCCCCACTGCAACAGACATGTACAAGAT

GGAATATGATTGCGACCTCGAGAACAGCGCTCTAGCGTATGCAAAGC

AATGTAGTCTCGTTGGTTCAGCAGAAGGAACTCGTCCAGGAGAAGGC

GAGAATGTCCACAAAGGCGCTCTCGTAACCGATCCGGAGGCTGCAGT

TCAGACCGCAGTTCAAGCATGGTGGAGTCAAATCTCACAAAATGGAC

TCAATGCACAGATGAAATTCACTGCTTTCTTGAAGGACAAGCCTGAC

GCTCCGACAGCGTTTACACAGATGGCGTGGGCCAAATCCGTAAAGCT

TGGATGTGCTGTCTCTAATTGTCAGGCAGATACCTTCACCGTCTGTA

GATACAAAGCTGCCGGAAACATCGTGGGCGAATTCATCTATACCAAG

GGAAATGTATGCGACGCCTGTAAAGCCACATGCATTACCGCGGAAGG

TCTTTGCCCAACGCCTTGAGCGGCCGC

In an effort to identify tools for capturing and detecting hookworm and/or hookworm antigen in hookworm-infected mammals, the present inventors have determined that a modified protein of about 28 kDa, rather than the 56 kDa version, is present in the feces of canines that are infected by *Ancylostoma*. (This 28 kDa version of ASP5 is referred to herein as "CoproASP5"; the detection of CoproASP5 in feces of *Ancylostoma*-infected canines is described in the Example section included herein.) In one aspect, therefore, the present invention provides polypeptides that may be used to generate antibodies that may be used to specifically capture and detect CoproASP5. One such polypeptide that may be used to generate antibodies that may be used to bind CoproASP5 is referred to as ASP5-1 polypeptide, which may be encoded by the following nucleic acid sequence:

(SEQ ID NO: 32)
ATGGGCAGCAGCCATCATCATCATCATCACAGCAGCGGCCTGGTGCC

GCGCGGCAGCCATATGGCTAGCATGACTGGTGGACAGCAAATGGGTC

GCGGATCCGAATTCGAGCTCACCACTTGTCCAGGAAATGATCTAACA

GATGCTGAACGCACACTGCTAACTAGGGTGCACAATTCCATTCGACG

GGAAATAGCGCAAGGAGTTGCAAACAACTACCATGGTGGTAAACTGC

CTGCTGGAAAGAACATATACAGGATGAGATACAGCTGTGAGCTGGAA

CAGGCTGCTATTGATGCTAGTCAAACCTTCTGTTCCGCATCATTGGA

GGAACCACAGAAATATGGACAAAACATCCAAGCATACGTCACACCAT

CTATAATCGCTCGCCCGAAAAACGACCTTCTTGAAGATGCAGTGAAA

CAATGGTATCTGCCTGTTATCTACTACGGCCAGCGCGACGCGGCCAA

CAAGTTTACGGATCCGCGCTTGTACACATTTGCAAACCTCGCCTACG

ACAAGAACACTGCACTTGGCTGTCACTATGCGAAATGTCAAGGCCCT

GACAGAATCGTCATTAGTTGCATGTACAACAACGTCGTTCCTGACAA

CGCAGTGATCTACGAGCCTGGAACTGCTTGCGTAAAAGATGCGGACT

GCACTACTTATCCTCAGTCCACATGCAAGGACAGCCTTTGCATTATT

CCTACGCCACATCCACCAAATCCACCAAATCCACCACCAGCAATGAG

TCCATGAGCGGCCGC

A skilled artisan will appreciate that due to the degeneracy of the genetic code, nucleic acid sequences other than SEQ ID NO:32 can code for the polypeptide of SEQ ID NO:34 if appropriate (silent) codon substitutions are made.

Analysis of the roundworm sequences corresponding to SEQ ID NO:24 and SEQ ID NO:25 indicated that each one of these roundworm sequences contains a large open reading frame (ORF). Specifically, the large ORF of SEQ ID NO:24 corresponds to nucleotides 21 through 446 of SEQ ID NO:24 and is predicted to encode a roundworm polypeptide having the following amino acid sequence:

(SEQ ID NO: 26)
MLPITFLLAIIVGAAVAHRKCGPNEEWTECTGCEIKCGQGEQPCPMM

CRPPSCECMAGKGLRRTADGRCVPEAQCPKRMVKRDEKCGPNEKFLK

CRGCEGTCKERLVPCPRMCKPPGCECPASEGFVRNDKGECIKFDDCP

K.

Further, the large ORF of SEQ ID NO:25 corresponds to nucleotides 21 through 446 of SEQ ID NO:25 and is predicted to encode a roundworm polypeptide having the following amino acid sequence:

(SEQ ID NO: 27)
MLPLTFLLAFIVGAAVAHRKCGPNEEWTECTGCEMKCGEGETPCPMM

CRPPSCECMAGKGLRRTPDGRCVPEAQCPKHMVKRDEKCGKNEKFLK

CRGCEGTCKERLVPCPKMCKPPGCECPASEGFVRNDKHECIKFDDCP

K.

SEQ ID NO: 24, SEQ ID NO: 25, SEQ ID NO: 26, SEQ ID NO: 27, SEQ ID NO: 28, SEQ ID NO: 29 and SEQ ID NO: 30 are outlined in Provisional Application Ser. No. 61/128,076 filed May 19, 2008 which is incorporated by reference in its entirety.

Analysis of the whipworm sequences corresponding to SEQ ID NO:1 and SEQ ID NO:2 indicated that each one of these whipworm sequences contains a large ORF. Specifically, the large ORF of SEQ ID NO:1 corresponds to nucleotides 32 through 1147 of SEQ ID NO:1 and is predicted to encode a whipworm polypeptide having the following amino acid sequence:

(SEQ ID NO: 3)
MRLVFHAVIYLTLGFLTDAVREKRGKCPPEPPIAGNTIYCRDDFDCG

GRQKCCTIAEGRGCVPPYGEQHFEVVKPGHCPAIPAVTGMANFCNTD

GDCDGPKKCCLTSRGYDCTHPLHFPIQPQPPVGQCPPSKPRIPGKWV

DICAKHANCPDPEKCCDTEYGNRCMDVGLVPGQGERPGNCPNEPRIR

GTKYDCRRDDDCDGVQKCCFTVEGRECVEPSRKPLDKPGHCPPIPAD

VGSARYCDTDRDCDGPRKCCLSSRGYECKHPVHYPDRVEPLVGECPP

SRPRIPGKWVDICSKHANCPDPEKCCDTEYGNRCMDVGLVPGQGEKP

ANCPKEPRIRGTKYDCRRDDDCDGKQKCCYTTEGRECVHGIWP.

Further, the large ORF of SEQ ID NO:2 corresponds to nucleotides 1 through 1059 of SEQ ID NO:2 and is predicted to encode a whipworm polypeptide having the following amino acid sequence:

(SEQ ID NO: 4)
VREKRGKCPPEPPIAGNTIYCRDDFDCGGRQKCCTIAEGRGCVPPYG

EQDFEVVKPGHCPAIPAVTGMANFCNTDGDCDGPKKCCLTSRGYDCT

HPLHFPIQPQPPVGQCPPSKPRVPGKWVDICAKHANCPDPEKCCDTE

YGNRCMDVGLVAGQGERPGNCPNEPRIRGTKYDCRRDDDCDGVQKCC

FTVEGRECVEPSRKPLDKPGHCPPIPADVGSARYCDTDRDCDGPRKC

CLSSRGYECKHPVHYPDRVEPLVGECPPSRPRIPGKWVDICSKHANC

PDPEKCCDTEYGNRCMDVGLVPGQGEKPANCPKEPRIRGTKYDCRRD

DDCDGKQKCCYTTEGRECVHGIWP.

SEQ ID NO: 1, SEQ ID NO: 2, SEQ ID NO: 3, SEQ ID NO; 4, SEQ ID NO: 5, SEQ ID NO: 6, SEQ ID NO: 7, SEQ ID NO: 8, and SEQ ID NO: 9 are outlined in Provisional Application Ser. No. 61/128,077 filed May 19, 2008 which is incorporated by reference in its entirety.

Analysis of the roundworm sequences corresponding to SEQ ID NO:10 and SEQ ID NO:11 indicated that each one of these sequences contains a large ORF. Specifically, as shown in, the large ORF of SEQ ID NO:10 corresponds to nucleotides 2 through 616 of SEQ ID NO:11 and is predicted to encode a roundworm polypeptide having the following amino acid sequence:

(SEQ ID NO: 12)
KKIYGVAASRRRRHHFTLENSLDTHLKWLSHEQKEELLQMKKDGKS

KKELQDKIMHYYEHLEGDAKHEATEQLKGGCREILKHVVGEEKAAE

IKALKDSGASKDELKAKVEEALHAVTDEEKKQHIAEFGPACKKIYG

VAASRRRRHHFTLENSLDTHLKWLSHEQKEELLQMKKDGKSKKELQ

DKIMHYYEHLEGMLLALCILY.

Further, the large ORF of SEQ ID NO:11 corresponds to nucleotides 1 through 486 of SEQ ID NO:11 and is predicted to encode a roundworm polypeptide having the following amino acid sequence:

(SEQ ID NO: 13)
IYGVAASRRRRHHFTLEKSLDTHLKWLSHEQKEELLKMKKDGKSKKE

LQDKVMHFYEHLEGDAKHEATEQLKGGCREILKHVVGEEKAAEIKAL

KDSGASKDELKAKVEDALHAVTDEEKKQHIAEFGPACKEIFGVPIDV

RHKRDPYTNMTPDEVAEGLRS.

SEQ ID NO: 10, SEQ ID NO: 11, SEQ ID NO: 12, SEQ ID NO: 13, SEQ ID NO: 14, SEQ ID NO: 15, and SEQ ID NO: 16 are outlined in Provisional Application Ser. No. 61/128,079 filed May 19, 2008 which is incorporated by reference in its entirety.

Analysis of the roundworm sequences corresponding to SEQ ID NO:17 and SEQ ID NO:18 indicated that each one of these roundworm sequences contains a large open reading frame (ORF). Specifically, the large ORF of SEQ ID NO:17 corresponds to nucleotides 28 through 456 of SEQ ID NO:17 and is predicted to encode a roundworm polypeptide having the following amino acid sequence:

(SEQ ID NO: 19)
MLSVLALFALITFAVAGPESCGPNEVWTECTGCELKCGQDENTPCTL

NCRPPSCECSPGRGMRRTNDGRCIPASQCPQHRAKREEQCKPNEQWS

PCRGCEGTCAQRFVPCTRNCRPPGCECVAGAGFVRDAEGNCIKFDDC

PK.

Further, the large ORF of SEQ ID NO:2 corresponds to nucleotides 29 through 457 of SEQ ID NO:18 and is predicted to encode a roundworm polypeptide having the following amino acid sequence:

(SEQ ID NO: 20)
MLSVLALFALITFAVADPKSCGPNEVWTECTGCELKCGQDEDTPCTL

NCRPPSCECSPGRGMRRTDDGRCIPASQCPQHRAKREEQCKPNEQWS

PCRGCEGTCAQRFVPCTRNCRPPGCECVAGAGFVRDAAGNCIKFDDC

PK.

SEQ ID NO: 17, SEQ ID NO: 18, SEQ ID NO: 19, SEQ ID NO: 20, SEQ ID NO: 21, SEQ ID NO: 22, and SEQ ID NO: 23 are outlined in Provisional Application Ser. No. 61/128,099 filed May 19, 2008 which is incorporated by reference in its entirety Analysis of the hookworm sequences corresponding to SEQ ID NO: 31 and SEQ ID NO: 32 indicated that each one of these hookwormworm sequences contains a large open reading frame (ORF). Specifically, the large ORF of SEQ ID NO:31 is predicted to encode a hookworm polypeptide having the following amino acid sequence:

(SEQ ID NO: 33)
MGSSHHHHHHSSGLVPRGSHMASMTGGQQMGRGSEFELTTCPGNDLT

DAERTLLTRVHNSIRREIAQGVANNYHGGKLPAGKNIYRMRYSCELE

QAAIDASQTFCSASLEEPQKYGQNIQAYVTPSIIARPKNDLLEDAVK

QWYLPVIYYGQRDAANKFTDPRLYTFANLAYDKNTALGCHYAKCQGP

DRIVISCMYNNVVPDNAVIYEPGTACVKDQDCTTYPQSTCKDSLCII

PTPHPPNPPNPPPAMCPNAEMTDAARKKVLDMHNWRRSQLALGNVQN

GKNAYNCPTATDMYKMEYDCDLENSALAYAKQCSLVGSAEGTRPGEG

ENVHKGALVTDPEAAVQTAVQAWWSQISQNGLNAQMKFTAFLKDKPD

APTAFTQMAWAKSVKLGCAVSNCQADTFTVCRYKAAGNIVGEFIYTK

GNVCDACKATCITAEGLCPTP.

The first 38 amino acids of SEQ ID NO:33 are derived from a cloning vector, the skilled artisan will appreciate that this portion may be omitted or substituted with other suitable fusion partners.

Further, the large ORF of SEQ ID NO:32 is predicted to encode a hookworm polypeptide having the following amino acid sequence:

(SEQ ID NO: 34)
MGSSHHHHHHSSGLVPRGSHMASMTGGQQMGRGSEFELTTCPGNDLT

DAERTLLTRVHNSIRREIAQGVANNYHGGKLPAGKNIYRMRYSCELE

QAAIDASQTFCSASLEEPQKYGQNIQAYVTPSIIARPKNDLLEDAVK

QWYLPVIYYGQRDAANKFTDPRLYTFANLAYDKNTALGCHYAKCQGP

DRIVISCMYNNVVPDNAVIYEPGTACVKDADCTTYPQSTCKDSLCII

PTPHPPNPPNPPPAMSP.

The polypeptides of the present invention are encoded for by nucleic acids that have a nucleotide sequence that corresponds to all or portions of SEQ ID NO:1, SEQ ID NO: 2, SEQ ID NO: 10, SEQ ID NO: 11, SEQ ID NO: 17, SEQ ID NO: 18, SEQ ID NO: 24, SEQ ID NO: 25, SEQ ID NO: 31 and SEQ ID NO: 32 and all conservative variants of those sequences. It is to be understood therefore that the amino acid sequence of the polypeptide of the present invention is variable.

For example, the polypeptide of the present invention may have an amino acid sequence that corresponds to all or a portion of SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33 and SEQ ID NO: 34 or all or a portion of a conservative variant of SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33 and SEQ ID NO: 34.

In one specific example, the roundworm polypeptide of the present invention has the following amino acid sequence:

(SEQ ID NO: 28)
MHRKCGPNEEWTECTGCEIKCGQGEQPCPMMCRPPSCECMAGKGLRR

TADGRCVPEAQCPKRMVKRDEKCGPNEKFLKCRGCEGTCKERLVPCP

RMCKPPGCECPASEGFVRNDKGECIKFDDCPK.

In one specific example, the whipworm polypeptide of the present invention has the following amino acid sequence:

(SEQ ID NO: 5)
MVREKRGKCPPEPPIAGNTIYCRDDFDCGGRQKCCTIAEGRGCVPPY

GEQHFEVVKPGHCPAIPAVTGMANFCNTDGDCDGPKKCCLTSRGYDC

THPLHFPIQPQPPVGQCPPSKPRIPGKWVDICAKHANCPDPEKCCDT

EYGNRCMDVGLVPGQGERPGNCPNEPRIRGTKYDCRRDDDCDGVQKC

CFTVEGRECVEPSRKPLDKPGHCPPIPADVGSARYCDTDRDCDGPRK

CCLSSRGYECKHPVHYPDRVEPLVGECPPSRPRIPGKWVDICSKHAN

CPDPEKCCDTEYGNRCMDVGLVPGQGEKPANCPKEPRIRGTKYDCRR

DDDCDGKQKCCYTTEGRECVHGIWP.

In another specific example, the roundworm polypeptide of the present invention has the following amino acid sequence:

(SEQ ID NO: 14)
MHHFTLENSLDTHLKWLSHEQKEELLQMKKDGKSKKELQDKIMHYYE

HLEGDAKHEATEQLKGGCREILKHVVGEEKAAEIKALKDSGASKDEL

KAKVEEALHAVTDEEKKQHIAEFGPACKKIYGVAAS.

In another specific example, the roundworm polypeptide of the present invention has the following amino acid sequence:

(SEQ ID NO: 21)
MGPESCGPNEVWTECTGCELKCGQDENTPCTLNCRPPSCECSPGRGM

RRTNDGRCIPASQCPQHRAKREEQCKPNEQWSPCRGCEGTCAQRFVP

CTRNCRPPGCECVAGAGFVRDAEGNCIKFDDCPK.

In another specific example, the hookworm polypeptide of the invention includes an amino acid sequence that is identical to or is homologous to a sequence represented by SEQ ID NO: 34.

The 125 amino acid residues that follow the N-terminal methionine residue of the roundworm polypeptide corresponding to SEQ ID NO: 28 specifically represent the amino acid residues 18 through 142 of SEQ ID NO:26. The N-terminal methionine was artificially added to the N-terminus of this polypeptide by carrying out a standard cloning technique. Antibody raised against the polypeptide corresponding to SEQ ID NO: 28 was useful for detecting roundworm antigen. Because the N-terminal methionine was artificially added, and is not thought to naturally exist in *Toxocara* (the residue that is immediately prior to the histidine residue at position 18 in each one of SEQ ID NO:26 and SEQ ID NO:27 is alanine, and not methionine), it is therefore contemplated that the polypeptide of the present invention may have an amino acid sequence that corresponds to amino acid residues 18 through 142 of SEQ ID NO:26, or, more specifically:

(SEQ ID NO: 29)
HRKCGPNEEWTECTGCEIKCGQGEQPCPMMCRPPSCECMAGKGLRRT

ADGRCVPEAQCPKRMVKRDEKCGPNEKFLKCRGCEGTCKERLVPCPR

MCKPPGCECPASEGFVRNDKGECIKFDDCPK.

The 353 amino acid residues that follow the N-terminal methionine residue of the whipworm polypeptide corresponding to SEQ ID NO:5 specifically represent the amino acid residues 20 through 353 of SEQ ID NO:3. The N-terminal methionine was artificially added to the N-terminus of this polypeptide by carrying out a standard cloning technique. Antibody raised against the polypeptide corresponding to SEQ ID NO:5 was useful for detecting whipworm antigen. Because the N-terminal methionine was artificially added, and is not thought to naturally exist in *Trichuris vulpis* (the residue that is immediately prior to the valine residue at position 20 in SEQ ID NO:3 is alanine), it is therefore contemplated that the polypeptide of the present invention may have an amino acid sequence that corresponds to amino acid residues 20 through 353 of SEQ ID NO:3, or, more specifically:

(SEQ ID NO: 6)
VREKRGKCPPEPPIAGNTIYCRDDFDCGGRQKCCTIAEGRGCVPPYG

EQHFEVVKPGHCPAIPAVTGMANFCNTDGDCDGPKKCCLTSRGYDCT

HPLHFPIQPQPPVGQCPPSKPRIPGKWVDICAKHANCPDPEKCCDTE

YGNRCMDVGLVPGQGERPGNCPNEPRIRGTKYDCRRDDDCDGVQKCC

FTVEGRECVEPSRKPLDKPGHCPPIPADVGSARYCDTDRDCDGPRKC

CLSSRGYECKHPVHYPDRVEPLVGECPPSRPRIPGKWVDICSKHANC

PDPEKCCDTEYGNRCMDVGLVPGQGEKPANCPKEPRIRGTKYDCRRD

DDCDGKQKCCYTTEGRECVHGIWP.

In another specific example, the whipworm polypeptide of the present invention has the following amino acid sequence:

(SEQ ID NO: 7)
MVREKRGKCPPEPPIAGNTIYCRDDFDCGGRQKCCTIAEGRGCVPPY

GEQDFEVVKPGHCPAIPAVTGMANFCNTDGDCDGPKKCCLTSRGYDC

THPLHFPIQPQPPVGQCPPSKPRVPGKWVDICAKHANCPDPEKCCDT

EYGNRCMDVGLVAGQGERPGNCPNEPRIRGTKYDCRRDDDCDGVQKC

CFTVEGRECVEPSRKPLDKPGHCPPIPADVGSARYCDTDRDCDGPRK

CCLSSRGYECKHPVHYPDRVEPLVGECPPSRPRIPGKWVDICSKHAN

CPDPEKCCDTEYGNRCMDVGLVPGQGEKPANCPKEPRIRGTKYDCRR

DDDCDGKQKCCYTTEGRECVHGIWP.

The 353 amino acid residues that follow the N-terminal methionine residue of the whipworm polypeptide corresponding to SEQ ID NO:7 specifically represent the amino acid residues 1 through 353 of SEQ ID NO:4. The N-terminal methionine was artificially added to the N-terminus of this polypeptide by carrying out a standard cloning technique. Antibody raised against the polypeptide corresponding to SEQ ID NO:7 was useful for detecting whipworm antigen. Because the N-terminal methionine was artificially added, it is therefore contemplated that the polypeptide of the present invention may have an amino acid sequence that corresponds to amino acid residues 1 through 353 of SEQ ID NO:4, or, more specifically:

(SEQ ID NO: 8)
VREKRGKCPPEPPIAGNTIYCRDDFDCGGRQKCCTIAEGRGCVPPYG

EQDFEVVKPGHCPAIPAVTGMANFCNTDGDCDGPKKCCLTSRGYDCT

HPLHFPIQPQPPVGQCPPSKPRVPGKWVDICAKHANCPDPEKCCDTE

YGNRCMDVGLVAGQGERPGNCPNEPRIRGTKYDCRRDDDCDGVQKCC

FTVEGRECVEPSRKPLDKPGHCPPIPADVGSARYCDTDRDCDGPRKC

CLSSRGYECKHPVHYPDRVEPLVGECPPSRPRIPGKWVDICSKHANC

PDPEKCCDTEYGNRCMDVGLVPGQGEKPANCPKEPRIRGTKYDCRRD

DDCDGKQKCCYTTEGRECVHGIWP.

The 129 amino acid residues that follow the N-terminal methionine residue of the roundworm polypeptide corresponding to SEQ ID NO: 14 specifically represent the amino acid residues 14 through 142 of SEQ ID NO: 12. The N-terminal methionine was artificially added to the N-terminus of this polypeptide by carrying out a standard cloning technique. Antibody raised against the polypeptide corresponding to SEQ ID NO: 14 was useful for detecting roundworm antigen. Because the N-terminal methionine was artificially added, and is not thought to naturally exist in *Toxocara* (the residue that is immediately prior to the histidine residue at position 14 in each one of SEQ ID NO: 12 and SEQ ID NO:13 is arginine, and not methionine), it is therefore contemplated that the polypeptide of the present invention may have an amino acid sequence that corresponds to amino acid residues 14 through 142 of SEQ ID NO: 12, or, more specifically:

(SEQ ID NO: 15)
HHFTLENSLDTHLKWLSHEQKEELLQMKKDGKSKKELQDKIMHYYEH

LEGDAKHEATEQLKGGCREILKHVVGEEKAAEIKALKDSGASKDELK

AKVEEALHAVTDEEKKQHIAEFGPACKKIYGVAAS.

With 128 amino acids, the roundworm protein DIV6728 (SEQ ID NO: 21) is about 14 kD in size and with a theoretical pI is about 6.54. This protein belongs to TIL superfamily, which is a group of serine protease inhibitors. In an effort to identify tools for capturing and detecting roundworm and/or roundworm antigen in roundworm-infected mammals, the present inventors have determined that only a truncated portion (about 7 kDa) of the full-length (14 kDa) protein, and therefore not the 14 kDa version, is present in the feces of canines that are infected by *T. canis*. (This 7 kDa truncated portion of DIV6728 is referred to herein as "Copro6728"; the detection of Copro6728 in feces of *T. canis*-infected canines is described in the Example section included herein.) In one aspect, therefore, the present invention provides polypeptides that may be used to generate antibodies that may be used to specifically capture and detect Copro6728.

The 127 amino acid residues that follow the N-terminal methionine residue of the roundworm polypeptide corresponding to SEQ ID NO: 21 specifically represent the amino acid residues 17 through 143 of SEQ ID NO: 19. The N-terminal methionine was artificially added to the N-terminus of this polypeptide by carrying out a standard cloning technique. Also as described throughout the Example section, antibody raised against the polypeptide corresponding to SEQ ID NO: 21 was useful for detecting roundworm antigen. Because the N-terminal methionine was artificially added, and is not thought to naturally exist in *Toxocara* (the residue that is immediately prior to the glycine residue at position 17 in each one of SEQ ID NO: 19 and SEQ ID NO: 20 is alanine, and not methionine), it is therefore contemplated that the polypeptide of the present invention may have an amino acid sequence that corresponds to amino acid residues 17 through 143 of SEQ ID NO:19, or, more specifically:

```
                                          (SEQ ID NO: 22)
GPESCGPNEVWTECTGCELKCGQDENTPCTLNCRPPSCECSPGRGM

RRTNDGRCIPASQCPQHRAKREEQCKPNEQWSPCRGCEGTCAQRFV

PCTRNCRPPGCECVAGAGFVRDAEGNCIKFDDCPK.
```

Further, an alignment of SEQ ID NO: 28 (mostly *Toxocara canis*-derived sequence; with the only exception being the N-terminal methionine residue) to SEQ ID NO: 27 (*Toxocara cati*-derived sequence) is shown in FIG. 14. Because antibody raised against a polypeptide having sequence corresponding to SEQ ID NO:28 was useful for detecting *Toxocara cati*, it is additionally contemplated that the polypeptide of the present invention may have the amino acid sequence corresponding to SEQ ID NO: 30, wherein the X at position 1 is M or absent, the X at position 2 is L or absent, the X at position 3 is P or absent, the X at position 4 is L or absent (or the X at position 4 is I, which occupies position 4 of SEQ ID NO:26), the X at position 5 is T or absent, the X at position 6 is F or absent, the X at position 7 is L or absent, the X at position 8 is L or absent, the X at position 9 is A or absent, the X at position 10 is F or absent (or the X at position 10 is I, which occupies position 10 of SEQ ID NO:26), the X at position 11 is I or absent, the X at position 12 is V or absent, the X at position 13 is G or absent, the X at position 14 is A or absent, the X at position 15 is A or absent, the X at position 16 is V or absent, the X at position 16 is M or A, the X at position 35 is I or M, the X at position 39 is Q or E, the X at position 42 is Q or T, the X at position 65 is A or P, the X at position 78 is R or H, the X at position 88 is P or K, the X at position 111 is R or K, and the X at position 132 is G or H.

Further, an alignment of SEQ ID NO:3 with respect to SEQ ID NO:4 is shown in FIG. 5. It is additionally contemplated that the polypeptide of the present invention may have the amino acid sequence corresponding to SEQ ID NO:9, wherein the X at position 1 is M or absent, the X at position 2 is R or absent, the X at position 3 is L or absent, the X at position 4 is V or absent, the X at position 5 is F or absent, the X at position 6 is H or absent, the X at position 7 is A or absent, the X at position 8 is V or absent, the X at position 9 is I or absent, the X at position 10 is Y or absent, the X at position 11 is L or absent, the X at position 12 is T or absent, the X at position 13 is L or absent, the X at position 14 is G or absent, the X at position 15 is F or absent, the X at position 16 is L or absent, the X at position 17 is T or absent, the X at position 18 is D or absent, the X at position 19 is A or is absent (or the X at position 19 is M, which occupies position 19 of SEQ ID NO:5), the X at position 69 is H or D, the X at position 136 is I or V and the X at position 172 is P or A.

Further, an alignment of SEQ ID NO:14 (mostly *Toxocara canis*-derived sequence; with the only exception being the N-terminal methionine residue) to SEQ ID NO:13 (*Toxocara cati*-derived sequence) is shown in FIG. 8. Because antibody raised against a polypeptide having sequence corresponding to SEQ ID NO: 14 was useful for detecting *Toxocara cati*, it is additionally contemplated that the polypeptide of the present invention may have the amino acid sequence corresponding to SEQ ID NO:16, wherein the X at position 1 is I or absent, the X at position 2 is Y or absent, the X at position 3 is G or absent, the X at position 4 is V or absent, the X at position 5 is A or absent, the X at position 6 is A or absent, the X at position 7 is S or absent, the X at position 8 is R or absent, the X at position 9 is R or absent, the X at position 10 is R or absent, the X at position 11 is R or M, the X at position 18 is N or K, the X at position 37 is Q or K, the X at position 52 is I or V, X at position 55 is Y or F, the X at position 110 is E or D, the X at position 133 is K or E, the X at position 135 is Y or F, the X at position 138 is A or P, the X at position 139 is A or I, the X at position 140 is S or D, the X at position 141 is V or absent, the X at position 142 is R or absent, the X at position 143 is H or absent, the X at position 144 is K or absent, the X at position 145 is R or absent, the X at position 146 is D or absent, the X at position 147 is P or absent, the X at position 148 is Y or absent, the X at position 149 is T or absent, the X at position 150 is N or absent, the X at position 151 is M or absent, the X at position 152 is T or absent, the X at position 153 is P or absent, the X at position 154 is D or absent, the X at position 155 is E or absent, the X at position 156 is V or absent, the X at position 157 is A or absent, the X at position 158 is E or absent, the X at position 159 is G or absent, the X at position 160 is L or absent, the X at position 161 is R or absent, and the X at position 162 is S or absent.

Further, an alignment of SEQ ID NO: 21 (mostly *Toxocara canis*-derived sequence; with the only exception being the N-terminal methionine residue) to SEQ ID NO: 20 (*Toxocara cati*-derived sequence) is shown in FIG. 11. Because antibody raised against a polypeptide having sequence corresponding to SEQ ID NO: 21 was useful for detecting *Toxocara cati*, it is additionally contemplated that the polypeptide of the present invention may have the amino acid sequence corresponding to SEQ ID NO:23, wherein the X at position 1 is absent or M, the X at position 2 is absent or L, the X at position 3 is absent or S, the X at position 4 is absent or V, the X at position 5 is absent or L, the X at position 6 is absent or A, the X at position 7 is absent or L, the X at position 8 is absent or F, the X at position 9 is absent or A, the X at position 10 is absent or L, the X at position 11 is absent or I, the X at position 12 is absent or T, the X at position 13 is absent or F, the X at position 14 is absent or A, the X at position 15 is absent or V, the X at position 16 is M or A, the X at position 17 is G or D, the X at position 19 is E or K, the X at position 42 is N or D, the X at position 66 is N or D, and the X at position 132 is E or A.

A polypeptide of the present invention may have the amino acid sequence corresponding to SEQ ID NO:38, wherein the amino acid at position 54 is E or A. Antibodies that specifically bind to this polypeptide are included in the invention.

Because the first 38 amino acid residues of the polypeptide having the amino acid sequence that corresponds to SEQ ID NO: 34 were not derived from *Ancylostoma* (i.e., they are vector sequence), it is further contemplated that the peptide of the present invention may include an amino acid sequence that is identical to or is homologous to a sequence represented by SEQ ID NO: 34, wherein the X at position 1 is M or absent, the X at position 2 is G or absent, the X at position 3 is S or absent, the X at position 4 is S or absent, the X at position 5 is H or absent, the X at position 6 is H or absent, the X at position 7 is H or absent, the X at position 8 is H or absent, the X at position 9 is H or absent, the X at position 10 is H or absent, the X at position 11 is S or absent, the X at position 12 is S or absent, the X at position 13 is G or absent, the X at position 14 is L or absent, the X at position 15 is V or absent, the X at position 16 is P or absent, the X at position 17 is R or absent, the X at position 18 is G or absent, the X at position 19 is S or absent, the X at position 20 is H or absent, the X at position 21 is M or absent, the X at position 22 is A or absent, the X at position 23 is S or absent, the X at position 24 is M or absent, the X at position 25 is T or absent, the X at position 26 is G or absent, the X at position 27 is G or absent, the X at position 28 is Q or absent, the X at position 29 is Q or absent, the X at position 30 is M or absent, the X at position 31 is G or absent, the X at position 32 is R or absent, the X at position 33 is G or absent, the X at position 34 is S or absent, the X at position 35 is E or absent, the X at position 36 is F or absent, the X at position 37 is E or absent, and the X at position 38 is L or absent. Furthermore, because the S at position 251 in the SEQ ID NO:33 was artificially substituted during the cloning process described in the Example section herein in that sequence (the ASP5 protein of wild-type *Ancylostoma* includes a C residue at that position), it is contemplated that the X at position 251 of SEQ ID NO:34 may be either S or C.

It is also contemplated that any one or more of the SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33 and SEQ ID NO: 34 may be only a portion of a larger polypeptide sequence, and therefore may represent partial sequence of one or more proteins that normally are expressed in roundworm, for example, or one or more polypeptide sequences that are artificially fused to SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, or SEQ ID NO: 38, or Copro6728. The skilled artisan will recognize that are a variety of techniques exist for artificially fusing two or more polypeptide fragments together.

It is even further contemplated that the polypeptide of the present invention may include more than one of the SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33 SEQ ID NO: 34, SEQ ID NO: 38, and Copro6728. For example, the polypeptide of the present invention may include the SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, or SEQ ID NO: 38, or Copro6728. Also, it is contemplated that the polypeptide of the present invention may include a plurality of polypeptide fragments corresponding to SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, or SEQ ID NO: 38, or Copro6728. For example, the polypeptide of the present invention may be formed by a plurality of polypeptide fragments corresponding to SEQ ID NO:5, SEQ ID NO: 14, SEQ ID NO: 21, or SEQ ID NO: 28 that are fused together. In another example, the polypeptide of the present invention may be formed by a plurality of polypeptide fragments corresponding to SEQ ID NO:5 SEQ ID NO: 14, SEQ ID NO: 21, or SEQ ID NO: 28 and a plurality of polypeptide fragments corresponding to SEQ ID NO:7, SEQ ID NO: 16, SEQ ID NO: 23, or SEQ ID NO: 30 that are fused together in any combination.

Whereas one particular polypeptide of the present invention was expressed and isolated by a specific technique (in which is described in the Example section included herein), the skilled artisan will recognize that any of the polypeptides of the present invention may be isolated by employing any one or more of a variety of techniques. (See, e.g., Sewald and Jakubke, *Peptides: Chemistry and Biology*, Wiley Publishing (2002); *Peptide Synthesis and Applications* (*Methods in Molecular Biology*) Howl, ed., Humana Press (2005); Jones, *Amino Acid and Peptide Synthesis*, Oxford University Press (2002), each one of which is incorporated herein by reference in its entirety.) These techniques include those that may be carried out to isolate naturally existing polypeptides having amino acid sequence corresponding to SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, SEQ ID NO: 38, and Copro6728 and any naturally occurring variant of those polypeptides. These techniques further include those that may be carried out to artificially generate the polypeptides having amino acid sequence corresponding to SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, SEQ ID NO: 38, and Copro6728 and any conserved variant of those polypeptides. Such variants may be generated, for example, by employing any one or more mutagenesis techniques or by direct synthesis.

The polypeptides of the present invention are capable of eliciting an immune response in a host animal that is exposed to these polypeptides to produce one or more of the antibodies of the present invention. Regardless of the technique by which they are derived, the polypeptides of the present invention are preferably prepared in substantially pure form when they are to be used for the purpose of raising antibody. Preferably, these polypeptides are at least about 80% pure, more preferably are at least about 90-95% pure, and even more preferably are at least about 99% pure. Exemplary techniques for eliciting an immune response in a host organism and for isolating antibodies therefrom are described herein, but it is to be understood that the present invention is not limited to those techniques. The skilled artisan will recognize that there are a plurality of techniques for achieving this same goal without deviating from the scope and spirit of the invention.

IV. Antibodies of the Invention

The present invention further includes antibodies and antigen-binding fragments thereof that are raised against and that specifically bind all or part of one or more polypeptides of the present invention, and also includes compositions that include said antibodies and antigen-binding fragments thereof. When contacted to a sample obtained from a mammal, these antibodies and antigen-binding fragments are able to specifically bind to a particular helminthic worm antigen.

For example the roundworm antibodies and antigen-binding fragments are able to specifically bind roundworm antigens present in the sample, but are not able to specifically bind any antigen from hookworm or whipworm that may be present in the sample. As a further example, the whipworm antibodies and antigen-binding fragments are able to specifically bind whipworm antigens present in the sample, but are not able to specifically bind any antigen from hookworm or roundworm that may be present in the sample. The antibodies of the present invention are suitable for being used only to capture one or more roundworm antigens, whipworm antigens and/or hookworm antigens, only to detect one or more roundworm antigens, whipworm antigens and/or hookworm antigens, or more preferably, to both capture and detect one or more roundworm antigens, whipworm antigens and/or hookworm antigens.

The antibodies of the present invention may belong to any antibody class, including for example, IgG, IgM, IgA, IgD and IgE, and may be prepared by any of a variety of techniques known to the skilled artisan. (See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992); Harlow and Lane, *Antibodies: A Laboratory Manual*, Cold Spring Harbor Laboratory (1988); and *Making and Using Antibodies: A Practical Handbook*, Howard and Kaser, eds., CRC Press (2006), each one of which is incorporated herein by reference in its entirety.)

In one technique, the polypeptide of the invention is introduced into a host animal, such as into rabbit, mouse, rat, guinea pig, goat, pig, cow, sheep, donkey, dog, cat, chicken, or horse, for example. An enhanced immune response may be elicited in the host animal by associating the polypeptide with a carrier and/or by exposing the host to an adjuvant, but it is to be understood that the present invention does not require that the polypeptide be associated with a carrier or that the host be exposed to the adjuvant. An exemplary carrier that may be used for this purpose is bovine serum albumin, bovine thyroglobulin, and soybean trypsin inhibitor. Exemplary adjuvants include Freund's complete or incomplete adjuvant and MDL-TDM adjuvant. Regardless of whether the polypeptide is associated with such a carrier or whether the host is exposed to an adjuvant, booster immunizations optionally may be made with the host animal being bled one or more times thereafter. Polyclonal antibodies that specifically bind the polypeptide may then be purified from antisera obtained from the bleed or bleeds. Such purification may be achieved, for example, by employing affinity chromatography techniques that involve associating the polypeptide to a solid support. Such affinity chromatography techniques are well known by the skilled artisan.

In several embodiments, the roundworm antibody of the present invention is an antibody that is raised in rabbit by immunizing that host animal with the polypeptide having the amino acid sequence corresponding to SEQ ID NO: 28, SEQ ID NO: 14, and SEQ ID NO:21, (Hereinafter, these particular antibodies are referred to as "anti-DIV6744,", "anti-DIV6716," and "anti-DIV6728 respectively) The skilled artisan will recognize that the production and isolating of anti-DIV6744, anti-DIV6716 and anti-DIV6728, or any other antibody of the present invention, is not limited to any specific technique.

In another embodiment, the roundworm antibody of the present invention is an antibody that is raised in rabbit by immunizing that host animal with a polypeptide having the amino acid sequence corresponding to 6728C (SEQ ID NO:38). (Hereinafter, this particular antibody is referred to an "anti-Copro6728C".) A specific technique for producing and isolating this antibody is described in the Example section herein, but the skilled artisan will recognize that the production and isolating of anti-Copro6728C is not limited to that specific technique.

In additional embodiments, the roundworm antibody of the present invention is an antibody that is raised in rabbit by immunizing that host animal with extract of whole roundworm, extract of roundworm intestine, or extract of roundworm reproductive organs, as described in U.S. application Ser. No. 11/763,592 entitled "Roundworm Coproantigen Detection", filed Jun. 15, 2007.

In a further embodiment, the whipworm antibody of the present invention is an antibody that is raised in rabbit by immunizing that host animal with the polypeptide having the amino acid sequence corresponding to SEQ ID NO:5 or SEQ ID NO:7 (Hereinafter, this particular antibody is referred to as "anti-DIV6901" or "anti-DIV6902".) The skilled artisan will recognize that the production and isolating of anti-DIV6901, anti-DIV6901 or any other antibody of the present invention, is not limited to any specific technique.

In another embodiment, a hookworm antibody of the present invention is an antibody that is raised in rabbit by immunizing that host animal with the polypeptide having the amino acid sequence corresponding to SEQ ID NO: 34. (Hereinafter, this particular antibody is referred to as "anti-Asp5-1".) The skilled artisan will recognize that the production and isolating of anti-Asp5-1, or any other antibody of the present invention, is not limited to any specific technique.

In an additional embodiment, the hookworm antibody of the present invention is an antibody that is raised in rabbit by immunizing that host animal with the polypeptide having the amino acid sequence corresponding to SEQ ID NO:33, i.e. with substantially the full-length ASP5 protein from hookworm, as described in U.S. application Ser. No. 11/763,583 entitled "Device, Kit and Method for Hookworm Antigen Detection", filed Jun. 15, 2007.

In other embodiments, the antibodies of the present invention are raised in a host against one or more polypeptides having an amino acid sequence that is a conservative variant of the sequence corresponding to SEQ ID NO: 5, SEQ ID NO: 14, SEQ ID NO: 21, SEQ ID NO: 28, and SEQ ID NO: 34. In some other embodiments, the antibodies of the present invention are raised in a host against any one or more polypeptides having an amino acid sequence corresponding to the sequence of SEQ ID NO:3, SEQ ID NO: 4, SEQ ID NO: 6, SEQ ID NO: 7, SEQ ID NO: 8, SEQ ID NO: 9 SEQ ID NO:12, SEQ ID NO:13, SEQ ID NO: 15, SEQ ID NO: 16, SEQ ID NO: 19, SEQ ID NO: 20, SEQ ID NO: 22, SEQ ID NO: 23, SEQ ID NO: 26, SEQ ID NO: 27, SEQ ID NO: 29, SEQ ID NO: 30, SEQ ID NO:33, SEQ ID NO: 38, Copro6728 and CoproAP5, or one or more polypeptides having an amino acid sequence that is a conservative variant of any of those sequences.

In another embodiment, the antibodies of the present invention are antibodies that specifically bind one or more the polypeptides having the amino acid sequence corresponding to SEQ ID NO:3, SEQ ID NO:4, SEQ ID NO:5, SEQ ID NO:6, SEQ ID NO:7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, SEQ ID NO: 38, Copro6728 or CoproAP5, or antigenic portions thereof.

In yet other embodiments, the antibodies of the present invention specifically bind one or more polypeptides having an amino acid sequence that is a conservative variant of the sequence corresponding to SEQ ID NO:5, SEQ ID NO: 14, SEQ ID NO: 21, SEQ ID NO: 28, or SEQ ID NO: 34. In some other embodiments, the antibodies of the present invention specifically bind one or more polypeptides having an amino acid sequence corresponding to the sequence of SEQ ID NO:3, SEQ ID NO:4, SEQ ID NO:6, SEQ ID NO:7, SEQ ID NO: 8, SEQ ID NO: 9 SEQ ID NO:12, SEQ ID NO:13, SEQ ID NO: 15, SEQ ID NO: 16, SEQ ID NO: 19, SEQ ID NO: 20, SEQ ID NO: 22, SEQ ID NO: 23, SEQ ID NO: 26, SEQ ID NO: 27, SEQ ID NO: 29, SEQ ID NO: 30, SEQ ID NO:33, SEQ ID NO: 38, Copro6728 or CoproAP5, or one or more polypeptides having an amino acid sequence that is a conservative variant of any of those sequences.

It is also to be understood that the antibodies of the invention optionally may be polyclonal or monoclonal antibodies, single chain antibodies (scFv), chimeric antibodies, and fragments thereof. Monoclonal antibodies that are specific for the polypeptide of interest may be obtained and purified, for example, by preparing cell lines that generate antibodies having the desired specificity to the polypeptide of interest. Cell lines of this kind may be derived from cells of a particular type (e.g., spleen cells) that are isolated from a host animal that had previously been immunized with the polypeptide as described before. In such a case, these cells could then be immortalized, for example, by fusing them with myeloma cells by carrying out any one of a variety of fusion techniques known to the skilled artisan. In one exemplary technique, the cells from the immunized host animal are co-incubated with their fusion partner, e.g., the myeloma cells, in the presence of a detergent for a short period of time before being plated on a medium that supports the growth of hybrid cells (but not the myeloma fusion partner). Such selection may be achieved, for example, by using hypoxanthine, aminopterin, and thymidine (HAT). When hybrid cells emerge during selection, in perhaps one or two weeks after commencing the selection process, single hybrid colonies (and their supernatants) are tested for their ability to bind the polypeptide or polypeptides against which the host animal was immunized. Hybrid colonies having the most optimal binding specificity would represent the best candidates from which monoclonal antibodies may be isolated. These monoclonal antibodies, for example, may be isolated directly from the supernatant (i.e., medium) in which these colonies are grown by employing any one of a variety techniques known to the skilled artisan.

The antibodies of the invention also may be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments. In addition to production and purification from animals or mammalian cells, antibodies, antibody fragments, or non-antibody scaffolds can be selected based upon various in vitro technologies, including phage display, ribosomal display, or bacterial display.

Antibodies, including secondary antibodies, may be labeled with any type of label known in the art, including, for example, fluorescent, chemiluminescent, radioactive, enzymes, colloidal particles, radioisotopes and bioluminescent labels. In various embodiments of the invention, the one or more of the antibodies of the invention are labeled with an enzyme, a colloidal particle, a radionuclide or a fluorophor. The particulate label can be, for example, a colored latex particle, dye sol, or gold sol conjugated to an antibody.

Methods, Devices and Kits of the Invention

Devices and Kits of the Invention

The present invention, in one aspect, is a detecting the presence or absence of one or more helminthic antigens from a sample, the device comprising a solid support, wherein the solid support has immobilized thereon at least two antibodies selected from the group consisting of (a) a first antibody capable of specifically binding a roundworm coproantigen, but not a whipworm or hookworm coproantigen; (b) a second antibody capable of specifically binding a whipworm coproantigen, but not a roundworm or hookworm coproantigen; and (c) a third antibody capable of specifically binding a hookworm coproantigen, but not a whipworm or hookworm coproantigen; and optionally, (d) one or more types of roundworm coproantigen, whipworm coproantigen, and/or hookworm coproantigen, wherein the one or more types of roundworm coproantigen, whipworm coproantigen, and hookworm coproantigen are specifically bound to the antibodies. The device is arranged to aid specifically binding and isolating helminthic coproantigens from roundworm, whipworm and hookworm in a sample from a mammal.

In one aspect, the device includes a solid support, wherein one or more antibodies of the invention are immobilized on the solid support. The solid support may be, but is not limited to being, the inner, bottom surface of a well of a microtiter plate or a substrate that is included as part of a lateral flow device, for example. An exemplary microtiter plate is an Immulon 1B 96-well plate (which is commercially available from Thermo Scientific of Milford, Mass.), but it is to be understood that the skilled artisan will recognize that a large variety of other microtiter plates that are not the Immulon 1B 96-well plate allow for the immobilization of antibodies thereon, and therefore would be suitable for providing the solid support of the present invention.

An exemplary lateral flow device is the lateral flow device that is described in U.S. Pat. No. 5,726,010, which is incorporated herein by reference in its entirety. The device for performing a lateral flow assay may be a SNAP® device, which is commercially available from IDEXX Laboratories, Inc. of Westbrook, Me. However, it is to be understood that the skilled artisan will recognize that a large variety of other lateral flow devices that are not SNAP® devices or described by U.S. Pat. No. 5,726,010 allow for the immobilization of an antibody thereon, and therefore would be suitable for being used as the device of the present invention. These devices can include, for example, lateral flow devices that use colloidal gold technology.

Antibodies used in the device of the invention may be immobilized on the solid support by any methodology known in the art, including, for example, covalently or non-covalently, directly or indirectly, attaching the antibodies to the solid support. Therefore, while these antibodies may be attached to the solid support by physical adsorption (i.e., without the use of chemical linkers), it is also true that these antibodies may be immobilized to the solid support by any chemical binding (i.e., with the use of chemical linkers) method readily known to one of skill in the art.

It is also to be understood that the solid support may be any suitable material for the immobilization of the antibodies of the invention. For example, the solid support may be beads, particles, tubes, wells, probes, dipsticks, pipette tips, slides, fibers, membranes, papers, natural and modified celluloses, polyacrylamides, agaroses, glass, polypropylene, polyethylene, polystyrene, dextran, nylon, amylases, plastics, magnetite or any other suitable material readily known to one of skill in the art.

The device optionally may include one or more labeled antigen capture reagents that may be mixed with a sample from a mammal prior to application to a device of the invention. When the labeled capture antigen reagent is included, the labeled antigen capture reagent may or may not be deposited or dried on a solid surface of the device. "Antigen capture reagent" refers to any compound that is specific for the antigen or antigens of interest. The labeled antigen capture reagent, whether added to the mammalian sample or pre-deposited on the device, may be, for example, a labeled antibody specific for a roundworm antigen, including, but not limited to, the antibodies of the present invention. In one example, anti-DIV6744 conjugated with horseradish peroxidase may be used as a labeled antigen capture reagent. In another example, anti-DIV6901 or anti-DIV6902 conjugated with horseradish peroxidase may be used as a labeled antigen capture reagent. In a further example, anti-DIV6716 conjugated with horseradish peroxidase may be used as a labeled antigen capture reagent. In a further example, anti-DIV6728 conjugated with horseradish peroxidase may be used as a labeled antigen capture reagent. In yet a further example, anti-Copro6728 conjugated with horseradish peroxidase may be used as a labeled antigen capture reagent.

The device also may optionally include a liquid reagent that transports (such as when the device is a SNAP® device, for example), or otherwise facilitates removal of (such as when the device includes a microtiter plate, for example), unbound material (e.g., unreacted portions of the mammalian sample, such as, for example, unreacted portions of fecal extract, and unbound antigen capture reagent) away from the reaction zone (solid phase). The liquid reagent may be a wash reagent and serve only to remove unbound material from the reaction zone, or it may include a detector reagent and serve to both remove unbound material and facilitate antigen detection. For example, in the case of an antigen capture reagent conjugated to an enzyme, the detector reagent includes a substrate that produces a detectable signal upon reaction with the enzyme-antibody conjugate at the reaction zone (solid phase). Alternatively, in the case of a labeled antigen capture reagent conjugated to a radioactive, fluorescent, or light-absorbing molecule, the liquid reagent acts merely as a wash solution facilitating detection of complex formation at the reactive zone by washing away unbound labeled reagent.

The liquid reagent may further include a limited quantity of an "inhibitor", i.e., a substance that blocks the development of the detectable end product. A limited quantity is defined as being an amount of inhibitor sufficient to block end product development until most or all excess, unbound material is transported away from the second region, at which time detectable end product is produced.

The device of the present invention may also include various binding reagents immobilized at locations distinct from the antigen capture reagent or reagents. For example, an immunoreagent (an antibody, antigen or polypeptide) that recognizes a species-specific (e.g., roundworm-specific) antibody portion of a labeled antibody or antigen capture reagent, or an enzyme portion of an enzyme-labeled reagent, can be included as a positive control to assess the viability of the reagents within the device. For example, a positive control may be an anti-horseradish peroxidase antibody that has been raised in, for example, goat or mouse. Additionally, a reagent, e.g., an antibody, isolated from a non-immune member of the species from which the antibody portion of the antigen-antibody complex was derived can be included as a negative control to assess the specificity of immunocomplex (i.e., antigen-antibody complex) formation.

In addition to being designed to specifically binding and isolating helminthic coproantigens from roundworm, whipworm and hookworm in a mammalian sample, the device of the invention optionally may be designed to allow one or more other diagnostic tests to be performed. For example, the solid support may also include reagents for the detection of one or more non-worm parasites, one or more viruses, one or more fungi, or one or more bacteria. The reagents for the detection of one or more non-worm parasites, one or more viruses, one or more fungi, or one or more bacteria may be, for example, one or more antibodies or one or more antigens recognized by antibodies specific for one or more non-worm parasites, one or more viruses, one or more fungi, or one or more bacteria.

In one embodiment, the device of the present invention is a microtiter plate that includes a plurality of wells, wherein each well includes a solid support having anti-DIV6744 pAB immobilized thereupon.

The plate may be used in conjunction with a method of the present invention to detecting the presence or absence of one or more helminthic coproantigens in a sample. For example, a roundworm infection may be diagnosed in a mammal by detecting one or more roundworm antigens with the anti-DIV6744 pAB, one or more whipworm antigens with the anti-DIV6902 pAB, and one or more hookworm antigens with the anti-Asp5-1 pAB, that is immobilized on the solid support. In one embodiment, the antigens that are detected are coproantigens. "Coproantigens" are any product or products of roundworm, whipworm or hookworm that are present in a fecal sample and that can specifically bind to antibodies. Coproantigens therefore may be whole worm, worm eggs, worm fragments, or products secreted, excreted or shed from worm or a combination thereof. Coproantigens further include the polypeptides of the present invention, such as the polypeptides having an amino acid sequence corresponding to SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, or SEQ ID NO: 38, polypeptides having an amino acid sequence that is a conservative variant of those sequences, and/or antigenic fragments of any such polypeptides, and CoproASP5 and Copro6728, for example.

The invention further includes assay kits (e.g., articles of manufacture) for detecting and distinguishing between roundworm, whipworm and/or hookworm in a mammalian sample. A kit therefore may include one or more devices and/or compositions of the present invention. For example, the kit may include anti-roundworm antibodies and means for determining binding of the antibodies to roundworm antigens, anti-whipworm antibodies and means for determining binding of the antibodies to whipworm antigens, and anti-hookworm antibodies and means for determining binding of the antibodies to hookworm antigens in the sample. In one particular example, such a kit includes the device having an immobilized anti-roundworm antibody, such as anti-DIV6744, an anti-whipworm antibody, such as anti-DIV6902, and an anti-hookworm antibody, such as anti-Asp5-1, for example, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, known to those of ordinary skill in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample. The present kit may further include instructions for carrying out one or more methods of the present invention, including instructions for using any device and/or composition of the present invention that is included with the kit.

B. Methods of the Invention

The present invention further includes methods for using one or more of the devices, kits and/or compositions of the present invention to detect the presence or absence of one or more helminthic antigens in a sample. The methods therefore may be carried out to detect the presence or absence of roundworm, whipworm and/or hookworm in a sample, such as, for example, a fecal sample, that is obtained from a mammal, including, but not limited to, a canine, feline, porcine, bovine or human. Further, the methods may be carried out to detect *Toxocara*, such as *T. canis* or *T. cati*, or *T. vitulorum*, *Ascaris*, such as *A. lumbricoides* or *A. suum*, *Anisakis*, such as *A. simplex*, *Pseudoterranova*, such as *P. decipiens*, *Trichuris* and/or *Trichocephalus*, such as *Trichuris vulpis*, *Trichuris campanula*, *Trichuris serrata*, *Trichuris suis*, *Trichuris trichiura*, *Trichuris discolor* and *Trichocephalus trichiuris*, *Ancylostoma caninum*, *Ancylostoma braziliense*, *Ancylostoma duodenal*, *Ancylostoma ceylanicum*, *Ancylostoma tubaeforme* and *Ancylostoma pluridentatum*, *Necator americanus*, and *Uncinaria stenocephala*, for example.

In the methods of the present invention, detection of roundworm, whipworm and/or hookworm may be accomplished by detecting the presence or absence of one or more roundworm, whipworm and/or hookworm antigens, such as Copro6728 and CoproASP5 or the polypeptides having an amino acid sequence corresponding to SEQ ID NO:3, SEQ ID NO: 4, SEQ ID NO: 5, SEQ ID NO: 6, SEQ ID NO: 7, SEQ ID NO: 8, SEQ ID NO: 9 SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO:33, SEQ ID NO: 34, or SEQ ID NO: 38 as well as antigenic fragments and/or conservative variants of those sequences, and CoproASP5, for example. When the sample under test for helminthic coproantigens is feces, the soluble portion of the feces may be collected by any protocol known in art. For example, in addition to the specific protocol described in the Example section herein, the soluble portions of the sample generally may be collected by using filtration, extraction, centrifugation, or simple mixing followed by gravimetric settling. The skilled artisan will recognize that there are a variety of ways of extracting and preparing non-fecal samples from a mammal as well. For example, the sample may be a bodily fluid that is naturally excreted or otherwise released by the mammal or that is artificially obtained from the mammal. Such artificial extraction may be carried out by milking the mammal or by injecting a syringe into the mammal and drawing the fluid into the syringe. Once obtained, the fluid optionally may be fractionated (for example, serum may be fractionated from whole blood as then used as the sample). As another example, the sample may be obtained by swabbing the mammal, such as the oral cavity of the mammal, for example. As yet another example, tissue sections may be obtained by biopsy.

The methods include contacting the mammalian sample with one or more antibodies specific for helminthic coproantigens under conditions that allow an antigen/antibody complex, i.e., an immunocomplex, to form. That is, an antibody specifically binds to a coproantigen present in the sample. The skilled artisan is familiar with assays and conditions that may be used to detect such antigen/antibody complex binding. For example, the antigen/antibody complex may be detected using a secondary antibody that binds to the antigen/antibody complex. The formation of a complex between antigen and antibodies in the sample may be detected using any suitable method known in the art.

Further, the relative amount of antibody-antigen complexes that are formed in one particular reaction may be measured with respect to those formed in any other reaction by any methodology known in the art for achieving that goal. When it is determined that a sample under test has a specific (roundworm, whipworm and/or hookworm) antibody-antigen complexes, it can be concluded, based upon the specific complexes formed, that a specific helminth is present in the host mammal and which helminth is present (roundworm, whipworm and/or hookworm). When this is true, it may be concluded that the mammal from which the test sample was obtained harbors an intestinal helminth infection. The conclusions that the mammal being tested harbors an intestinal helminth infection may be made by a clinician at a diagnostic service provider or by a caregiver of the mammal, such as the mammal's veterinarian, for example. When a caregiver of a mammal determines (or is otherwise informed that) a mammal harbors a helminth infection and which helminth is present, the caregiver may then subject the mammal to a course of treatment that is optimally designed to rid the mammal of the helminth specifically, rather than of a parasitic nematode infection generally. Further, the present invention can be used to confirm that any animal that has received treatment for the specific helminth infection has been rid of that infection. A caregiver who learns that a sample includes both roundworm and whipworm, but not hookworm, for example, could use that knowledge to treat the mammal from which the sample was taken specifically for roundworm by administering to that mammal a drug optimally effective against roundworm and a second drug optimally effective against whipworm. Absent such knowledge, the caregiver may, for example, otherwise treat the mammal with a drug that is optimally effective against only roundworm, only whipworm, or neither roundworm nor whipworm (in such cases, the mammal would be at risk of receiving suboptimal treatment). In addition, humans who may come in contact with the infested animal or its excretions may be advised to take precautions against acquiring the parasite or parasites. In this context, it is important to determine the worm species with high specificity, as some helminths, such as roundworms and hookworms, can cause significant disease (e.g., larval migrans) in humans, while it is generally accepted that whipworm does not play a zoonotic role of importance in humans.

The steps of the method of the present invention may include applying a mammalian sample to a device of the invention, which includes a first antibody capable of specifically binding a roundworm coproantigen, but not a whipworm or hookworm coproantigen; a second antibody capable of specifically binding a whipworm coproantigen, but not a roundworm or hookworm coproantigen; and a third antibody capable of specifically binding a hookworm coproantigen, but not a whipworm or hookworm coproantigen to form antibody-coproantigen complexes in the presence of the coproantigens, if any, in the sample; and detecting the presence or absence of the antibody-coproantigen complexes, if any. Antibodies specific for antigens of roundworms may be directly or indirectly attached to a solid support or a substrate such as a microtiter well, antibody-immobilizing portion of a SNAP® device, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials may be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

The methods of the present invention do not require the use of solid phases or substrates, however. The skilled artisan will recognize that there are a number of ways that the present method may be carried out to detect the presence or absence of roundworm without involving the use of solid phases or substrates. In just one example, immunoprecipitation methods that do not require the use of solid phases or substrates may be carried out.

In some embodiments of the invention, the antigen/antibody complex is detected when an indicator reagent, such as an enzyme conjugate, which is bound to the antibody, catalyzes a detectable reaction. Optionally, an indicator reagent including a signal generating compound may be applied to the antigen/antibody complex under conditions that allow formation of a detectable antigen/antibody/indicator complex. Optionally, the antibody may be labeled with an indicator reagent prior to the formation of an antigen/antibody complex.

The formation of an antigen/antibody complex or an antigen/antibody/indicator complex in some of the methods of the present invention specifically may be detected by radiometric, colorimetric, fluorometric, photometric, size-separation, or precipitation methods. Detection of an antigen/antibody complex also may be accomplished by the addition of a secondary antibody that is coupled to an indicator reagent including a signal generating compound. Indicator reagents including signal generating compounds (labels) associated with a polypeptide/antibody complex may be detected using the methods described above and may include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Methods of the invention include, but are not limited to those based on competition, direct reaction or sandwich-type assays, including, but not limited to ELISA, RIA, immunofluorescent assays (IFA), hemagglutination (HA), fluorescence polarization immunoassay (FPIA), and microtiter plate assays (i.e., any assay done in one or more wells of a microtiter plate). One assay of the invention includes a reversible flow chromatographic binding assay, which may be performed, for example, by using a SNAP® device. See U.S. Pat. No. 5,726,010.

In some embodiments, the method of the invention facilitates sandwich or competition-type specific binding assays. In a sandwich assay, antigen capture reagents are immobilized in a reactive zone. These antigen capture reagents may specifically bind to antigens in the sample being tested for roundworm, whipworm and/or hookworm. Following binding of the antigen from the sample, the antigen capture reagent/antigen complex is detected by any suitable method. For example, the complex may be reacted with labeled specific binding reagents (e.g., an enzyme-antibody conjugate) and antigen detected (e.g., upon reaction with substrate).

In other embodiments of the method of the present invention, a competition assay is performed. In a competition assay, antigen capture reagents are immobilized at the reactive zone and are contacted simultaneously with antigen from a sample and labeled antigen (e.g., an antigen-enzyme conjugate). The amount of label detected at the reactive zone is inversely proportional to the amount of antigen in the sample.

In some embodiments of the method, antibodies specific for a roundworm, whipworm and hookworm coproantigens are attached to a solid phase or substrate. A sample potentially including an antigen from roundworm, whipworm and/or hookworm are added to the substrate. Antibodies that specifically bind roundworm, whipworm and/or hookworm are added. The antibodies may be the same antibodies used on the solid phase or they may be from a different source or species. Further, these antibodies may be linked to an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer, and/or the color may be subjectively assessed by the human eye.

In other embodiments of the method, antibodies specific for a roundworm, whipworm and hookworm coproantigens are attached to a solid phase or substrate. A sample potentially including a roundworm, whipworm and/or hookworm antigen is added to the substrate. Second anti-species antibodies that specifically bind the coproantigens are added. These second antibodies are from a different species than are the solid phase antibodies. Third anti-species antibodies that specifically bind the second antibodies and that do not specifically bind the solid phase antibodies are added. The third antibodies may include an indicator reagent, such as an enzyme conjugate. Wash steps may be performed prior to each addition. A chromophore or enzyme substrate may added and color may be allowed to develop. The color reaction may be stopped and the color may be quantified using, for example, a spectrophotometer, and/or the color may be subjectively assessed by the human eye.

In a specific example, the method of the present invention is performed in conjunction with a device that is a lateral flow assay device by adding a prepared mammalian sample to a flow matrix of the device at a first region (a sample application zone). The prepared sample is carried in a fluid flow path by capillary action to a second region of the flow matrix where a particulate label capable of binding and forming a first complex with an antigen in the sample exists. The particulate label can be, e.g., a colored latex particle, dye sol, or gold sol conjugated to an antibody specific for a roundworm antigen. The first complex is carried to a third region of the flow matrix where an antibody that specifically binds a roundworm antigen is immobilized at a distinct location. A second complex is formed between the immobilized antibody and the first complex. The particulate label that is part of the second complex can be directly visualized by the human eye.

Each specific helminth antibody may be an immobilized antigen capture reagent in a reaction zone (solid phase). A second antigen capture reagent, i.e., a second specific helminth antibody that has been conjugated to a label, either may be added to the sample before the sample is added to the device, or the second antigen capture reagent can be incorporated into the device. For example, the labeled antigen capture reagent may be deposited and dried on a fluid flow path that provides fluid communication between a sample application zone and the solid phase. Contact of the labeled antigen capture reagent with the test sample can result in dissolution of the labeled antigen capture reagent.

In one embodiment of the method of the present invention, specific helminthic coproantigen is detected by ELISA. Specific examples of the ELISA method of the present invention is described in the Example section included herein. Although the present invention is described with respect to those specific ELISA methods, however, it is to be understood that those of ordinary skill in the art will recognize that alternative, additional or substitute ELISA steps may be used without deviating from the basic goal achieved through this method of the invention.

In another embodiment of the present invention, helminthic coproantigen is detected by using a lateral flow device, such as a SNAP® device, for example.

Further, the methods of the invention for detection of helminth infection can be combined with other diagnostic assays to detect the presence of other organisms or conditions. For example, assays of the invention can be combined with reagents that detect one or more non-worm fecal parasites, one or more viruses, one or more fungi, one or more bacteria, one or more blood-borne parasites or occult blood or a combination thereof. By providing two or more unique binding sites in a single assay device (such as, for example, two unique spots on a SNAP® assay device), the present invention allows for detection of two or more organisms from a single sample. In one embodiment, there are three unique spots for detection of past or present infection or infestation from three organisms (the spots being either antigen or antibody binding reagents) from a single sample (i.e., the same individual sample is exposed to the three capture reagents on a single device). In yet another embodiment, there are four unique spots for detection of past or present infection or infestation from four organisms (the spots being either antigen or antibody binding reagents) from a single sample (i.e., the same individual sample is exposed to the four capture reagents on a single device. It is to be understood, however, that the same device may include more than four unique spots and/or allow for the detection of more than four organisms.

The reagents for the detection of one or more non-worm parasites, one or more viruses, one or more fungi, or one or more bacteria may be, for example, one or more antibodies or one or more antigens recognized by antibodies specific for one or more non-worm parasites, one or more viruses, one of more fungi, or one or more bacteria.

The method further may optionally include using one or more nucleic acids from roundworm, whipworm and hookworm, including, but not limited to, the nucleic acids of the present invention, to determine the presence or absence of roundworm, whipworm and/or hookworm in a mammalian sample. Such use of these nucleic acids for determining the presence of the helminth may be carried out before, after or concomitantly with the carrying out of any other aspects of the method, including the detection of roundworm, whipworm and hookworm by antibody. Therefore, in one aspect, after roundworm, whipworm and/or hookworm is detected or not detected in a particular sample and the mammal from which the sample was obtained is diagnosed as either having or not having a roundworm, whipworm and/or hookworm infection, the sample (or a later-obtained sample from the diagnosed mammal) may be tested for the presence or absence of any one or more of the nucleic acids, including any one or more nucleic acids of the invention. Anyone failing to detect a specific helminth in a particular mammal by using one or more nucleic acids (after the helminth had been detected by using one or more antibodies) would need to take into consideration the possibility that the antibodies had detected helminthic corpoantigen prior to the appearance of detectable helminthic nucleic acid in the sample. In such an instance, the mammal's caregiver may elect to ignore the observation that the nucleic acid had failed to detect the helminth and proceed with treating the mammal specifically for helminth infection based on the observation that the antibodies had in fact detected helminth. In another aspect, the nucleic acids are used to determine the presence or absence of helminths in a particular mammal, and then the presence or absence of helminths is further evaluated by using the antibodies of the present invention. Detection of one or more helminthic nucleic acids may be carried out by using any nucleic acid detection techniques known to the skilled artisan. For example, such detection may be carried out by performing a PCR-based technique, such as, but limited to, for example, a real-time PCR-based technique. Exemplary PCR-based techniques are described in, e.g., *PCR Protocols (Methods in Molecular Biology)*, $2^{nd}$ ed., Bartlett and Stirling, eds., Humana Press (2003); and Sambrook and Russell, *Molecular Cloning: A Laboratory Manual*, Cold Spring Harbor Laboratory Press (2001); each one of which is incorporated herein by reference in its entirety.

The present invention is specifically described with reference to five Examples; however, it is not to be construed as being limited thereto.

EXAMPLES

Unless otherwise indicated, the following materials and techniques were used to generate data described in one or more of Examples 1-4 as described below.

Polyclonal roundworm antibody preparation. The polyclonal antibodies "anti-DIV6728 pAB," (IgG) was raised in rabbit against a polypeptide having amino acid sequence corresponding to SEQ ID NO:21, respectively and purified from serum by using standard methods. Briefly, for anti-DIV6728 pAB nucleotides 76 through 456 of SEQ ID NO:17 were cloned in-frame into a vector (D8223, which is a derivative of pUC19) to create the plasmid D8245. Specifically, the 125 amino acids of SEQ ID NO: 21 that follow the methionine residue at the N-terminus of that sequence correspond to a portion of SEQ ID NO:19 and are encoded for by the cloned portion of SEQ ID NO:17. In the D8245 plasmid, the N-terminal methionine residue was encoded for by vector sequence at the junction of that plasmid where the vector was ligated to the cloned sequence from SEQ ID NO:17.

DNA sequence encoding SEQ ID NO:21 was then cleaved from the D8245 plasmid by restriction exonuclease digestion (NdeI and BamHI) and purified. This purified sequence was then ligated to linearized expression vector, pET28a, and the resulting circular construct (pTDX198::DIV6728) was transformed into BL21 (DE3) *E. coli* cells. (The complete sequence of the insert was confirmed by DNA sequence analysis.) Expression of His-tagged fusion protein was induced by addition of 1 mM IPTG to cultures of the transformed *E. coli*. Recombinant protein was solubilized in 6 M urea and purified by nickel affinity and ion exchange chromatography. (This recombinant protein is hereinafter is referred to as "rDIV6728".)

After rDIV6728 was introduced into rabbits, anti-DIV6728 pAB was purified from the plasma of the immunized rabbits by isolating IgG antibody by protein G affinity chromatography.

Polyclonal whipworm antibody preparation. The polyclonal antibody "anti-DIV6901 pAB" (IgG) was raised in rabbit against a polypeptide having amino acid sequence corresponding to SEQ ID NO:5 and purified from serum by using standard methods. Briefly, in the case of anti-DIV6901 pAB, nucleotides 89 through 1147 of SEQ ID NO:1 were cloned in-frame into an expression vector (D8223, which is a derivative of pUC19) to create the plasmid D9073. Specifically, the 353 amino acids of SEQ ID NO:5 that follow the methionine residue at the N-terminus of that sequence correspond to a portion of SEQ ID NO:3 and are encoded for by the cloned portion of SEQ ID NO:1.

DNA sequence encoding SEQ ID NO:5 was then cleaved from the D9073 plasmid by restriction exonuclease digestion (NdeI and BamHI) and purified. This purified sequence was then ligated to linearized expression vector, pET28a, and the resulting circular construct (ptDX233::DIV6901) was transformed into *E. coli* cells. (The complete sequence of the insert was confirmed by DNA sequence analysis.) Expression of His-tagged fusion protein was induced by addition of 1 mM IPTG to cultures of the transformed *E. coli*. Recombinant protein was solubilized in 6 M urea and purified by nickel affinity and ion exchange chromatography. (This recombinant protein is hereinafter is referred to as "rDIV6901".) Anti-DIV6901 pAB was purified from the plasma of the immunized rabbits by isolating IgG antibody by protein G affinity chromatography.

Polyclonal hookworm antibody preparation and isolation. The polyclonal antibody anti-ASP5-1 (IgG) was raised in rabbit against a polypeptide having amino acid sequence corresponding to SEQ ID NO: 34 and purified from serum by using standard methods. Briefly, nucleotides 50 through 427 of SEQ ID NO: 32 were cloned in-frame into a plasmid. Specifically, the 129 amino acids of SEQ ID NO: 34 that follow the methionine residue at the N-terminus of that sequence correspond to a portion of SEQ ID NO: 33 and are encoded for by the cloned portion of SEQ ID NO: 32. In the plasmid, the N-terminal methionine residue was encoded for by vector sequence at the junction of that plasmid where the vector was ligated to the cloned sequence from SEQ ID NO: 32.

DNA sequence encoding SEQ ID NO: 32 was then cleaved from the plasmid by restriction exonuclease digestion (NotI and SacI) and purified. This purified sequence was then ligated to linearized expression vector, pET28a, and the resulting circular construct was transformed into BL21 (DE3) *E. coli* cells. (The complete sequence of the insert was confirmed by DNA sequence analysis.) Expression of His-tagged fusion protein was induced by addition of 1 mM IPTG to cultures of the transformed *E. coli*. Recombinant protein was solubilized in 6 M urea and purified by nickel affinity and ion exchange chromatography. (This recombinant protein is hereinafter is referred to as "rASP5-1".)

After rASP5-1 was introduced into rabbits, anti-ASP5-1 pAB was purified from the plasma of the immunized rabbits by isolating IgG antibody by protein G affinity chromatography.

Infection of canine and feline animals. Parasitic nematode infection was effected by orally administering about 150-300 larvated eggs of roundworm (*Toxocara canis*), 150-300 infective larvae of hookworm (*Ancylostoma canium*), or 700 larvated eggs of whipworm (*Trichuris vulpis*), or any combination of the three to a healthy canine or feline. Infection was confirmed by microscopic observation of worm ova in fecal samples obtained from these host animals.

Canine and feline fecal sample preparation. Canine and feline animals known to be free of parasitic worm infection or to be infected with one, two or all three of roundworm, hookworm, or whipworm provided the source of fecal samples. Samples (approximately 1 gram) from frozen, unpreserved canine or feline fecal samples were suspended in 4 ml of diluent solution ("diluent solution" is 0.05 M Tris base; 1 mM EDTA; 0.45% Kathon; 16 mg/l gentamicin sulfate; 0.05% Tween-20; 40% fetal bovine serum; 10% rabbit serum; and 5% mouse serum). The suspension was centrifuged in a table-top centrifuge at 4000 rpm for 20 minutes to produce a first supernatant. The first supernatant was centrifuged at 10,000 g for 5 minutes to produce a second supernatant, which is referred to herein as "fecal extract".

ELISA assays. Purified anti-DIV6728 pAB, anti-DIV6901 pAB and anti-Asp5-1 pAB (100 μl/well; 3 μg/ml for Example 2) were immobilized by physical adsorption on Immulon 1B 96-well plates overnight at 4° C. The plates were then blocked with 1% BSA in 0.1M Tris pH 7.0 or 3 hours at room temperature, followed by 2.5% Sucrose in 0.1M Tris buffer, pH 7.0 for 3 hours at room temperature, aspirating the liquid, drying at room temperature. Approximately 100 μl of fecal extract was added to each well and allowed to incubate at room temperature for one hour. The wells were then washed five times with a PBS-Tween-20 solution according to standard methods known to those of ordinary skill in the art. In a separate reaction vessel, free anti-DIV6728 pAB, anti-DIV6901 pAB, and anti-Asp5-1 pAB was labeled with horseradish peroxidase (HRP) by using the crosslinker succinimidyl 4-[N-maleimidomethyl]cyclohexane-1-carboxylate (SMCC) to create a conjugate, and this conjugate (3 μg/ml for Examples 2) was added to each well having immobilized anti-DIV6728 pAB, anti-DIV6901 pAB, and anti-Asp5-1 pAB. Following a 30-minute incubation period at room temperature, unbound conjugate was washed from the wells by using PBS-Tween-20 solution according to standard methods known to those of ordinary skill in the art. 50 μl of TMBLUE® peroxidase substrate (SeraCare Life Sciences, West Bridgewater, Mass.) was then added to each well and the plates were incubated for 10 minutes at room temperature. After stopping each enzymatic reaction with 0.1% sodium dodecyl sulfate (SDS) following the 10-minute incubation period, the optical density (OD) value of each well of the 96-well plate was measured at A650 by standard spectrophotometric techniques by using an ELISA plate reader to generate an "OD650 value" (or, more simply, an "OD value") for each well. In this arrangement, the OD value obtained for any particular well of the 96-well plate was directly proportional to the amount of specifically bound antigen present in the well (if the IgG is not saturated).

Example 1

When tested by ELISA in a lateral flow format, anti-DIV6728 pAB specifically binds roundworm coproantigen, anti-DIV6901 pAB specifically binds whipworm coproantigen, and anti-Asp5-1 pAB specifically binds hookworm coproantigen. There was no cross coproantigen binding between the helminthic antibodies and their non-specific helminthics. The specific binding of roundworm coproantigen by anti-DIV6728 pAB, whipworm coproantigen by anti-DIV6901 pAB, and hookworm coproantigen by anti-Asp5-1 pAB produces a colorimetric change that is readily observable to the human eye.

It was a goal of Example 1 to determine whether anti-DIV6728 pAB, anti-DIV6901 pAB, and anti-Asp 5-1 pAB can be used to capture and specifically bind their respective helminthic coproantigens without non-specific binding in a lateral flow ELISA. The lateral flow format that was used was a SNAP® assay device, similar to that which is described in U.S. Pat. No. 5,726,010. Further, the assay was performed generally as described in that same patent. Briefly, among other components, the SNAP® assay device included a sample entry cup, a flow matrix, a sample prefilter pad for removing interfering particulate matter, a specific binding reagent pad, a reactive zone, and an absorbent reservoir. Anti-DIV6728 pAB, anti-DIV6901 pAB, and anti-Asp 5-1 pAB were immobilized in the form of small, round spots at the reactive zone by drying. The reactive zone was then blocked with BSA. A pooled fecal extract (150 µl) from roundworm-infected canines was mixed with 200 µl (1.0 µg/ml) conjugated anti-DIV6728 pAB, anti-DIV6901 pAB, or anti-Asp 5-1 pAB (the antibodies were affinity-purified before being labeled with HRP as described above. This mixture added to the sample cup and then was allowed to flow along the flow matrix. While in the flow matrix, the HRP labeled antibodies specifically bound to their respective helminthic coproantigens present in the fecal extract. The resulting complexes (i.e., those that included the HRP labeled antibodies and their respective helminthic coproantigens) were allowed to specifically bind to the immobilized anti-DIV6728 pAB, anti-DIV6901 pAB, or anti-Asp 5-1 pAB at the reaction zone. Flow along the flow matrix was reversed by contacting the absorbent reservoir with the flow matrix. At this time, detector and wash solution migrated into the flow matrix to remove any unbound components and to allow detection of any analyte complexes that were present where the capture reagent was immobilized onto the reaction zone. (This detection step lasted about eight minutes.) Stopping of the detection of the analyte complexes occurred by exposing the analyte complexes to 0.1% sodium azide.

As shown in FIG. 1C-E, detection of helminthic specific analyte complexes where the roundworm, whipworm, and hookworm specific antibodies were immobilized onto separate reaction zones was visibly apparent for a roundworm infection (1D), a whipworm infection (1E) and a hookworm infection (1C). In the negative control sample shown in FIG. 1A (diluent solution only), no analyte complexes were detected. In a negative control sample shown in FIG. 1B, no analyte complexes were detected where the antibody was immobilized onto the reaction zone of a separate device (the negative control sample was a pool of fecal extracts obtained from canines that did not harbor a helminth infection). These data therefore indicate that anti-DIV6728 pAB, anti-DIV6901 pAB, and anti-Asp 5-1 pAB can be used in a lateral flow ELISA format to separately and specifically bind their respective helminthic coproantigen. This specific binding is readily visible to the human eye.

Example 2

When tested by ELISA in a microtiter dish format, anti-DIV6728 pAB specifically binds roundworm coproantigen, but does not specifically bind coproantigen from either hookworm, whipworm or heartworm; anti-DIV6901 pAB specifically binds whipworm coproantigen, but does not specifically bind coproantigen from either hookworm, roundworm or heartworm; and anti-Asp5-1 pAB specifically binds hookworm coproantigen, but does not specifically bind coproantigen from either roundworm, whipworm or heartworm. The specific binding of roundworm coproantigen by anti-DIV6728 pAB, whipworm coproantigen by anti-DIV 6901 pAB, and hookworm coproantigen by anti-Asp5-1 pAB produces a colorimetric change that is readily observable to the human eye.

It was a goal of Example 2 to determine whether specific binding between anti-DIV6728 pAB and roundworm coproantigen; anti-DIV6901 pAB and whipworm coproantigen; and anti-Asp5-1 pAB and hookworm coproantigen, while the anti-DIV6728 pAB, anti-DIV6901 pAB, and anti-Asp5-1 pAB are immobilized on a solid support can produce a colorimetric change that is observable to the human eye.

Figure 2:
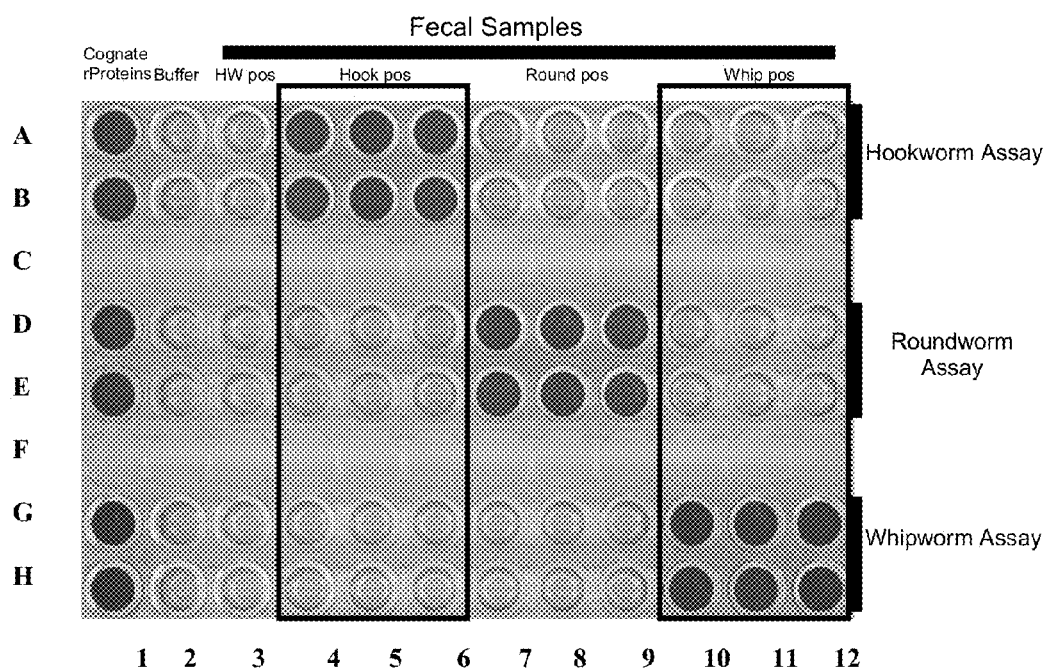
FIG. 2 shows the results of an ELISA assay, which was carried out by using a microtiter plate and which tested fecal samples from canines infected with either roundworm, hookworm, whipworm or heartworm by following the method of the present invention in a second Example

Referring to FIG. 2, anti-DIV6728 pAB (3 µg/ml) was immobilized onto the bottom surfaces of wells D1-D12 and E1-E12, anti-DIV6901 pAB was immobilized on the bottom surfaces of wells G1-G12 and H1-H12, and anti-Asp5-1 pAB was immobilized on the bottom surfaces of wells A1-A12 and B1-B12 of a microtiter plate as described before. Following such immobilization, the A3, B3, D3, E3, G3 and H3 wells were exposed to fecal extract from a heartworm-infected canine (indicated by "HW" in FIG. 2). The A4, B4, D4, E4, G4 and H4 wells were exposed to fecal extract from a first hookworm-infected canine, the A5, B5, D5, E5, G5, and H5 wells were exposed to fecal extract from a second hookworm-infected canine, and the A6, B6, D6, E6, G6, and H6 wells were exposed to fecal extract from a third hookworm-infected canine. The A7, B7, D7, E7, G7 and H7 wells were exposed to fecal extract from a first roundworm-infected canine, the A8, B8, D8, E8, G8, and H8 wells were exposed to fecal extract from a second roundworm-infected canine, and the A9, B9, D9, E9, G9, and H9 wells were exposed to fecal extract from a third roundworm-infected canine. The A10, B10, D10, E10, G10, and H10 wells were exposed to fecal extract from a first whipworm-infected canine, the A11, B11, D11, E11, G11, and H11 wells were exposed to fecal extract from a second whipworm-infected canine, and the A12, B12, D12, E12, G12, and H12 wells were exposed to fecal extract from a third whipworm-infected canine. The A1, B1, D1, E1, G1, and H1 wells were exposed to rDIV6728, rDIV6901, and rAsp5-1 (1 µg/ml), and therefore those wells served as positive controls. The A2, B2, D2, E2, G2, and H2 wells were not exposed to any fecal extract or to rDIV6728, rDIV6901, and rAsp5-1 and therefore those wells served as negative controls. After washing, wells D1-12 and E1-12 were exposed to HRP-labeled rDIV6728 pAB; wells G1-G12 and H1-H12 were exposed to HRP-labeled rDIV6901 pAB; wells A1-A12 and B1-B12 were exposed to HRP-labeled rAsp 5-1 pAB at 3 µg/ml as described above.

Following incubation of all of these wells with TMBLUE® peroxidase substrate and the subsequent addition of the SDS, colorimetric change was visually observed in the anti-DIV6728 pAB wells that had been exposed to fecal extract from roundworm-infected canines (D7-D9 and E7-E9), but no colorimetric change was observed in any of the anti-DIV6728 pAB wells that had been exposed to fecal extract from canines infected with either hookworm, whipworm or heartworm. Colorimetric change was visually observed in the anti-DIV6901 pAB wells that had been exposed to fecal extract from whipworm-infected canines (G10-G12 and H10-H12), but no colorimetric change was observed in any of the anti-DIV6901 pAB wells that had been exposed to fecal extract from canines infected with either hookworm, roundworm or heartworm. Colorimetric change was visually observed in the anti-Asp5-1 pAB wells that had been exposed to fecal extract from hookworm-infected canines (A4-A6 and B4-B6), but no colorimetric change was observed in any of the anti-Asp5-1 pAB wells that had been exposed to fecal extract from canines infected with either roundworm, whipworm or heartworm.

These data indicate that anti-DIV6728 pAB detects roundworm; anti-DIV6901 pAB detects whipworm; and anti-Asp5-1 pAB detects hookworm in an ELISA format sufficiently enough to produce a colorimetric change that is robust and readily visible to the human eye. Further, these data indicate that such colorimetric change allows the human eye to readily distinguish the between the helminthic specific fecal samples containing roundworm, hookworm and whipworm Example 3

A truncated version of DIV6728, Copro6728, is present in *T. canis* infected canine feces.

A. Canine Fecal Sample Preparation

Canine animals known to harbor a roundworm (*T. canis*) infection or to not have a parasitic worm infection provided the source of fecal samples. A sample (approximately 1 gram) of frozen, unpreserved canine feces pooled from five roundworm-infected or uninfected canines was suspended in 4 ml of extraction buffer ("extraction buffer" is 1× phosphate-buffered saline (PBS), pH 7.0-7.5 with 0.05% Tween-20). This suspension was vortexed for 2 minutes and then was centrifuged at 13,000 rpm for 25 minutes to produce a first supernatant. This first supernatant was then centrifuged at 10,000 rpm for 5 minutes to produce a second supernatant. This second supernatant hereinafter is referred to as "fecal extract".

B. Ion exchange

Figure 15:
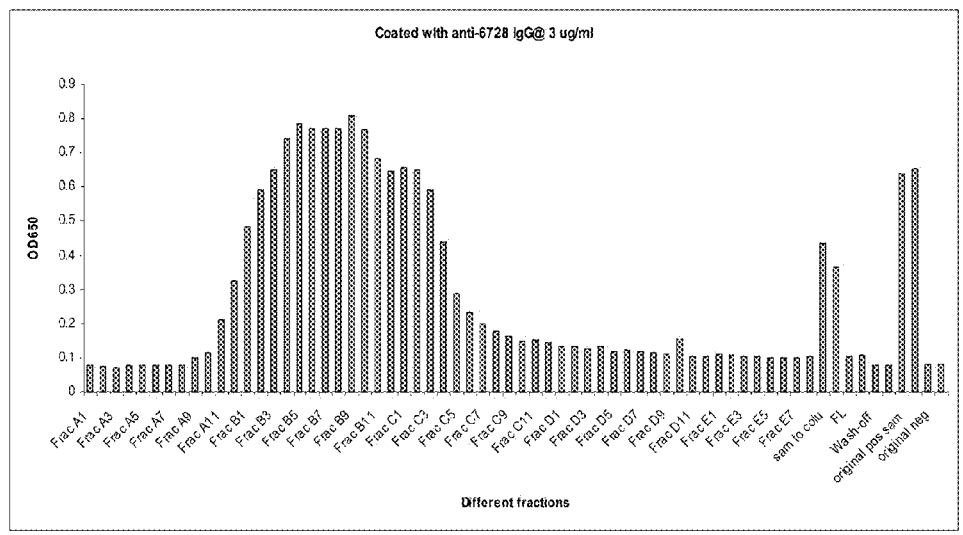
FIG. 15 shows an ELISA with elution fractions from SP columns as samples and that Copro6728 can be partially purified and enriched by eluting the SP column by following the method of the present invention in the third Example.

Ion exchange chromatography can enrich Copro6728 from a fecal sample. PLRS samples were used for this study. Fecal sample was extracted first with PBST (0.05% Tween 20), pH 7.3. Sample was diluted with sodium citrate buffer, pH 3.0 first and then the pH was adjusted to 3 with HCl. Finally, sample was centrifuged and the supernatant was loaded onto a sulfopropyl (SP) column. The SP column was eluted with 20 mM sodium citrate buffer, pH 3 with 1 M NaCl, and the elution fractions were evaluated by ELISA. The ELISA plate was coated with rabbit anti-6728 IgG at 3 μg/ml. Based on the results shown in FIG. 15, it is clear that Copro6728 can be partially purified and enriched by eluting the SP column with sodium citrate buffer with 1 M NaCl and Copro6728 is in the fraction between A11 and C9 (FIG. 15)

C. Western Blotting and SDS-PAGE

Figure 16:
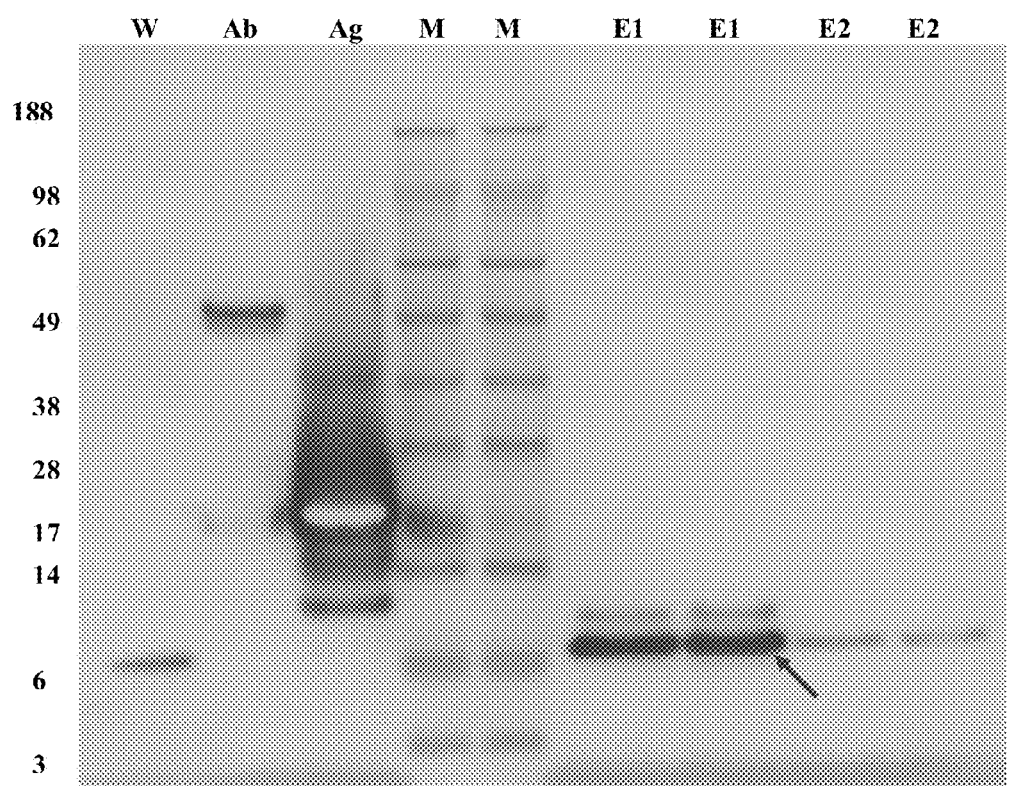
FIG. 16 shows that the molecular weight of Copro6728 was about 7KD using a western Blot probed with rabbit anti full-length DIV6728 IgG-HRP following the method of the present invention in the third Example.
Figure 17:
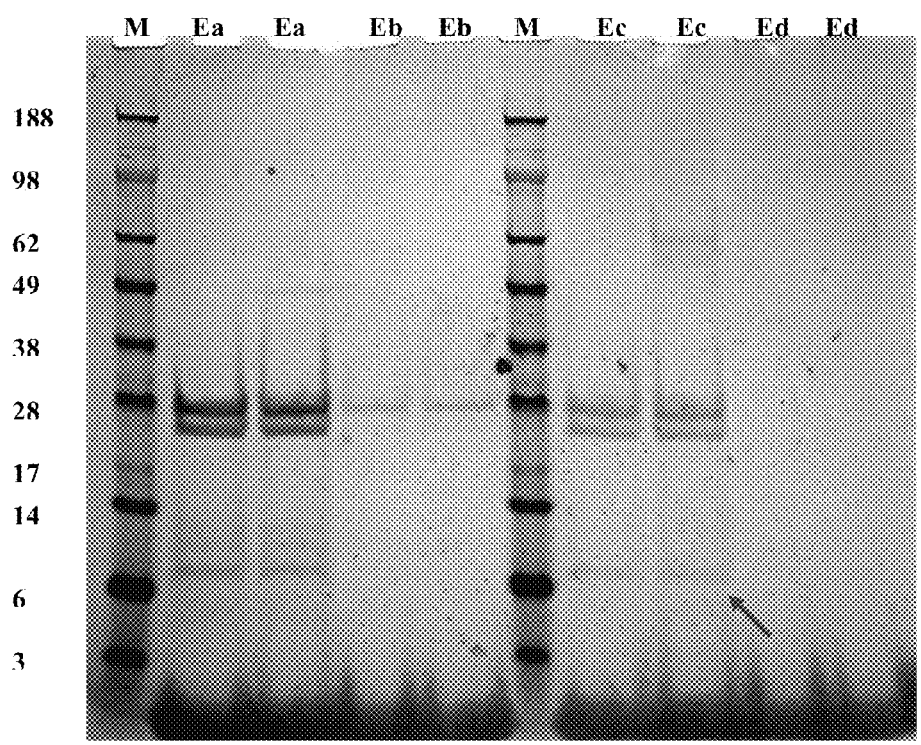
FIG. 17 shows that the molecular weight of Copro6728 was about 7KD using an SDS-PAGE gel stained with Imperial Protein Staining following the method of the present invention in the third Example.

Western blotting and SDS-PAGE gel showed that the molecular weight of Copro6728 is about 7 kD. Elution fractions from the SP column were mixed and buffer pH was adjusted to 7 with NaOH before loading onto an affinity column, which was prepared by linking the rabbit anti-6728 IgG with AminoLink resin (Pierce, Thermo Scientific). The column was washed and eluted according to manufacturer's instructions. Elution fractions were loaded to a 10 well 4-12% Bis-Tris gradient gel and transferred to nitrocellulose membrane for western blotting. Probed with rabbit anti-6728IgG-HRP, western blotting showed that the major band (Copro6728) is about 7 kD (red arrow on FIG. 16). After further concentration, the same samples were visualized on an SDS-PAGE gel with Imperial Protein Stain (Pierce, Thermo Scientific). A 7 kD band corresponding to the size indicated by anti-6728IgG-HRP is visible (red arrow on FIG. 17).

D. Mass Spectrometry Analysis

Mass spectrometry analysis on the band cut from SDS-PAGE gel (pointed by a red arrow on FIG. 17) indicated that this band contains Copro6728, and that the C-terminal portion of DIV6728 contains Copro6728.

The 7 kD band that corresponds to the 7 kD band on the Western blotting was cut out from the SDS-PAGE gel and sent to the Keck Center at Yale University for Mass spectrometry analysis. The sample in the gel was first trypsin digested and then analyzed by LC-MS/MS using the Q-T of of Ultima Mass spectrometer (Waters). Two specific peptides were found in the sample by Mass Spectrometry analysis: Peptide 1: R.FVPCTR.N (SEQ IS NO: 35) and Peptide 2: R.DAEG-NCIK.F (SEQ ID NO: 36).

Alignment analysis on the sequences of DIV6728 (SEQ ID NO: 21) and the two peptides identified by MS analysis indicated that both peptides are located in the C terminal end of the full-length DIV6728, confirming that the 7 kb band identified by Western blot is derived from DIV6728. The location of the two peptide sequences indicates that a C-terminal portion of DIV6728 (Copro6728) was present in the *T. canis* positive fecal samples. FIG. 18 shows the full-length of DIV6728 (SEQ ID NO: 21) with the two peptides identified by MS analysis highlighted in the shaded boxes.

Example 4

Two recombinant proteins were generated that correspond to 64 amino acids within the N-terminal portion of DIV6728 and 65 amino acids within the C-terminal portion of DIV6728.

Based on the MS analysis, western blotting and SDS-PAGE data, two new expression constructs encoding truncations of DIV6728 were made. They were named 6728N (SEQ ID NO: 37) and 6728C (SEQ ID NO: 38) for the N-terminus and C-terminus of full-length DIV6728, respectively. FIG. 19 shows an alignment of the 6728N (SEQ ID NO: 37) and 6728C (SEQ ID NO: 38) amino acid sequences encoded by the constructs.

A. Synthetic Genes for Expressing Recombinant 6728N and 6728C

The genes for expressing 6728N and 6728C polypeptides were codon optimized for expression in *E. coli*, synthesized and cloned into vector pET28(a) with six His(6) tags at the N-terminus of each recombinant protein by GeneArt, (Josef-Engert-Str. 11D-93053 Regensburg, Germany).

B. Recombinant Protein 6728N and 6728C Expression

Figure 20:
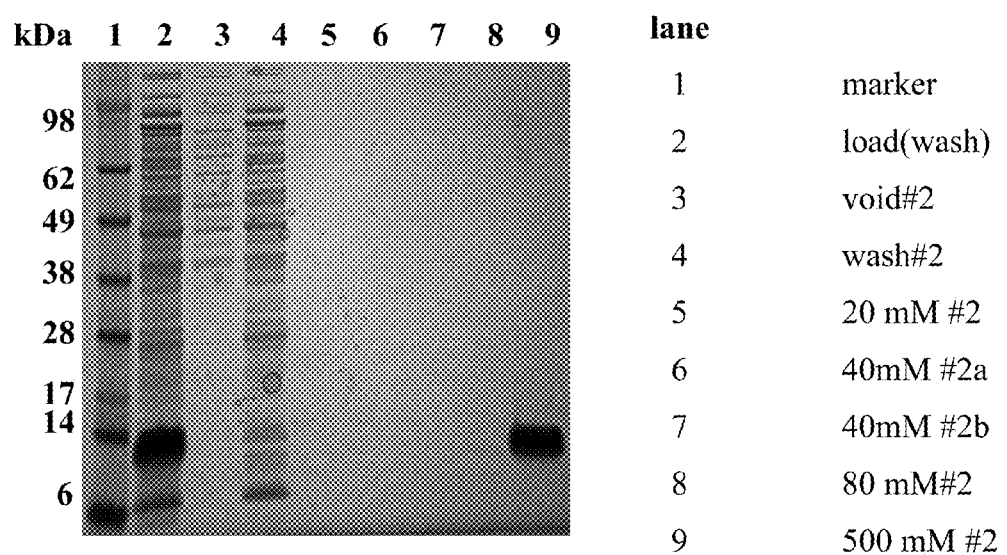
FIG. 20 shows a SDS-PAGE gel loaded with different samples to check the purification of the recombinant 6728N following the method of the present invention in the fourth Example.

Recombinant proteins 6728N and 6728C were expressed in *E. coli* BL21(DE3) and purified with a single nickel column. Plasmid pET28(a) 6728N was transformed into BL21 (DE3), grown to an OD~0.8 and induced with 1 mM IPTG (Isopropyl-1-thio-β-D-galactopyranoside) at 37° C. for 2 hour. Cells were lysed with Microfluidizer® Processor, M-11EH. Recombinant 6728N was soluble in the 20 mM Tris buffer, pH 8.0, with 500 mM NaCl and was purified by step eluting the nickel column with different concentration of imidazole in the 20 mM Tris buffer, pH 8.0, with 500 mM NaCl. The recombinant 6728N was eluted from the Nickel column by the same buffer with 500 mM imidazole. FIG. 20 is a SDS-PAGE gel loaded with different samples to check the purification of the recombinant 6728N. Recombinant 6728N is about ~12 kD in size (lane 9) on the gel.

Figure 21:
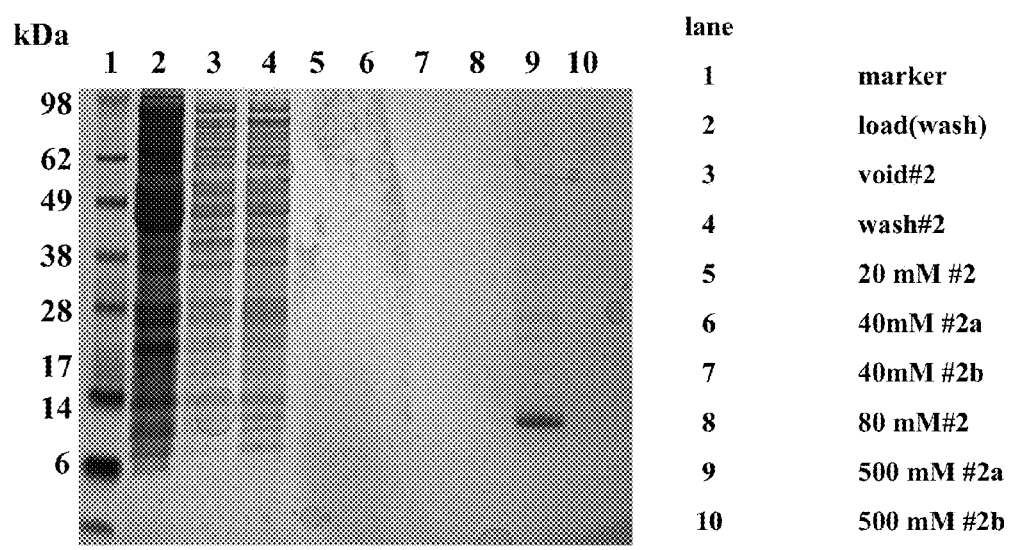
FIG. 21 shows a SDS-PAGE gel loaded with different samples to check the purification of the recombinant 6728C following the method of the present invention in the fourth Example.

Plasmid pET28(a) 6728C was transformed into BL21 (DE3), grown to an OD~0.8 and induced with 1 mM IPTG (Isopropyl-1-thio-β-D-galactopyranoside) at 37° C. for 2 hour. Cells were lysed with Microfluidizer® Processor, M-11EH. Recombinant 6728C was soluble in the mM Tris buffer, pH 8.0, with 500 mM NaCl and was purified by step eluting the nickel column with different concentration of imidazole in the 20 mM Tris buffer, pH 8.0, with 500 mM NaCl. The recombinant 6728C was eluted from the Nickel column by the same buffer with 500 mM imidazole. FIG. 21 is a SDS-PAGE gel loaded with different samples to confirm the purification of the recombinant 6728C. Recombinant 6728C is about ~12 kD in size (lane 9) on this gel.

C. Rabbit Polyclonal Antibodies

Figure 22:
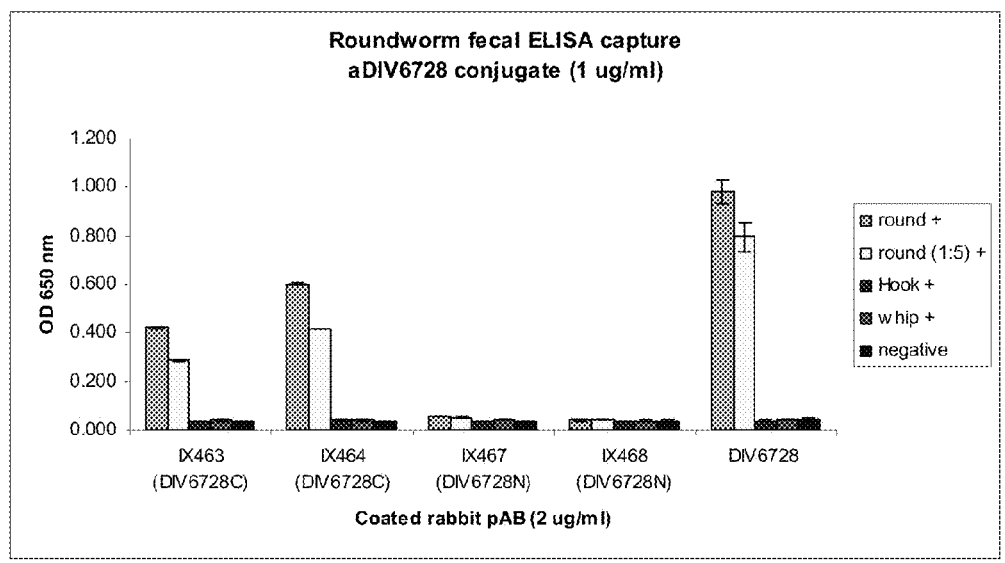
FIG. 22 shows the ELISA data obtained with different fecal samples to test the different polyclonal antibodies against different recombinant 6728 proteins following the method of the present invention in the fourth Example.
Figure 23:
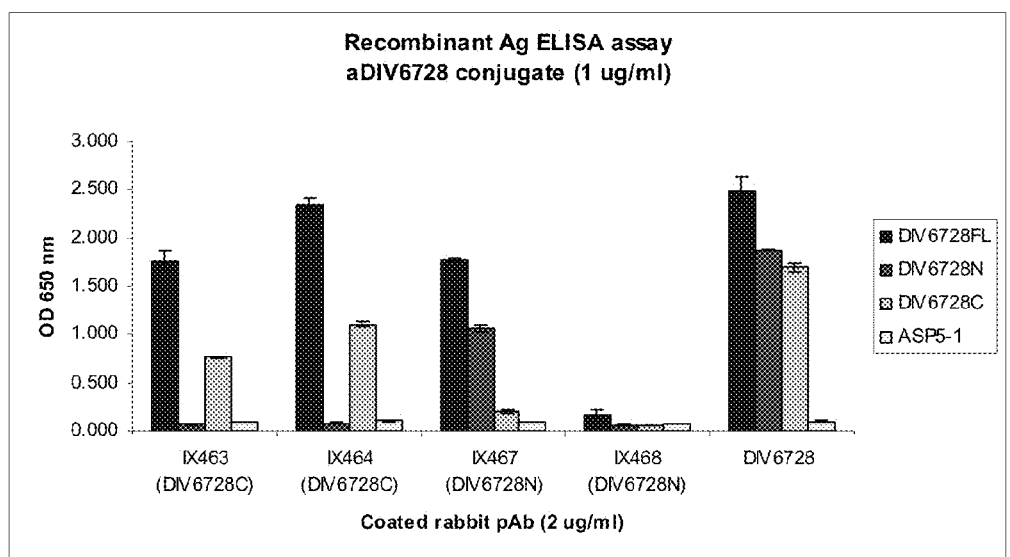
FIG. 23 shows the ELISA data obtained with recombinant proteins to test the different polyclonal antibodies against different recombinant 6728 proteins following the method of the present invention in the fourth Example.

Rabbit polyclonal antibody raised against 6728C detects antigen in fecal ELISA, whereas polyclonal antibody against 6728N does not detect antigen in fecal ELISA Recombinant proteins 6728N and 6728C, purified with a single Nickel column, were used to immunize rabbits for polyclonal antibody production. Polyclonal antibodies from the immunized rabbit sera were affinity purified with Protein G resin and used to coat Immulon I plates at 2 µg/ml. Four different canine samples were tested with different antibody coated plates. Antibodies from the two rabbits immunized with recombinant 6728C could differentiate the *T. canis* positive fecal samples from hookworm, whipworm positive samples and nematode negative samples. However, antibodies from the two rabbits immunized with recombinant 6728N could not differentiate the *T. canis* positive fecal samples from hookworm, whipworm positive samples and nematode negative samples (FIG. 22). This ELISA data further demonstrates that Copro6728 is a C-terminal portion of full-length DIV6728. Further experiments showed that antibodies raised against 6728N and 6728C only recognize their cognate recombinant proteins without cross reactivity. (FIG. 23). Both of these polyclonal antibodies react with full-length recombinant DIV6728 as expected (FIG. 23).

D. Western Blotting

Figure 24:
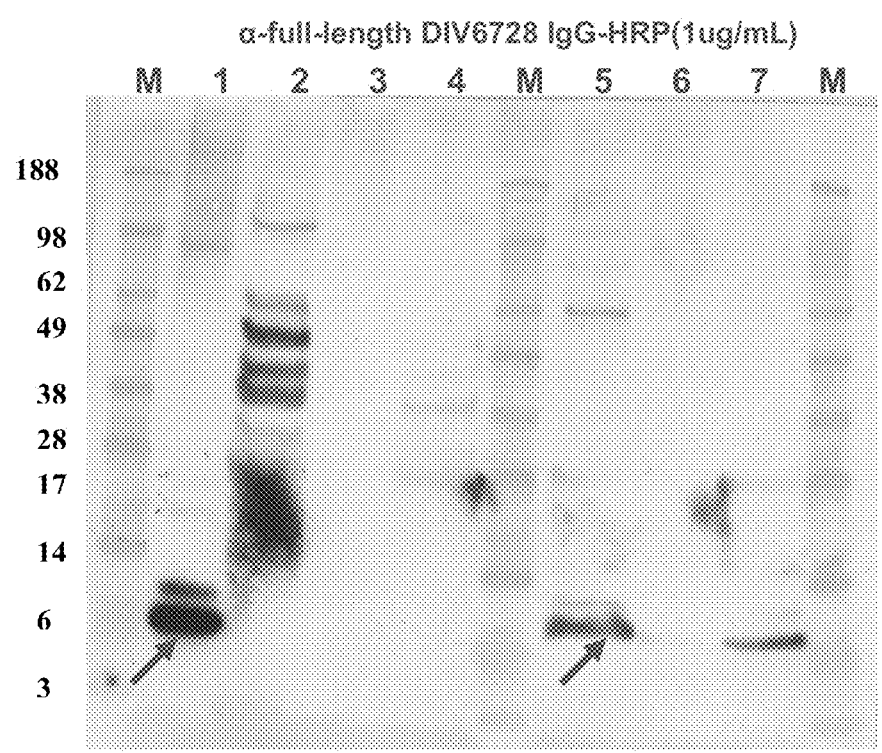
FIG. 24 shows Western blotting with different fecal samples probed with rabbit anti-full-length DIV6728 IgG-HRP following the method of the present invention in the fourth Example.
Figure 25:
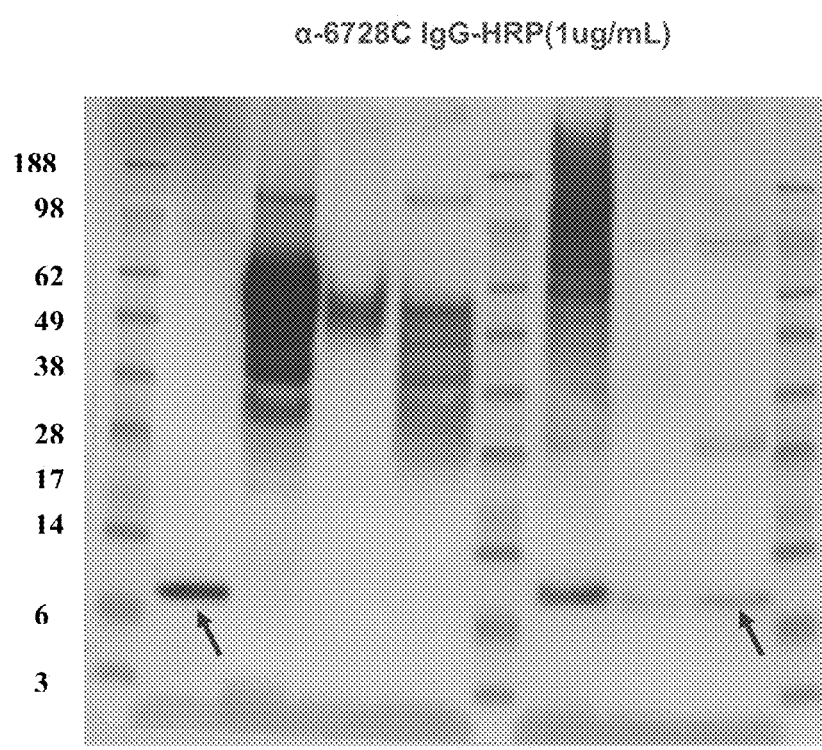
FIG. 25 shows Western blotting with different fecal samples probed with rabbit anti-6728C IgG-HRP following the method of the present invention in the fourth Example.
Figure 26:
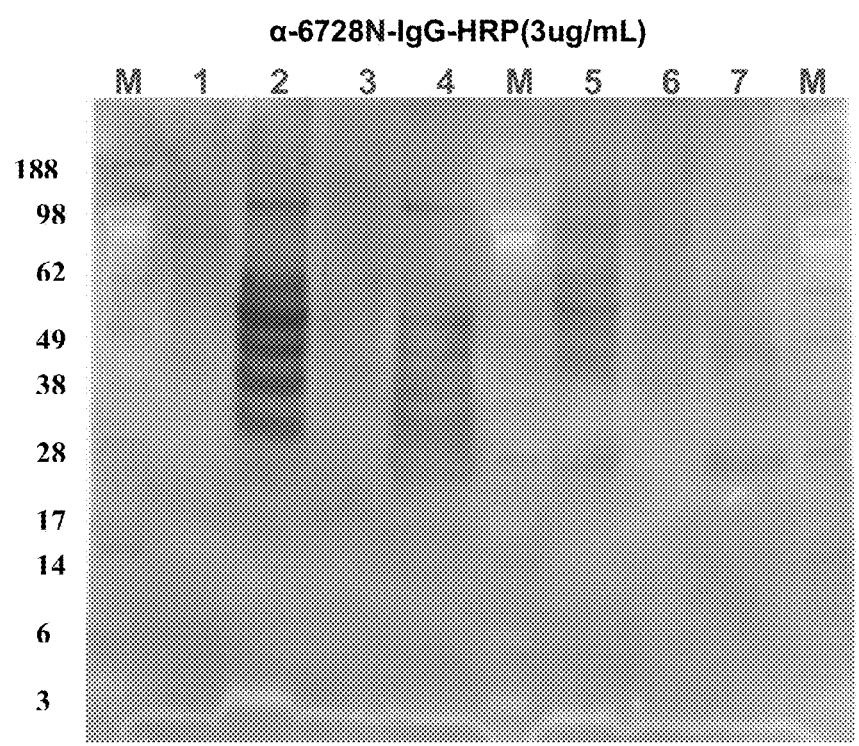
FIG. 26 shows Western blotting with different fecal samples probed with rabbit anti-6728N IgG-HRP following the method of the present invention in the fourth Example.

Rabbit polyclonal antibody against recombinant 6728C can recognize the *T. canis* positive fecal samples in Western Blotting, but not the polyclonal antibody against recombinant 6728N. In addition to *T. canis* whole worm extract (lane 1), nematode negative (lanes 2-4) and *T. canis* positive (lanes 5-7) fecal samples were fractionated by SP column with high salt elution buffer (1 M NaCl in 20 mM sodium citrate buffer, pH 3). The *T. canis* worm extract (lane 1), samples loaded onto the column (lane 2 and 5), column flow-through (lane 3 and 6), and column elution (lane 4 and 7) were loaded to 10 well, 4-12% Bis-Tris gradient gel and then further transferred to nitrocellulose membrane, probed with different conjugates as indicated in FIGS. 24-26. Both the anti-full-length 6728 IgG-HRP and anti-6728C-IgG-HRP could differentiate the *T. canis* positive fecal sample from the nematode negative fecal samples (FIGS. 24 and 25). However, the anti-6728N IgG-HRP could not differentiate these two different fecal samples (FIG. 26). These data further confirmed that Copro6728 is only about half the size of full-length DIV6728, in agreement with the data obtained from Mass spectrometry analysis and fecal ELISA.

We claim:

1. A method of detecting the presence or absence of one or more helminthic antigens in a sample, the method comprising contacting a sample from a mammal with:
   (a) a first antibody capable of specifically binding a roundworm coproantigen, but not a whipworm coproantigen;
   (b) a second antibody capable of specifically binding a whipworm coproantigen, but not a roundworm coproantigen;
   (c) forming antibody-coproantigen complexes in the presence of the coproantigens, if any, in the sample; and
   (d) detecting the presence or absence of the antibody-coproantigen complexes, if any.

2. A method of detecting the presence or absence of one or more helminthic antigens in a sample, the method comprising contacting a sample from a mammal with:
   (a) a first antibody capable of specifically binding a roundworm coproantigen, but not a hookworm coproantigen;
   (b) a second antibody capable of specifically binding a hookworm coproantigen, but not a roundworm coproantigen;
   (c) forming antibody-coproantigen complexes in the presence of the coproantigens, if any, in the sample; and
   (d) detecting the presence or absence of the antibody-coproantigen complexes, if any.

3. A method of detecting the presence or absence of one or more helminthic antigens in a sample, the method comprising contacting a sample from a mammal with:
   (a) a first antibody capable of specifically binding a whipworm coproantigen, but not a hookworm coproantigen;
   (b) a second antibody capable of specifically binding a hookworm coproantigen, but not a whipworm coproantigen;
   (c) forming antibody-coproantigen complexes in the presence of the coproantigens, if any, in the sample; and
   (d) detecting the presence or absence of the antibody-coproantigen complexes, if any.

4. The method of any one of claim 1, 2, or 3, further comprising the step of contacting the sample with one or more reagents to detect one or more of the group consisting of: one or more non-worm parasites, heartworm, one or more viruses, one or more fungi, and one or more bacteria.

5. The method of claim 4, wherein the reagents for the detection of any one or all of the one or more non-worm parasites, one or more viruses, one or more fungi and the one or more bacteria are one or more antibodies or one or more antigens recognized by antibodies specific for one or more non-worm parasites, one or more viruses, one or more fungi or one or more bacteria.

6. The method of any one of claim 1 or 2, wherein the antibody capable of specifically binding a roundworm coproantigen is capable of specifically binding a polypeptide consisting of an amino acid sequence of SEQ ID NO:12, SEQ ID NO:13, SEQ ID NO: 14, SEQ ID NO: 15, SEQ ID NO: 16, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO: 38, or Copro6728; or the antibody was raised against an extract of whole roundworms, or extract of roundworm reproductive organs, or extract of roundworm intestines.

7. The method of any one of claim 1 or 3, wherein the antibody capable of specifically binding a whipworm coproantigen is capable of specifically binding a polypeptide consisting of an amino acid sequence of SEQ ID NO:3, SEQ ID NO: 4, SEQ ID NO: 5, SEQ ID NO: 6, SEQ ID NO: 7, SEQ ID NO: 8, or SEQ ID NO: 9.

8. The method of any one of claim 2 or 3, wherein the antibody capable of specifically binding a hookworm coproantigen is capable of specifically binding a polypeptide consisting of an amino acid sequence of SEQ ID NO:33 or SEQ ID NO: 34, or CoproASP5.

9. The method of any one of claim 1, 2, or 3, wherein the sample is obtained from a mammal that is a canine or a feline.

10. The method of any one of claim 1 or 2, wherein the roundworm is *Toxocara canis* or *Toxocara cati*, *Toxocara vitulorum*, *Toxascaris leonina*, *Baylisascaris procyonis*, *Ascaridia galli*, *Parascaris equorum*, *Ascaris suum*, *Ascaris lumbricoides*, *Anisakis simplex*, or *Pseudoterranova decipiens*.

11. The method of any one of claim 1 or 3, wherein the whipworm is *Trichuris vulpis*, *Trichuris campanula*, *Trichuris serrata*, *Trichuris suis*, *Trichuris trichiura*, *Trichuris discolor* and *Trichocephalus trichiuris*.

12. The method of any one of claim 2 or 3, wherein the hookworm is *Ancylostoma caninum*, *Ancylostoma braziliense*, *Ancylostoma duodenal*, *Ancylostoma ceylanicum*, *Ancylostoma tubaeforme* and *Ancylostoma pluridentatum*, *Necator americanus*, and *Uncinaria stenocephala*.

13. The method of any one of claim 1, 2, or 3, wherein the first and second antibodies do not specifically bind any coproantigen derived from heartworm.

14. The method of any one of claim 1, 2, or 3, wherein the step of detecting the presence or absence of the complexes further includes the step of providing at least one secondary antibody that binds to at least one of the complexes.

15. The method of claim 14, wherein the at least one secondary antibody is labeled.

16. The method of any one of claim 1, 2, or 3, wherein one or more of the first and second antibodies are labeled.

17. The method of any one of claim 1, 2, or 3, wherein the first and second antibodies are immobilized on a solid support.

18. The method of claim 17, wherein the solid support forms part of an enzyme-linked immunosorbent assay device.

19. The method of claim 18, wherein the enzyme-linked immunosorbent assay device is a lateral flow immunoassay device.

20. The method of any one of claim 1, 2, or 3, wherein the roundworm coproantigen, hookworm coproantigen, and/or whipworm coproantigen is from a fecal sample.

21. A method of diagnosing whether a mammal is infected with one or more parasitic worms, the method comprising the steps of:
(a) contacting a sample from a mammal with:
(i) a first antibody capable of specifically binding a roundworm coproantigen, but not a whipworm coproantigen; and
(ii) a second antibody capable of specifically binding a whipworm coproantigen, but not a roundworm coproantigen;
(b) forming antibody-coproantigen complexes in the presence of the coproantigens, if any, in the sample;
(c) detecting the presence or absence of the antibody-coproantigen complexes, if any; and
(d) diagnosing the mammal as having:
(i) a roundworm infection if a roundworm antibody-coproantigen complex is present; and
(ii) a whipworm infection if a whipworm antibody-coproantigen complex is present.

22. A method of diagnosing whether a mammal is infected with one or more parasitic worms, the method comprising the steps of:
(a) contacting a sample from a mammal with:
(i) a first antibody capable of specifically binding a roundworm coproantigen, but not a hookworm coproantigen;
(ii) a second antibody capable of specifically binding a hookworm coproantigen, but not a roundworm coproantigen;
(b) forming antibody-coproantigen complexes in the presence of the coproantigens, if any, in the sample;
(c) detecting the presence or absence of the antibody-coproantigen complexes, if any; and
(d) diagnosing the mammal as having:
(i) a roundworm infection if a roundworm antibody-coproantigen complex is present; and
(ii) a hookworm infection if a hookworm antibody-coproantigen complex is present.

23. A method of diagnosing whether a mammal is infected with one or more parasitic worms, the method comprising the steps of:
(a) contacting a sample from a mammal with:
(i) a first antibody capable of specifically binding a whipworm coproantigen, but not a hookworm coproantigen;
(ii) a second antibody capable of specifically binding a hookworm coproantigen, but not a whipworm coproantigen;
(b) forming antibody-coproantigen complexes in the presence of the coproantigens, if any, in the sample;
(c) detecting the presence or absence of the antibody-coproantigen complexes, if any; and
(d) diagnosing the mammal as having:
(i) a whipworm infection if a whipworm antibody-coproantigen complex is present; and
(ii) a hookworm infection if a hookworm antibody-coproantigen complex is present.

* * * * *